us010561805B2

United States Patent
Allosery et al.

(10) Patent No.: US 10,561,805 B2
(45) Date of Patent: Feb. 18, 2020

(54) METHODS OF TREATING RSV INFECTIONS

(71) Applicants: ABLYNX N.V., Ghent-Zwijnaarde (BE); VECTURA GMBH, Gauting (DE)

(72) Inventors: Koen Allosery, Ostend (BE); Erik Depla, Destelbergen (BE); Martin Huber, Gauting (DE); Tobias Kolb, Gauting (DE); Bernhard Müllinger, Gauting (DE); Massimiliano Germani, Geel (BE); Juliane Schick, Gauting (DE); Maria-Laura Sargentini, Brussels (BE)

(73) Assignees: ABLYNX N.V., Ghent-Zwijnaarde (BE); VECTURA GMBH, Gauting (DE)

( * ) Notice: Subject to any disclaimer, the term of this patent is extended or adjusted under 35 U.S.C. 154(b) by 63 days.

(21) Appl. No.: 15/517,693

(22) PCT Filed: Oct. 9, 2015

(86) PCT No.: PCT/EP2015/073487
§ 371 (c)(1),
(2) Date: Apr. 7, 2017

(87) PCT Pub. No.: WO2016/055656
PCT Pub. Date: Apr. 14, 2016

(65) Prior Publication Data
US 2017/0304566 A1  Oct. 26, 2017

Related U.S. Application Data

(60) Provisional application No. 62/062,469, filed on Oct. 10, 2014, provisional application No. 62/067,096, filed on Oct. 22, 2014, provisional application No. 62/074,842, filed on Nov. 4, 2014.

(30) Foreign Application Priority Data

Nov. 13, 2014 (EP) .................................... 14193094

(51) Int. Cl.
*A61K 39/42* (2006.01)
*A61M 15/00* (2006.01)
*A61K 9/00* (2006.01)
*A61M 15/02* (2006.01)
*C07K 16/10* (2006.01)
*A61K 45/06* (2006.01)
*A61K 39/00* (2006.01)

(52) U.S. Cl.
CPC ......... *A61M 15/002* (2014.02); *A61K 9/0078* (2013.01); *A61K 39/42* (2013.01); *A61K 45/06* (2013.01); *A61M 15/009* (2013.01); *A61M 15/0021* (2014.02); *A61M 15/025* (2014.02); *C07K 16/10* (2013.01); *C07K 16/1027* (2013.01); *A61K 2039/505* (2013.01); *A61K 2039/54* (2013.01); *A61K 2039/545* (2013.01); *A61M 2202/025* (2013.01); *A61M 2202/0208* (2013.01); *A61M 2202/0266* (2013.01); *A61M 2206/11* (2013.01); *A61M 2240/00* (2013.01); *C07K 2317/56* (2013.01); *C07K 2317/565* (2013.01); *C07K 2317/567* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2012/0128669 A1 | 5/2012 | Depla et al. |
| 2012/0167878 A1 | 7/2012 | Belson et al. |
| 2012/0318265 A1 | 12/2012 | Amirav et al. |
| 2013/0008436 A1 | 1/2013 | Von Hollen et al. |
| 2013/0019860 A1 | 1/2013 | Depla et al. |
| 2013/0104887 A1 | 5/2013 | Smutney et al. |
| 2013/0136744 A1 | 5/2013 | Bouche et al. |
| 2013/0273037 A1* | 10/2013 | Siegel .................. C07D 487/04 424/133.1 |
| 2014/0020680 A1 | 1/2014 | Fink et al. |

FOREIGN PATENT DOCUMENTS

| | | |
|---|---|---|
| EP | 0368684 | 3/1994 |
| EP | 1908489 | 4/2008 |
| EP | 2724741 | 4/2014 |
| JP | 2007531577 | 11/2007 |
| WO | 1994004678 | 3/1994 |
| WO | 1999042077 | 8/1999 |

(Continued)

OTHER PUBLICATIONS

Aerogen Solo System Instruction Manual [www.aerogen.com] dated 2014.
Arzu Ari, "Performance Comparisons of Jet and Mesh Nebulizers with Mouthpiece, Aerosol Mask, and Valved Mask in Simulated Spontaneously Breathing Adults." Chest 2014.
Depla, Erik: "Nanobodies—Inspired by nature Development of ALX-0171, an inhaled Nanobody for the treatment of respiratory syncytial virus infection in infants" Human Antibodies and Hybridomas, Apr. 2, 2014 (Apr. 2, 2014), XP055235944, Vienna, Austria.

(Continued)

*Primary Examiner* — Shanon A. Foley
*Assistant Examiner* — Myron G Hill
(74) *Attorney, Agent, or Firm* — Matthew S. Gibson; Ryan P. Cox; Reed Smith LLP

(57) ABSTRACT

Methods are provided for the treatment of RSV infections in young children. More specifically, methods are provided wherein polypeptides that bind F protein of hRSV and that neutralize RSV infection are administered to the lungs of young children at specific dose regimens.

10 Claims, 38 Drawing Sheets
Specification includes a Sequence Listing.

(56) References Cited

FOREIGN PATENT DOCUMENTS

| WO | 2004068820 | | 8/2004 |
|---|---|---|---|
| WO | 2005018629 | | 3/2005 |
| WO | 2005025540 | | 3/2005 |
| WO | 2006003388 | | 1/2006 |
| WO | 2006006963 | | 1/2006 |
| WO | 2006030220 | | 3/2006 |
| WO | 2006059108 | | 6/2006 |
| WO | 2007049017 | | 5/2007 |
| WO | 2007085815 | | 8/2007 |
| WO | 2008101985 | | 8/2008 |
| WO | 2008116165 | | 9/2008 |
| WO | 2008142164 | | 11/2008 |
| WO | 2010139808 | | 12/2010 |
| WO | 2011098552 | | 8/2011 |
| WO | WO2011098552 | * | 8/2011 |
| WO | 2013067164 | | 5/2013 |
| WO | 2013098334 | | 7/2013 |
| WO | 2013132056 | | 9/2013 |
| WO | 2014159822 | | 10/2014 |

OTHER PUBLICATIONS

Ingrid Ottevaere et al: "IL-40 Population PK of ALX-0171, an inhaled Respiratory Syncytial Virus (RSV) neutralizing Nanody" p. 2014 meeting, Twenty-third meeting Jun. 10-13, 2014, Abstract 3114, Jun. 11, 2014 (Jun. 11, 2014), XP055236302, Alicante Spain.
Collingwood et al: "Respiratory Drug Discovery, Current Developments and Future Challenges", Drugs of the Future, Aug. 1, 2012 (Aug. 1, 2012), pp. 619-625, XP055061153, DOI: 10.1358/dof. 2012.37.8.1854604.
International Search Report and Written Opinion in PCT/EP2015/073487 dated Dec. 16, 2015.
Knoch, Martin and Keller, Manfred. "The customised electronic nebuliser: a new category of liquid aerosol drug delivery systems," Expert opinion on drug delivery, vol. 2(2), 2005, p. 377-390.
Arzu Ari, "Performance Comparisons of Jet and Mesh Nebulizers with Mouthpiece, Aerosol Mask, and Valved Mask in Simulated Spontaneously Breathing Adults and Children." Journal of Aerosol Medicine and Pulmonary Drug Delivery, vol. 28, No. 0, 2014, pp. 1-9.
Nahata MC., et al., Management of bronchiolitis, Clin. Pharm. May-Jun. 1985; 4(3):297-303, abstract.
English translation of Search Report, Russian Application No. 2017115670, search completed May 12, 2019.
English translation of Official Action, Russian Application No. 2017115670, dated May 16, 2019.
Search Report, Russian Application No. 2017115845, search completed Apr. 12, 2019.
English translation of Official Action, Russian Application No. 2017115845, dated Apr. 12, 2019.
Totapally et al.; Critical Care 2002, 6:160-165.
Ward et al. 1989 (Nature 341:544-546).
Holt et al. 2003 (Trends Biotechnol. 21:484-490).
Muyldermans 2001 (Reviews in Molecular Biotechnology 74:277-302).
Davies and Riechmann 1994 (FEBS 339:285-290).
1995 (Biotechnol. 13:475-479).
1996 (Prot. Eng. 9:531-537).
Reichmann and Muyldermans 1999 (J. Immunol. Methods 231:25-38).
Janssens et al.; J Aerosol Med. 2001 Winter; 14(4):433-41.
Notice of Reasons for Rejection, Japanese Patent Office, Application No. 2017538457, dated Mar. 4, 2019, English Translation.
International Search Report and Written Opinion of PCT/EP15/73486 dated Dec. 10, 2015.
International Preliminary Report on Patentability of PCT/EP15/73486 dated Dec. 19, 2016.

* cited by examiner

C

A.

B.

METHODS OF TREATING RSV INFECTIONS

RELATED APPLICATIONS

This application is a United States national stage of International Application No. PCT/EP2015/073487, filed Oct. 9, 2015, which was published as International Publication No. WO 2016/055656, and which claims benefit of U.S. Provisional Patent Application No. 62/062,469, filed Oct. 10, 2014, U.S. Provisional Patent Application No. 62/067,096, filed Oct. 22, 2014, U.S. Provisional Patent Application No. 62/074,842, filed Nov. 4, 2014, and European Patent Application No. 14193094.1, filed Nov. 13, 2014, the entire contents of which are hereby expressly incorporated herein by reference thereto.

FIELD OF THE INVENTION

The present invention provides methods for the treatment of RSV infections in young children. More specifically, the present invention provides specific dose regimens of immunoglobulin single variable domains that neutralize RSV for pulmonary administration to young children.

BACKGROUND OF THE INVENTION

Respiratory syncytial virus (RSV) is a recurrent cause of severe respiratory tract infections in infants and very young children and causes annual epidemics during the winter months. RSV typically causes its primary infection at the point of entry: the ciliated epithelial cells that line the nasal cavity and airways (Black 2003, Respir. Care 48: 209-31; discussion 231-3). Primary infections are usually symptomatic with clinical signs ranging from mild upper respiratory tract illness to more severe lower respiratory tract infections (LRTIs), including bronchopneumonia and bronchiolitis (Aliyu, et al. 2010, Bayero Journal of Pure and Applied Sciences 3: 147-155), which occurs predominantly in infants.

The transmembrane glycoproteins F and G are the primary surface antigens of RSV. The attachment protein (G) mediates binding to cell receptors, while the F protein promotes fusion with cell membranes, allowing penetration into the host cell (Lopez et al. 1998, 72: 6922-8). Based on antigenic and genetic variability of the G protein, 2 serotypes of RSV have been identified (A and B), along with several subtypes.

In contrast to the G protein, the F protein is highly conserved between RSV serotypes A and B (89% amino acid identity), and is therefore considered the main target for development of viral entry inhibitors. Glycoprotein F also induces fusion of infected cells with adjacent uninfected cells. This hallmark feature results in the appearance of multinucleate cell formations (epithelial cell syncytia), which allow for cell-to-cell transmission of replicated viral ribonucleic acid (RNA), conferring additional protection against host immune responses (Black 2003).

RSV infection imposes a significant burden on health care infrastructure and there remains a high medical need for treatment options, especially since there is no vaccine available to prevent RSV infections.

The only drug product available in the market is a humanized monoclonal antibody (SYNAGIS® (palivizumab)) directed against the viral glycoprotein F which is used prophylactically in children that are at a very high risk of suffering a severe hRSV infection. The restricted use of SYNAGIS® is due, at least in part, to the high cost of this product. Since there are no adequate medications available for treatment of RSV infection, the standard of care for hospitalized infants is mostly supportive (e.g., fluid/feed supplementation, observation, and respiratory support as needed). There is clearly a need for improved and/or cheaper prophylactic and/or therapeutic agents for the prevention and/or treatment of infections by hRSV.

SEQ ID NOs: 65-85 of the present disclosure are immunoglobulin single variable domains directed against the fusion protein of the human respiratory syncytial virus. SEQ ID NOs: 65-85 consist of 3 anti-hRSV immunoglobulin single variable domains, recombinantly linked by a flexible linker.

SEQ ID NOs: 65-85 were extensively characterized in vitro and in vivo (see for example WO 2010/139808; the contents of which are incorporated by reference in their entirety). The anti-hRSV immunoglobulin single variable domains specifically and potently bind to the respiratory syncytial virus (RSV) F protein. In vitro micro-neutralization studies in HEp2 cells, suggested that these anti-hRSV immunoglobulin single variable domains inhibit an early event in the viral life cycle, preventing extracellular virus from infecting virus naïve cells. Efficacy of SEQ ID NOs: 65-85 was confirmed in RSV-infected cotton rats.

Since SEQ ID NOs: 65-85 are intended to neutralize and inhibit RSV, direct delivery and deposition in the respiratory tract through an aerosol device is considered the preferred and most suitable route of administration. Formulation of immunoglobulin single variable domains (including SEQ ID NOs: 65-85) as a nebulizer solution has been extensively described in WO 2011/098552.

The safety, tolerability and pharmacokinetic (PK) parameters of inhalation of SEQ ID NO: 71 have further been evaluated in three Phase I clinical studies in adult volunteers. These studies showed that inhalation and intravenous (i.v.) infusion of SEQ ID NO: 71 is generally well-tolerated. There is, however, no possibility for extrapolating efficacy from adults to children, or from older to younger children, as lower respiratory tract disease caused by RSV rarely occurs in these populations.

SUMMARY OF THE INVENTION

To address this long-felt but unmet need for an effective prevention and/or treatment of RSV infections, particularly in high-risk populations such as children, the present invention provides dose regimens for pulmonary administration of a biological in a pediatric population. More particularly, the present invention provides dose regimens for the pulmonary administration of an immunoglobulin single variable domain to young children, such as infants and toddlers.

As indicated above, for RSV neutralizing drugs, there is no possibility for extrapolating efficacy from adults to children, or from older to younger children, as lower respiratory tract disease caused by RSV rarely occurs in these populations. Therefore, dose determination can only be based on a modelling approach.

Dose determinations for pediatric populations traditionally scale from adult doses using functions related to body weight, height, or age. Certain therapeutics (such as e.g. PULMOZYME® (dornase alfa)) are given as a fixed dose to all ages including infants. Unlike these usual dose determinations, in the present invention a modelling approach was designed also taking into account growth and development processes such as organ maturation, changes in blood flow, body composition, and ontogeny of elimination mechanisms, including the delivery and deposition of the drug in and its absorption from the developing alveolar space.

The present invention unexpectedly determined that dose regimens for pulmonary administration of a biological to a young child are mainly driven by the difference in physiology of the child and its maturing organs. More particularly the present inventors determined that the dose determination in the present invention was mainly guided by a difference in pulmonary delivery, distribution and absorption of the drug in the developing child's lung compared to delivery, distribution and absorption in an adult lung. Therefore, the primary important parameter driving systemic as well as local PK in the RSV infected children appeared to be the amount of drug in alveolar absorption space. Based the modeling approach of the present invention, the target concentration at which a clinically meaningful reduction of RSV activity is obtained (9 µg/ml) was estimated to be reached in the alveolar space using a deposited dose of 0.024 mg/kg body weight. Since the alveolar surface area and with that, the alveolar volume, scaled with the body weight, the alveolar concentration was virtually not age dependent for a body weight normalized dose.

Based on the above designed model and observations, the present invention provides a dose regimen for the pulmonary administration, to paediatric subjects, of a RSV neutralizing immunoglobulin single variable domain, a dose regimen that results in local drug concentrations in the lower respiratory tract at which antiviral activity is observed.

Accordingly, the present invention relates to a method for the treatment of RSV infection in a young child, said method comprising the administration to the child suffering the RSV infection, of a polypeptide that binds F-protein of hRSV with a $K_D$ of $5\times10^{-10}$ M or less, that neutralizes hRSV with an IC90 of 90 ng/mL or less, and that comprises, consists essentially of, or consists of three anti-hRSV immunoglobulin single variable domains, wherein the polypeptide is administered to the child by inhalation at a deposited dose of 0.020-0.040 mg/kg daily, preferably 0.020-0.035 mg/kg daily, such as e.g. 0.024 mg/kg daily. In certain aspects of this method, the $K_D$ may be measured by an immunoassay. Alternatively, or in addition, in certain aspects of this method, the IC90 may be measured in a micro-neutralization assay.

The invention also relates to a polypeptide that binds F-protein of hRSV with a $K_D$ of $5\times10^{-10}$ M or less, that neutralizes hRSV with an IC90 of 90 ng/mL or less, and that comprises, consists essentially of, or consists of three anti-hRSV immunoglobulin single variable domains, for use in the treatment of RSV infection in a young child, wherein the polypeptide is administered, to the child suffering RSV infection, by inhalation at a deposited dose of 0.020-0.040 mg/kg daily, preferably 0.020-0.035 mg/kg daily, such as e.g. 0.024 mg/kg daily. In certain aspects of this polypeptide, the $K_D$ may be measured by an immunoassay. Alternatively, or in addition, in certain aspects of this polypeptide, the IC90 may be measured in a micro-neutralization assay.

The present invention also relates to a method for the treatment of RSV infection in a young child, said method comprising the administration to the child suffering the RSV infection, of a polypeptide that binds F-protein of hRSV with a $K_D$ of $5\times10^{-10}$ M or less, that neutralizes hRSV with an IC90 of 90 ng/mL or less, and that comprises, consists essentially of, or consists of three anti-hRSV immunoglobulin single variable domains, wherein the polypeptide is administered to the child by inhalation at an inhaled dose of 0.20-0.40 mg/kg daily, preferably 0.20-0.35 mg/kg daily, such as e.g. 0.24 mg/kg daily. In certain aspects of this method, the $K_D$ may be measured by an immunoassay. Alternatively, or in addition, in certain aspects of this method, the IC90 may be measured in a micro-neutralization assay.

The invention also relates to a polypeptide that binds F-protein of hRSV with a $K_D$ of $5\times10^{-10}$ M or less, that neutralizes hRSV with an IC90 of 90 ng/mL or less, and that comprises, consists essentially of, or consists of three anti-hRSV immunoglobulin single variable domains, for use in the treatment of RSV infection in a young child, wherein the polypeptide is administered, to the child suffering RSV infection, by inhalation at an inhaled dose of 0.20-0.40 mg/kg daily, preferably 0.20-0.35 mg/kg daily, such as e.g. 0.24 mg/kg daily. In certain aspects of this polypeptide, the $K_D$ may be measured by an immunoassay. Alternatively, or in addition, in certain aspects of this polypeptide, the IC90 may be measured in a micro-neutralization assay.

The present invention also relates to a method for the treatment of RSV infection in a young child, said method comprising the administration to the child suffering the RSV infection, of a polypeptide that binds F-protein of hRSV with a $K_D$ of $5\times10^{-10}$ M or less, that neutralizes hRSV with an IC90 of 90 ng/mL or less, and that comprises, consists essentially of, or consists of three anti-hRSV immunoglobulin single variable domains, wherein the polypeptide is administered to the child by inhalation at a nominal dose of 1.00-2.00 mg/kg daily, preferably 1.00-1.75 mg/kg daily, such as e.g. 1.20 mg/kg daily. In certain aspects of this method, the $K_D$ may be measured by an immunoassay. Alternatively, or in addition, in certain aspects of this method, the IC90 may be measured in a micro-neutralization assay.

The invention also relates to a polypeptide that binds F-protein of hRSV with a $K_D$ of $5\times10^{-10}$ M or less, that neutralizes hRSV with an IC90 of 90 ng/mL or less, and that comprises, consists essentially of, or consists of three anti-hRSV immunoglobulin single variable domains, for use in the treatment of RSV infection in a young child, wherein the polypeptide is administered, to the child suffering RSV infection, by inhalation at a nominal dose of 1.00-2.00 mg/kg daily, preferably 1.00-1.75 mg/kg daily, such as e.g. 1.20 mg/kg daily. In certain aspects of this polypeptide, the $K_D$ may be measured by an immunoassay. Alternatively, or in addition, in certain aspects of this polypeptide, the IC90 may be measured in a micro-neutralization assay.

RSV infection includes RSV infection of the upper respiratory tract, RSV infection of the lower respiratory tract, including bronchiolitis and broncho-pneumonia, as well as diseases and/or disorders associated with RSV infection such as respiratory illness, upper respiratory tract infection, lower respiratory tract infection, bronchiolitis (inflammation of the small airways in the lung), pneumonia, dyspnea, cough, (recurrent) wheezing and (exacerbations of) asthma or COPD (chronic obstructive pulmonary disease) associated with hRSV. In one aspect, the RSV infection is RSV lower respiratory tract infection. Accordingly, the present invention r elates to a method for the treatment of RSV lower respiratory tract infection in a young child, said method comprising the administration to the child suffering the RSV lower respiratory tract infection, of a polypeptide that binds F-protein of hRSV with a $K_D$ of $5\times10^{-10}$ M or less, that neutralizes hRSV with an IC90 of 90 ng/mL or less, and that comprises, consists essentially of, or consists of three anti-hRSV immunoglobulin single variable domains, wherein the polypeptide is administered to the child by inhalation at a deposited dose of 0.020-0.040 mg/kg daily, preferably 0.020-0.035 mg/kg daily, such as e.g. 0.024 mg/kg daily; at an inhaled dose of 0.20-0.40 mg/kg daily, preferably 0.20-0.35 mg/kg daily, such as e.g. 0.24 mg/kg daily; at a nominal dose of 1.00-2.00 mg/kg daily, preferably 1.00-1.75 mg/kg daily, such as e.g. 1.20 mg/kg daily. In certain aspects of this method, the $K_D$ may be measured by an immunoassay. Alternatively, or in addition, in certain aspects of this method, the IC90 may be measured in a micro-neutralization assay. The invention also relates to a polypeptide that binds F-protein of hRSV with a $K_D$ of $5 \times 10^{-10}$ M or less, that neutralizes hRSV with an IC90 of 90 ng/mL or less, and that comprises, consists essentially of, or consists of three anti-hRSV immunoglobulin single variable domains, for use in the treatment of RSV low respiratory tract infection in a young child, wherein the polypeptide is administered, to the child suffering RSV low respiratory tract infection, by inhalation at a deposited dose of 0.020-0.040 mg/kg daily, preferably 0.020-0.035 mg/kg daily, such as e.g. 0.024 mg/kg daily; at an inhaled dose of 0.20-0.40 mg/kg daily, preferably 0.20-0.35 mg/kg daily, such as e.g. 0.24 mg/kg daily; at a nominal dose of 1.00-2.00 mg/kg daily, preferably 1.00-1.75 mg/kg daily, such as e.g. 1.20 mg/kg daily. In certain aspects of this polypeptide, the $K_D$ may be measured by an immunoassay. Alternatively, or in addition, in certain aspects of this polypeptide, the IC90 may be measured in a micro-neutralization assay.

In one aspect, the young child is aged less than 24 months.

In one aspect, the young child is aged less than 36 months.

In one aspect, the young child is aged 1 month to less than 24 months.

In one aspect, the young child is aged 1 month to less than 36 months.

In one aspect, the young child is aged 5 months to less than 24 months.

In one aspect, the young child is aged 5 months to less than 36 months.

In one aspect, the young child is an infant.

In one aspect, the young child is a toddler.

In one aspect, the young child is diagnosed with RSV lower respiratory tract infection but is otherwise healthy.

In one aspect, the young child is hospitalised for RSV lower respiratory tract infection.

The polypeptide (also referred to as "polypeptide of the invention") comprises, consists essentially of, or consists of three anti-hRSV immunoglobulin single variable domains. In one aspect, the polypeptide of the invention binds F-protein of hRSV with a $K_D$ of $5 \times 10^{-10}$ M or less. In one aspect, the polypeptide of the invention neutralizes hRSV with an IC90 of 90 ng/mL or less. In a preferred aspect, the polypeptide of the invention binds F-protein of hRSV with a $K_D$ of $5 \times 10^{-10}$ M or less and neutralizes hRSV with an IC90 of 90 ng/mL or less. In certain aspects of this polypeptide, the $K_D$ may be measured by an immunoassay. Alternatively, or in addition, in certain aspects of this polypeptide, the IC90 may be measured in a micro-neutralization assay.

Preferred polypeptides of the invention encompass at least one (preferably two, most preferably three) anti-RSV immunoglobulin single variable domain(s) that comprises a CDR1 having the amino acid sequence of SEQ ID NO: 46, a CDR2 having the amino acid sequence of one of SEQ ID NOs: 49-50, and a CDR3 having the amino acid sequence of SEQ ID NO: 61. In one aspect, preferred polypeptides of the invention encompass at least one (preferably two, most preferably three) anti-RSV immunoglobulin single variable domain(s) selected from one of the amino acid sequences of SEQ ID NOs: 1-34. In one aspect, the polypeptide of the invention is selected from one of the amino acid sequences of SEQ ID NOs: 65-85, preferably SEQ ID NO: 71.

The polypeptide of the invention can be administered as a monotherapy or in combination with another therapeutic agent. In one aspect, the polypeptide of the invention is administered as a monotherapy. In one aspect, polypeptide of the invention is administered as a combination therapy.

Accordingly, the invention also provides a method for the treatment of RSV infection, such as RSV lower respiratory tract infection, in a young child, said method comprising the simultaneous, separate or sequential administration by inhalation, to the child suffering the RSV infection, of an anti-RSV polypeptide that binds F-protein of RSV with a $K_D$ of $5 \times 10^{-10}$ M or less, that neutralizes RSV with an IC90 of 90 ng/mL or less, and that comprises, consists essentially of, or consists of three anti-RSV immunoglobulin single variable domains, and a bronchodilator, wherein the polypeptide is administered to the child by inhalation at a deposited dose of 0.020-0.040 mg/kg daily, 0.020-0.035 mg/kg daily, or 0.024 mg/kg daily. In certain aspects of this method, the $K_D$ may be measured by an immunoassay. Alternatively, or in addition, in certain aspects of this method, the IC90 may be measured in a micro-neutralization assay.

Accordingly in another aspect, the invention also provides a method for the treatment of RSV infection, such as RSV lower respiratory tract infection, in a young child, said method comprising the simultaneous, separate or sequential administration by inhalation, to the child suffering the RSV infection, of an anti-RSV polypeptide that binds F-protein of RSV with a $K_D$ of $5 \times 10^{-10}$ M or less, that neutralizes RSV with an IC90 of 90 ng/mL or less, and that comprises, consists essentially of, or consists of three anti-RSV immunoglobulin single variable domains, and a bronchodilator, wherein the polypeptide is administered to child by inhalation at an inhaled dose of 0.20-0.40 mg/kg daily, 0.20-0.35 mg/kg daily, or 0.24 mg/kg daily. In certain aspects of this method, the $K_D$ may be measured by an immunoassay. Alternatively, or in addition, in certain aspects of this method, the IC90 may be measured in a micro-neutralization assay.

Accordingly in another aspect, the invention also provides a method for the treatment of RSV infection, such as RSV lower respiratory tract infection, in a young child, said method comprising the simultaneous, separate or sequential administration by inhalation, to the child suffering the RSV lower respiratory tract infection, of an anti-RSV polypeptide that binds F-protein of RSV with a $K_D$ of $5 \times 10^{-10}$ M or less, that neutralizes RSV with an IC90 of 90 ng/mL or less, and that comprises, consists essentially of, or consists of three anti-RSV immunoglobulin single variable domains, and a bronchodilator, wherein the polypeptide is administered to the child by inhalation at a nominal dose of 1.00-2.00 mg/kg daily, 1.00-1.75 mg/kg daily, or 1.20 mg/kg daily. In certain aspects of this method, the $K_D$ may be measured by an immunoassay. Alternatively, or in addition, in certain aspects of this method, the IC90 may be measured in a micro-neutralization assay.

In one aspect, the polypeptide is administered daily for 2 to 5 consecutive days, or more, such as daily for 2 consecutive days, for 3 consecutive days, for 4 consecutive days, for 5 consecutive days, or more, such as e.g. for 3 consecutive days.

The bronchodilator preferably belongs to the class of beta2-mimetics or to the class of anticholinergics. In one aspect, the bronchodilator is a long-acting beta2-mimetic such as e.g. formoterol or a solvate thereof, salmeterol or a salt thereof, or a mixture thereof. In another aspect, the bronchodilator is a short-acting beta2-mimetic such as e.g. salbutamol, terbutaline, pirbuterol, fenoterol, tulobuterol, levosabutamol, or a mixture thereof. In another aspect, the bronchodilator is an anticholinergic such as e.g. tiotropium, oxitropium, ipratropium bromide or a mixture thereof.

The present invention also relates to a nebulizer comprising 0.150-0.400 mL of a composition comprising the polypeptide of the invention at a concentration of 50 mg/mL. In one aspect, the nebulizer is a vibrating mesh nebulizer. In one aspect, the nebulizer has a fixed flow of air or oxygen. The present invention also relates to such nebulizers comprising 0.150-0.400 mL of a composition comprising the polypeptide of the invention at a concentration of 50 mg/mL, for use in the methods of the invention. Exemplary nebulizers of the invention comprise, consist essentially of, or consist of 0.150-0.400 mL of a 50 mg/mL of a composition comprising, consisting essentially of, or consisting of a polypeptide that binds F-protein of hRSV with a $K_D$ of $5 \times 10^{-10}$ M or less, that neutralizes hRSV with an IC90 of 90 ng/mL or less, and that comprises, consists essentially of, or consists of three anti-hRSV immunoglobulin single variable domains. In certain aspects of this nebulizer, the $K_D$ may be measured by an immunoassay. Alternatively, or in addition, in certain aspects of this nebulizer, the IC90 may be measured in a micro-neutralization assay.

LIST OF NUMERICAL REFERENCES USED IN THE FIGURES

Figure 1:
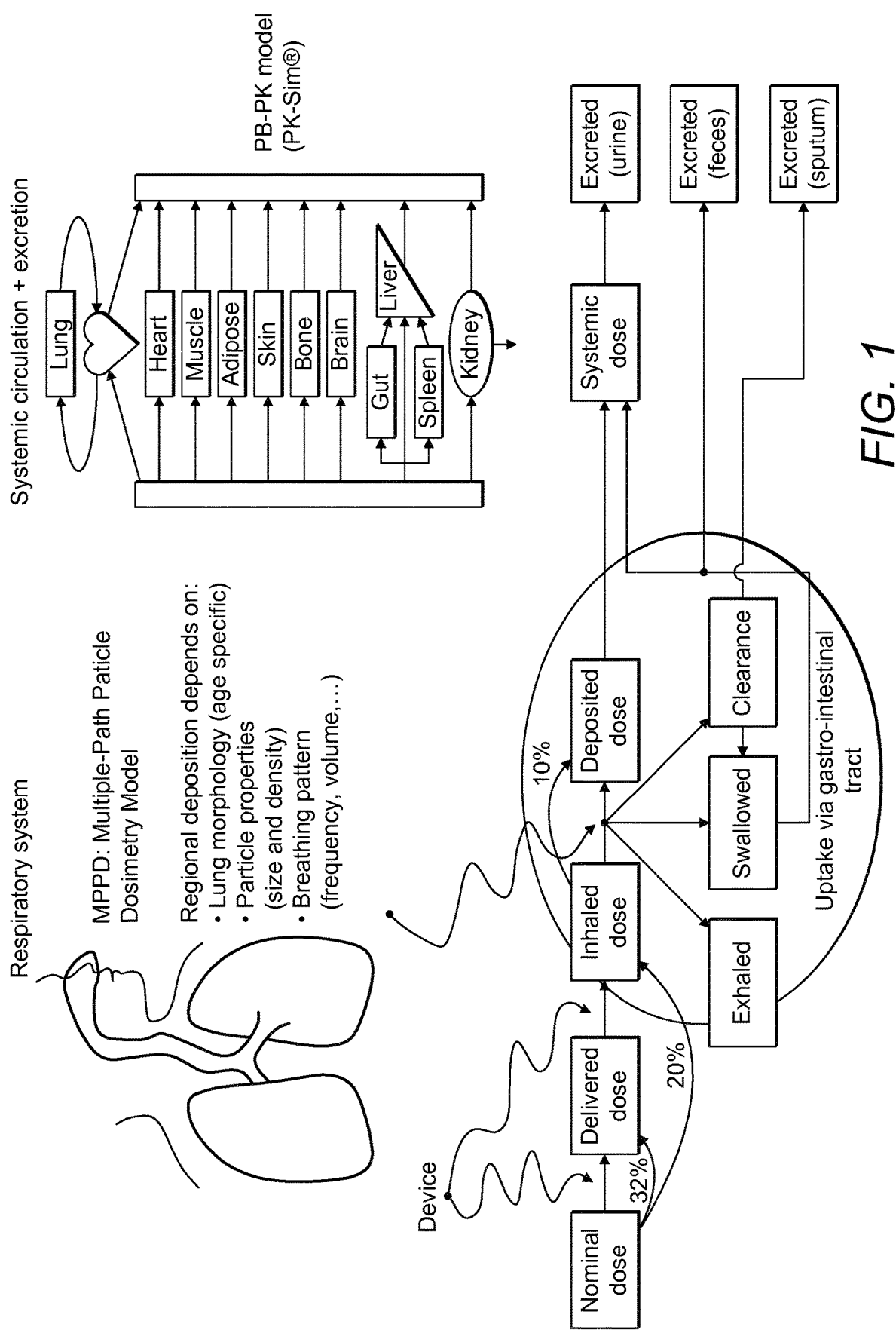
FIG. 1 is a schematic diagram depicting an overview of the modelling strategy used in the present invention. Nominal dose: amount of SEQ ID NO: 71 filled in the nebuliser; delivered dose: amount of SEQ ID NO: 71 in aerosol particles generated by the vibrating mesh nebuliser, and available in the face mask for inhalation; Inhaled dose: amount of SEQ ID NO: 71 in aerosol particles available at the upper respiratory tract (i.e., the dose which is inhaled); deposited dose: amount of SEQ ID NO: 71 in aerosol particles deposited in the lower respiratory tract; systemic dose: amount of SEQ ID NO: 71 absorbed via the alveolar lining fluid of the lower respiratory tract and released into circulation.

100 Inhalation device
101 Aerosol generator
102 Vibratable Mesh
103 Reservoir
104 Gas inlet opening
105 Face mask
106 Casing
107 Aerosol inlet opening
108 Patient contacting surface 109 Valve (one-way exhalation or two-way inhalation/exhalation valve)
110 Flow channel
111 Lateral opening
112 Switch
113 Tube fitting
114 Lid
115 Key lock
116 USB-Port
117 Holes
118 Base unit
119 Mixing channel unit
200 SAINT model
201 Face/throat portion of the SAINT model
202 Nasal portion of the SAINT model
300 Glass fibre filter assembly

DETAILED DESCRIPTION

Definitions

Unless indicated or defined otherwise, all terms used have their usual meaning in the art, which will be clear to the skilled person. Reference is for example made to the standard handbooks, such as Sambrook et al. "Molecular Cloning: A Laboratory Manual" (2nd. Ed.), Vols. 1-3, Cold Spring Harbor Laboratory Press (1989); F. Ausubel et al. eds., "Current protocols in molecular biology", Green Publishing and Wiley Interscience, New York (1987); Lewin "Genes II", John Wiley & Sons, New York, N.Y., (1985); Old et al. "Principles of Gene Manipulation: An Introduction to Genetic Engineering", 2nd edition, University of California Press, Berkeley, Calif. (1981); Roitt et al. "Immunology" (6th. Ed.), Mosby/Elsevier, Edinburgh (2001); Roitt et al. Roitt's Essential Immunology, 10th Ed. Blackwell Publishing, UK (2001); and Janeway et al. "Immunobiology" (6th Ed.), Garland Science Publishing/Churchill Livingstone, N.Y. (2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews: Presta 2006 (Adv. Drug Deliv. Rev. 58 (5-6): 640-56), Levin and Weiss 2006 (Mol. Biosyst. 2(1): 49-57), Irving et al. 2001 (J. Immunol. Methods 248(1-2): 31-45), Schmitz et al. 2000 (Placenta 21 Suppl. A: S106-12), Gonzales et al. 2005 (Tumour Biol. 26(1): 31-43), which describe techniques for protein engineering, such as affinity maturation and other techniques for improving the specificity and other desired properties of proteins such as immunoglobulins.

A nucleic acid sequence or amino acid sequence is considered to be "(in) essentially isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist(s) of" or "consist(s) essentially of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

In addition, the term "sequence" as used herein (for example in terms like "immunoglobulin sequence", "variable domain sequence", "immunoglobulin single variable domain sequence", "VHH sequence" or "protein sequence"), should generally be understood to include both the relevant amino acid sequence as well as nucleic acid sequences or nucleotide sequences encoding the same, unless the context requires a more limited interpretation.

An amino acid sequence (such as an immunoglobulin single variable domain, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of $(mol/liter)^{-1}$ (or $M^{-1}$). In the present specification, the stability of the interaction between two molecules (such as immunoglobulin single variable domain or polypeptide of the invention and F-protein of hRSV) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well-known relation $DG=RT \cdot \ln(K_D)$ (equivalently $DG=-RT \cdot \ln(K_A)$), where R equals the gas constant, T equals the absolute temperature and ln denotes the natural logarithm.

The $K_D$ for biological interactions which are considered meaningful (e.g. specific) are typically in the range of $10^{-10}M$ (0.1 nM) to $10^{-5}M$ (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units $s^{-1}$ (where s is the SI unit notation of second). The on-rate $k_{on}$ has units $M^{-1} s^{-1}$. The on-rate may vary between $10^2 M^{-1} s^{-1}$ to about $10^7 M^{-1} s^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6} s^{-1}$ (near irreversible complex with a $t_{1/2}$ of multiple days) to $1 s^{-1}$ ($t_{1/2}=0.69$ s).

Specific binding of an antigen-binding protein to an antigen or antigenic determinant can be determined in any suitable manner known per se, including, for example, Scatchard analysis and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known Biacore instruments (Pharmacia Biosensor AB, Uppsala, Sweden). Kinetic Exclusion Assay (KinExA) (Drake et al. 2004, Analytical Biochemistry 328: 35-43) measures binding events in solution without labeling of the binding partners and is based upon kinetically excluding the dissociation of a complex.

The GYROLAB™ immunoassay system provides a platform for automated bioanalysis and rapid sample turnaround (Fraley et al. 2013, Bioanalysis 5: 1765-74).

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

The term "infectivity of a virus", as used herein, refers to the proportion of living subjects that, when exposed to said virus, actually become infected by said virus.

"Neutralization of a virus", as used herein, refers to the modulation and/or reduction and/or prevention and/or inhibition of the infectivity (as defined herein) of a virus by binding of a neutralizing compound to the virion, as measured using a suitable in vitro, cellular or in vivo assay (such as those mentioned further).

The term "dose" refers to an amount of polypeptide of the invention that is administered to the subject.

The "nominal dose" refers to the amount of polypeptide of the invention filled in the nebuliser. The nominal dose can easily be determined based on the fill volume (volume of therapeutic composition filled in the nebulizer) and the concentration of the polypeptide of the invention in the therapeutic composition.

The "delivered dose" refers to the amount of polypeptide of the invention in aerosol particles generated by the vibrating mesh nebuliser and available in the face mask for inhalation.

The "inhaled dose" refers to the amount of polypeptide of the invention in aerosol particles available at the upper respiratory tract (i.e., the dose which is inhaled). The inhaled dose can be calculated as a percentage (%) from the nominal dose and will depend on the characteristics of the nebulizer. Inhaled doses usually vary between 10% and 20% or more of the filled dose.

The inhaled dose can, for example, be determined using an airway model of the upper airways of a young child. Such a model is, e.g., the Sophia anatomical infant nose throat (SAINT) model (Janssens et al. 2001, J. Aerosol Med. 14:433-41). The SAINT model is an anatomically correct cast/representation of the upper airways of a 9 month old child, built using stereolithographic techniques and used for studying aerosol deposition in young children. The administration conditions that apply in the method of the present invention can be closely mimicked. Administration with the FOX nebulizer, for example, showed that, from the total dose filled in to the nebulizer, approximately 20% is expected to be inhaled.

The "deposited dose" refers to the amount of polypeptide of the invention in aerosol particles deposited in the lower respiratory tract. The deposited dose can be calculated from the inhaled dose and will depend on the characteristics of the inhaled particles and the breathing pattern of the young child suffering RSV infection. Breathing patterns in RSV infected children are e.g. described by Amirav et al. 2002 (J. Nucl.

Med. 43: 487-91), Amirav et al. 2012 (Arch. Dis. Child 97: 497-501), Chua et al. 1994 (Eur. Respir. J. 7: 2185-91), Fok et al. 1996 (Pediatr. Pulmonol. 21: 301-9), Wildhaber et al. 1999 (J. Pediatr. 135: 28-33), Totapally et al. 2002 (Crit. Care 6: 160-5), Mundt et al. 2012 (Pediatr. 2012: 721295).

The deposited dose should best be determined using modeling, taking into account lung morphology (age specific), particle properties (size and density), as well as breathing pattern (frequency, volume). A model that takes into account these parameters is e.g. the Multiple-Path Particle Dosimetry (MPPD). The MPPD tool is an age specific symmetric lung model, developed by the NIH Centre for Information Technology (CIT, US) and the National Institute of Public Health and the Environment (RIVM, the Netherlands), and can be used to calculate deposition of aerosols in the respiratory tract. It allows the description of the average regional depositions in the head, tracheobronchial and alveolar regions, and average deposition per airway generation, for different paediatric age groups, and for particles of different sizes. Overall, regional deposition depends on lung morphology (which is age specific), particle properties (size and density distribution) and breathing pattern (frequency, volume). For a quiet nasal inhalation by the RSV infected children and a particle MAD (mass median diameter) of 2.63 micrometer, the fraction deposited in the alveolar space was calculated to be around 10% of the inhaled dose.

The "systemic dose" refers to the amount of polypeptide of the invention absorbed via the alveolar lining fluid of the lower respiratory tract and released into circulation. The systemic dose can easily be determined by measuring the concentration of the polypeptide of the invention in the systemic circulation.

The "systemic circulation" as used in the present invention, is the part of the cardiovascular system which carries oxygenated blood away from the heart to the body, and returns deoxygenated blood back to the heart.

The term "dosing" refers to the administration of the polypeptide of the invention. Unless explicitly indicated different, in the context of the present invention, the term "dosing" refers to the pulmonary administration of the polypeptide of the invention.

A child is generally a human subject between birth and puberty or in the developmental stage of childhood. In the context of the present invention, a "young child" refers to a child of less than 24 months or less than 36 months (3 years). An "infant" is the very young offspring of a human. The term is usually considered synonymous with baby. The term "infant" is typically applied to young children between the ages of 1 month and 12 months. When a human child learns to walk, the term "toddler" may be used instead. A "toddler" is a child between the ages of one and three. In the context of the present invention, a "toddler" is a child between the ages of one and less than 24 months or between the ages of one and less than 36 months (3 years).

"Pediatrics" is the branch of medicine that deals with the medical care of infants and children.

"Respiratory tract" is for the purposes of this invention equivalent with "respiratory system", "airway tissue" or "airways". The respiratory system comprises 2 distinct zones: a conducting and a respiratory zone, within which the airway and vascular compartments lie (see e.g. "Pulmonary Drug Delivery", Edited by Karoline Bechtold-Peters and Henrik Luessen, 2007, ISBN 978-3-87193-322-6 pages 16-28). The conducting zone consists of the nose, pharynx, larynx, trachea, bronchi, and bronchioles. These structures form a continuous passageway for air to move in and out of the lungs. The respiratory zone is found deep inside the lungs and is made up of the respiratory bronchioles, alveolar ducts, and alveoli. These thin-walled structures allow inhaled oxygen to diffuse into lung capillaries in exchange for carbon dioxide. Anatomically, the same structures are often divided into the upper and the lower respiratory tracts. The upper respiratory structures are found in the head and neck and consist of the nose, pharynx, and larynx. The lower respiratory tract structures are located in the thorax or chest and include the trachea, bronchi, and lungs (i.e. bronchioles, alveolar ducts, and alveoli). The lower respiratory tract thus refers to the portions of the airways from the trachea to the lungs.

An "alveolus" (plural: "alveoli") is an anatomical structure that has the form of a hollow cavity. Found in the lung parenchyma, the pulmonary alveoli are the terminal ends of the respiratory tree, which outcrop from either alveolar sacs or alveolar ducts, which are both sites of gas exchange with the blood as well. The alveolar membrane is the gas-exchange surface. Carbon dioxide rich blood is pumped from the rest of the body into the alveolar blood vessels where, through diffusion, it releases its carbon dioxide and absorbs oxygen.

The "alveolar lining fluid (ALF)" forms a thin fluid layer that covers the mucosa of the alveoli, the small airways, and the large airways. It constitutes the first barrier between the lung and the outer world. In the context of the present invention this term refers to the deeper lung.

Bronchoalveolar lavage (BAL) is a medical procedure in which a bronchoscope is passed through the mouth or nose into the lungs and fluid is squirted into a small part of the lung and then collected for examination. BAL is the most common manner to sample the components of the alveolar lining fluid (ALF).

"Administration by inhalation", "pulmonary administration", "delivery by inhalation", and "pulmonary delivery" as used in the present invention means that the polypeptide of the invention is administered to the respiratory tract. In the present invention, in this delivery method, the polypeptide of the invention is present in an aerosol obtained from nebulizing (with a nebulizer) the polypeptide of the invention.

An "inhalation device" is a medical device used for delivering medication into the body via the lungs/

An "aerosol" as used herein refers to a suspension of liquid in the form of fine particles dispersed in a gas (i.e. a fine mist or spray containing minute particles). As used herein, the term "particle" refers to liquids, e.g., droplets. Pharmaceutical aerosols for the delivery of the polypeptides of the invention to the lungs can be inhaled via the mouth and/or via the nose. In pulmonary delivery, the generation of particles smaller than approximately 5 or 6 micrometer is considered necessary to achieve deposition as the fine particle fraction (FPF) (i.e. in the respiratory bronchioles and alveolar region) (O'Callaghan and Barry, 1997, Thorax 52: S31-S44). The particle size in an aerosol can be expressed as volume median diameter (VMD). The "volume median diameter" is defined as the geometric particle diameter of an aerosol, where 50% of the aerosol volume is larger than this value and 50% is smaller than this value. "Mass median aerodynamic diameter (MMAD)" is defined as the geometric mean aerodynamic diameter, where 50% of the particles by weight will be smaller than this value and 50% will be larger than this value. When the density of the aerosol particles is 1 g/cm$^3$, the VMD and MMAD are equivalent.

The term "nebulization" as used in the present invention refers to the conversion of a liquid into a mist or fine spray by a nebulizer (as further defined herein).

An "aerosol generator" is a device or device component capable of generating an aerosol from a liquid formulation; e.g. a pharmaceutical composition for inhalation use. Synonymously, the terms "nebulizer" or "nebulising means" may be employed.

Unless specified otherwise, a "gas" refers to any gas or mixture of gases suitable for inhalation.

"Lateral", or "laterally", means away from the middle, centre, or centre axis of a device or device component.

As used herein, the terms "subject" and "patient" are used interchangeably. As used herein, the terms "subject" and "subjects" refer to a human.

The phrase "pharmaceutically acceptable" as used herein means approved by a regulatory agency of the Federal or a state government, or listed in the U.S. Pharmacopeia, European Pharmacopoeia or other generally recognized pharmacopeia for use in animals, and more particularly in humans. In this sense, it should be compatible with the other ingredients of the formulation and not eliciting an unacceptable deleterious effect in the subject. It refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically active amount" refers to the amount of a therapeutic agent (e.g. a polypeptide of the invention), that is sufficient to reduce the severity and/or duration of one or more diseases and/or disorders.

Polypeptide of the Invention

Polypeptides of the invention may be non-naturally occurring. Thus, the polypeptides of the invention may have been designed, manufactured, synthesized, and/or recombined to produce a non-naturally occurring sequence.

Immunoglobulin Single Variable Domain

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single $V_H$ or $V_L$ domain. Hence, the antigen binding site of an immunoglobulin single variable domain is formed by no more than three CDRs.

The term "immunoglobulin single variable domain" and "single variable domain" hence does not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

In one embodiment of the invention, the immunoglobulin single variable domains are light chain variable domain sequences (e.g. a $V_L$-sequence), or heavy chain variable domain sequences (e.g. a $V_H$-sequence); more specifically, the immunoglobulin single variable domains can be heavy chain variable domain sequences that are derived from a conventional four-chain antibody or heavy chain variable domain sequences that are derived from a heavy chain antibody.

For example, the single variable domain or immunoglobulin single variable domain (or an amino acid that is suitable for use as an immunoglobulin single variable domain) may be a (single) domain antibody (or an amino acid that is suitable for use as a (single) domain antibody), a "dAb" or dAb (or an amino acid that is suitable for use as a dAb) or a Nanobody (as defined herein, and including but not limited to a $V_{HH}$); other single variable domains, or any suitable fragment of any one thereof.

For a general description of (single) domain antibodies, reference is also made to the prior art cited herein, as well as to EP 0368684. For the term "dAb's", reference is for example made to Ward et al. 1989 (Nature 341: 544-546), to Holt et al. 2003 (Trends Biotechnol. 21: 484-490); as well as to for example WO 04/068820, WO 06/030220, WO 06/003388, WO 06/059108, WO 07/049017, WO 07/085815 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the immunoglobulin single variable domain may be a Nanobody® (as defined herein) or a suitable fragment thereof. [Note: Nanobody® Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

For a further description of $V_{HH}$'s and Nanobodies, reference is made to the review article by Muyldermans 2001 (Reviews in Molecular Biotechnology 74: 277-302), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g. described in Davies and Riechmann 1994 (FEBS 339: 285-290), 1995 (Biotechonol. 13: 475-479), 1996 (Prot. Eng. 9: 531-537) and Riechmann and Muyldermans 1999 (J. Immunol. Methods 231: 25-38).

The term "immunoglobulin single variable domain" encompasses immunoglobulin sequences of different origin, comprising mouse, rat, rabbit, donkey, human and camelid immunoglobulin sequences. It also includes fully human, humanized or chimeric immunoglobulin sequences. For example, it comprises camelid immunoglobulin sequences and humanized camelid immunoglobulin sequences, or camelized immunoglobulin single variable domains, e.g. camelized dAbs as described by Ward et al. 1989 (see for example WO 94/04678 and Davies and Riechmann 1994, 1995 and 1996) and camelized VH.

Again, such immunoglobulin single variable domains may be derived in any suitable manner and from any suitable source, and may for example be naturally occurring $V_{HH}$ sequences (i.e. from a suitable species of Camelid) or synthetic or semi-synthetic amino acid sequences, including but not limited to partially or fully "humanized" $V_{HH}$, "camelized" immunoglobulin sequences (and in particular camelized $V_H$), as well as Nanobodies and/or $V_{HH}$ that have been obtained by techniques such as affinity maturation (for example, starting from synthetic, random or naturally occurring immunoglobulin sequences, such as $V_{HH}$ sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

The total number of amino acid residues in an immunoglobulin single variable domain can be in the region of 110-120, is preferably 112-115, and is most preferably 113 (although it will be clear, based on the examples of immunoglobulin single variable domain sequences that are given herein as well as in WO 08/020079, in WO 06/040153 and in the further immunoglobulin single variable domain-related references cited therein, that the precise number of amino acid residues will also depend on the length of the specific CDR's that are present in the immunoglobulin single variable domain).

The amino acid sequence and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

As further described in paragraph q) on pages 58 and 59 of WO 08/020079 (incorporated herein by reference), the amino acid residues of an immunoglobulin single variable domain are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans 2000 (J. Immunol. Methods 240: 185-195; see for example FIG. 2 of this publication), and accordingly FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

In the method of the present invention, the immunoglobulin single variable domain binds F-protein of hRSV and is therefore also referred to as "anti-hRSV immunoglobulin single variable domain" or "anti-hRSV immunoglobulin single variable domain of the invention". More in particular, the anti-hRSV immunoglobulin single variable domain can bind protein F of hRSV with an affinity (suitably measured and/or expressed as a $K_D$-value (actual or apparent), a $K_A$-value (actual or apparent), a $k_{on}$-rate and/or a $k_{off}$-rate) preferably such that:

it binds to protein F of hRSV with a dissociation constant ($K_D$) of 1000 nM to 1 nM or less, preferably 100 nM to 1 nM or less, more preferably 15 nM to 1 nM or even 10 nM to 1 nM or less; and/or it binds to protein F of hRSV with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more; and/or it binds to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

In one aspect, the immunoglobulin single variable domain is capable of neutralizing hRSV. Assays to determine the neutralizing capacity of a molecule include e.g. the microneutralization assay described by Anderson et al. (1985, J. Clin. Microbiol. 22: 1050-1052; 1988, J. Virol. 62: 4232-4238), or modifications of this assay such as e.g. described in WO 2010/139808, or a plaque reduction assay as for example described by Johnson et al. (1997, J. Inf. Dis. 176: 1215-1224), and modifications thereof. For example, in a microneutralization assay on hRSV Long (such as e.g. described in WO 2010/139808; page 375, Example 6) the anti-hRSV immunoglobulin single variable domain may have IC50 values between 100 nM and 1000 nM, preferably between 100 nM and 500 nM, or less.

Combinations of CDR1, CDR2, and CDR3 sequences of preferred anti-hRSV immunoglobulin single variable domains are shown in Table A-1. In a preferred aspect, the anti-hRSV immunoglobulin single variable domain has a CDR1 which is SEQ ID NO: 46, a CDR2 which is selected from SEQ ID NOs: 49 and 50, and a CDR3 which is SEQ ID NO: 61. Most preferably CDR1 is SEQ ID NO: 46, CDR2 is SEQ ID NO: 49, and CDR3 is SEQ ID NO: 61. Table A-1 also shows preferred combinations of CDR sequences and framework sequences.

Without being limiting, advantageous immunoglobulin single variable domains for use in the polypeptide of the invention are described in WO 2010/139808. Preferably, the anti-h RSV immunoglobulin single variable domain is selected from any of SEQ ID NOs: 1-34 in Table A-2.

Polypeptide of the Invention

The immunoglobulin single variable domains for use in the method of the invention may form part of a polypeptide (referred herein as "polypeptide of the invention"), which may comprise or (essentially) consist of one or more immunoglobulin single variable domains that specifically bind F-protein of hRSV and which may optionally further comprise one or more further amino acid sequences (all optionally linked via one or more suitable linkers). The term "immunoglobulin single variable domain" may also encompass such polypeptide of the invention. For example, and without limitation, the one or more immunoglobulin single variable domains may be used as a binding unit in such a polypeptide, which may optionally contain one or more further amino acid sequences that can serve as a binding unit, so as to provide a monovalent, multivalent or multispecific polypeptide of the invention, respectively (for multivalent and multispecific polypeptides containing one or more VHH domains and their preparation, reference is also made to Conrath et al. 2001 (J. Biol. Chem. 276: 7346-7350), as well as to for example WO 96/34103, WO 99/23221 and WO 2010/115998).

Preferably, the polypeptides of the invention encompass constructs comprising three or more antigen binding units in the form of single variable domains, as outlined above. For example, three or more immunoglobulin single variable domains that bind hRSV (also referred to herein as "anti-hRSV immunoglobulin single variable domain(s)") can be linked to form a trivalent or multivalent construct. Preferably the polypeptide of the invention consists of three anti-hRSV immunoglobulin single variable domains.

In the polypeptides described above, the three or more anti-hRSV immunoglobulin single variable domains may be linked directly to each other and/or via one or more suitable linkers or spacers. Suitable spacers or linkers for use in multivalent polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each immunoglobulin single variable domain by itself forms a complete antigen-binding site).

For example, a linker may be a suitable amino acid sequence, and in particular amino acid sequences of between 1 and 50, preferably between 1 and 30, such as between 1 and 20 or between 1 and 10 amino acid residues. Widely used peptide linkers comprise Gly-Ser repeats, e.g. (Gly)4-Ser in one, two, three, four, five, six or more repeats, or for example of the type $(gly_xser_y)_z$, such as (for example $(gly_4ser)_3$ or $(gly_3ser_2)_3$, as described in WO 99/42077, or hinge-like regions such as the hinge regions of naturally occurring heavy chain antibodies or similar sequences (such as described in WO 94/04678). Some other particularly preferred linkers are poly-alanine (such as AAA), as well as the linkers mentioned in Table A-4.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

In one aspect, the polypeptide of the invention binds F-protein of hRSV. More in particular, the polypeptide of the invention can bind protein F of hRSV with an affinity (suitably measured and/or expressed as a $K_D$-value (actual or apparent), a $K_A$-value (actual or apparent), a $k_{on}$-rate and/or a $k_{off}$-rate) preferably such that:

it binds to protein F of hRSV with a dissociation constant ($K_D$) of 100 nM to 0.1 nM or less, preferably 10 nM to 0.1 nM or less, more preferably 1 nM to 0.1 nM or less, such as e.g. $5\times10^{-10}$ M (0.5 nM) or less;

it binds to protein F of hRSV with a $k_{on}$ rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more; and/or it binds to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, more preferably between $5\times10^{-3}$ $s^{-1}$ and $10^{-4}$ $s^{-1}$, or lower.

In one aspect, the polypeptide of the invention is capable of neutralizing hRSV. Assays to determine the neutralizing capacity of a molecule include e.g. the microneutralization assay described by Anderson et al. (1985, J. Clin. Microbiol. 22: 1050-1052; 1988, J. Virol. 62: 4232-4238), or modifications of this assay such as e.g. described in WO 2010/139808, or a plaque reduction assay as for example described by Johnson et al. (1997, J. Inf. Dis. 176: 1215-1224), and modifications thereof. For example, in a microneutralization assay on hRSV Long (such as e.g. described in WO 2010/139808, page 375, Example 6) the polypeptides of the invention may have IC50 values between 10 pM and 1000 pM, preferably between 10 pM and 250 pM, more preferably between 50 pM and 200 pM or less. The polypeptides of the invention may have IC90 values between 1 nM and 100 nM, preferably between 1 nM and 10 nM, more preferably between 1 nM and 5 nM or less such as e.g. 2 nM or less, or 90 ng/mL or less.

In a preferred aspect, the polypeptide of the invention binds F-protein of hRSV with an affinity (suitably measured and/or expressed as a $K_D$-value (actual or apparent), as described herein) preferably such that it binds to protein F of hRSV with a dissociation constant ($K_D$) of 100 nM to 0.1 nM or less, preferably 10 nM to 0.1 nM or less, more preferably 1 nM to 0.1 nM or less, such as e.g. $5\times10^{-10}$ M (0.5 nM) or less; and in addition, the polypeptides of the invention is capable of neutralizing hRSV with IC50 values between 10 pM and 1000 pM, preferably between 10 pM and 250 pM, more preferably between 50 pM and 200 pM or less, or with IC90 values between 1 nM and 100 nM, preferably between 1 nM and 10 nM, more preferably between 1 nM and 5 nM or less such as e.g. 2 nM or less, or 90 ng/mL or less. In one aspect, the polypeptide of the invention binds F-protein of hRSV with an affinity of $5\times10^{-10}$ M (0.5 nM) or less and neutralizes hRSV with an IC50 value of 90 ng/mM or less.

In a specific aspect, the multivalent (such as trivalent) polypeptide of the invention may comprise or essentially consist of at least three anti-hRSV immunoglobulin single variable domains selected from any of SEQ ID NOs: 1-34 (Table A-2). Without being limiting, advantageous polypeptides for use in the method of the invention are described in WO 2010/139808. Preferably the polypeptide of the invention is selected from any of SEQ ID NOs: 65-85 (Table B-2), preferably SEQ ID NO: 71.

SEQ ID NO: 71 is a trivalent polypeptide consisting of three anti-hRSV immunoglobulin variable domains derived from heavy chain-only llama antibodies. Each of the three anti-hRSV immunoglobulin single variable domains binds to F-protein of hRSV.

The polypeptides of the invention may be produced by a method comprising the following steps:
a) expressing, in a suitable host cell or host organism or in another suitable expression system, a nucleic acid or nucleotide sequence, or a genetic construct encoding the polypeptide of the invention;

optionally followed by:
b) isolating and/or purifying the polypeptide of the invention thus obtained.

The method for producing the polypeptide of the invention may comprise the steps of:
a) cultivating and/or maintaining a host or host cell under conditions that are such that said host or host cell expresses and/or produces at least one polypeptide of the invention, optionally followed by:
b) isolating and/or purifying the polypeptide of the invention thus obtained.

According to one preferred, but non-limiting embodiment of the invention, the polypeptide of the invention is produced in a bacterial cell, in particular a bacterial cell suitable for large scale pharmaceutical production.

According to another preferred, but non-limiting embodiment of the invention, the polypeptide of the invention is produced in a yeast cell, in particular a yeast cell suitable for large scale pharmaceutical production.

According to yet another preferred, but non-limiting embodiment of the invention, the polypeptide of the invention is produced in a mammalian cell, in particular in a human cell or in a cell of a human cell line, and more in particular in a human cell or in a cell of a human cell line that is suitable for large scale pharmaceutical production.

For production on industrial scale, preferred heterologous hosts for the (industrial) production of immunoglobulin single variable domains or immunoglobulin single variable domain-containing protein therapeutics include strains of *E. coli*, *Pichia pastoris*, *S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

Subsequently, the polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the amino acid sequence to be isolated).

METHOD OF THE INVENTION

The present invention provides methods and dosing schedules for pulmonary administration to young children of the polypeptides of the invention. As such, these methods and dosing schedules can be used for the treatment (as defined herein) of RSV infection in these young children.

RSV infection includes the mild upper respiratory tract illness, as well as the more severe lower respiratory tract infections (LRTIs). RSV lower respiratory tract infection may include bronchiolitis and broncho-pneumonia, possibly showing typical clinical signs and symptoms such as tachypnoea, wheezing, cough, crackles, use of accessory muscles, and/or nasal flaring.

RSV infection may also include diseases and/or disorders associated with RSV infection. Examples of such diseases and/or disorders associated with hRSV infection will be clear to the skilled person, and for example include the following diseases and/or disorders: respiratory illness, upper respiratory tract infection, lower respiratory tract infection, bronchiolitis (inflammation of the small airways in the lung), pneumonia, dyspnea, cough, (recurrent) wheezing and (exacerbations of) asthma or COPD (chronic obstructive pulmonary disease) associated with hRSV.

Accordingly, the present invention also provides methods and dosing schedules for the treatment of respiratory illness, upper respiratory tract infection, lower respiratory tract infection, bronchiolitis (inflammation of the small airways in the lung), pneumonia, dyspnea, cough, (recurrent) wheezing and/or (exacerbations of) asthma or COPD (chronic obstructive pulmonary disease) associated with hRSV.

In the context of the present invention, the term "treatment" not only comprises treating the disease, but also generally comprises slowing or reversing the progress of disease, slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The method of the invention provides for the delivery of the polypeptide of the invention to the respiratory tract and, more specifically, to the lower respiratory tract of a subject. Methods for delivery to the respiratory tract and/or delivery by inhalation are known to the skilled person and are e.g. described in the handbook "Drug Delivery: Principles and Applications" (2005) by Binghe Wang, Teruna Siahaan and Richard Soltero (Eds. Wiley Interscience (John Wiley & Sons)); in "Pharmacology PreTest™ ($11^{th}$ Ed.) Self-Assessment and Review" by Rosenfeld G. C., Loose-Mitchell D. S.; and in "Pharmacology" ($3^{rd}$ Edition) by Lippincott Williams & Wilkins, New York; Shlafer M. McGraw-Hill Medical Publishing Division, New York; Yang K. Y., Graff L. R., Caughey A. B. Blueprints Pharmacology, Blackwell Publishing. In the method of the present invention, the polypeptide of the invention is delivered in an inhalable form. More particularly, the inhalable form is an aerosol obtained by nebulizing (with a nebulizer) the polypeptide of the invention.

The subject to be treated is a human, more particularly a young child. As will be clear to the skilled person, the subject to be treated will in particular be a young child suffering from RSV infection. For example, the subject may be a young child suffering from RSV infection, such as RSV lower respiratory tract infection.

In one aspect, the subject is a young child aged less than 24 months or less than 36 months (3 years). In one aspect, the subject is a young child aged 5 months to less than 24 months (such as e.g. 5 months to 23 months). In one aspect, the subject is an infant. In one aspect, the subject is a toddler.

In one aspect, the subject is a young child who is diagnosed with RSV infection (e.g. RSV lower respiratory tract infection, such as bronchiolitis or broncho-pneumonia). In one aspect, the subject is a young child aged less than 24 months or less than 36 months (3 years) who is diagnosed with RSV infection (e.g. RSV lower respiratory tract infection, such as bronchiolitis or broncho-pneumonia). In one aspect, the subject is a young child aged 5 months to less than 24 months (such as e.g. 5 months to 23 months), aged 5 months to less than 36 months (such as e.g. 5 months to 35 months), aged 1 month to less than 24 months (such as e.g. 1 month to 23 months), or aged 1 month to less than 36 months (such as e.g. 1 month to 35 months) who is diagnosed with RSV infection (e.g. RSV lower respiratory tract infection, such as bronchiolitis or broncho-pneumonia). In one aspect, the subject is an infant who is diagnosed with RSV infection (e.g. RSV lower respiratory tract infection, such as bronchiolitis or broncho-pneumonia). In one aspect, the subject is a toddler who is diagnosed with RSV infection (e.g. RSV lower respiratory tract infection, such as bronchiolitis or broncho-pneumonia).

In one aspect, the subject is a young child who is diagnosed with RSV infection (e.g. RSV lower respiratory tract infection, such as bronchiolitis or broncho-pneumonia), but is otherwise healthy. In one aspect, the subject is a young child aged less than 24 months or less than 36 months (3 years) who is diagnosed with RSV infection (e.g. RSV lower respiratory tract infection, such as bronchiolitis or broncho-pneumonia), but is otherwise healthy. In one aspect, the subject is a young child aged 5 months to less than 24 months (such as e.g. 5 months to 23 months), aged 5 months to less than 36 months (such as e.g. 5 months to 35 months), aged 1 month to less than 24 months (such as e.g. 1 month to 23 months), or aged 1 month to less than 36 months (such as e.g. 1 month to 35 months) who is diagnosed with RSV infection (e.g. RSV lower respiratory tract infection, such as bronchiolitis or broncho-pneumonia), but is otherwise healthy. In one aspect, the subject is an infant who is diagnosed with RSV infection (e.g. RSV lower respiratory tract infection, such as bronchiolitis or broncho-pneumonia), but is otherwise healthy. In one aspect, the subject is a toddler who is diagnosed with RSV infection (e.g. RSV lower respiratory tract infection, such as bronchiolitis or broncho-pneumonia), but is otherwise healthy.

In one aspect, the subject is a young child who is hospitalised for RSV infection (e.g. RSV lower respiratory tract infection, such as bronchiolitis or broncho-pneumonia). In one aspect, the subject is a young child aged less than 24 months or less than 36 months (3 years) who is hospitalised for RSV infection (e.g. RSV lower respiratory tract infection, such as bronchiolitis or broncho-pneumonia). In one aspect, the subject is a young child aged 5 months to less than 24 months (such as e.g. 5 months to 23 months), aged 5 months to less than 36 months (such as e.g. 5 months to 35 months), aged 1 month to less than 24 months (such as e.g. 1 month to 23 months), or aged 1 month to less than 36 months (such as e.g. 1 month to 35 months) who is hospitalised for RSV infection (e.g. RSV lower respiratory tract infection, such as bronchiolitis or broncho-pneumonia). In one aspect, the subject is an infant who is hospitalised for RSV infection (e.g. RSV lower respiratory tract infection, such as bronchiolitis or broncho-pneumonia). In one aspect, the subject is a toddler who is hospitalised for RSV infection (e.g. RSV lower respiratory tract infection, such as bronchiolitis or broncho-pneumonia).

In one aspect, the subject is a young child who is hospitalised for and diagnosed with RSV infection (e.g. RSV lower respiratory tract infection, such as bronchiolitis or broncho-pneumonia). In one aspect, the subject is a young child aged less than 24 months or less than 36 months (3 years) who is hospitalised for and diagnosed with RSV infection (e.g. RSV lower respiratory tract infection, such as bronchiolitis or broncho-pneumonia). In one aspect, the subject is a young child aged 5 months to less than 24 months (such as e.g. 5 months to 23 months), aged 5 months to less than 36 months (such as e.g. 5 months to 35 months), aged 1 month to less than 24 months (such as e.g. 1 month to 23 months), or aged 1 month to less than 36 months (such as e.g. 1 month to 35 months) who is hospitalised for and diagnosed with RSV infection (e.g. RSV lower respiratory tract infection, such as bronchiolitis or broncho-pneumonia). In one aspect, the subject is an infant who is hospitalised for and diagnosed with RSV infection (e.g. RSV lower respiratory tract infection, such as bronchiolitis or broncho-pneumonia). In one aspect, the subject is a toddler who is hospitalised for and diagnosed with RSV infection (e.g. RSV lower respiratory tract infection, such as bronchiolitis or broncho-pneumonia).

In one aspect, the subject is a young child who is hospitalised for and diagnosed with RSV infection (e.g. RSV lower respiratory tract infection, such as bronchiolitis or broncho-pneumonia,) but is otherwise healthy. In one aspect, the subject is a young child aged less than 24 months or less than 36 months (3 years) who is hospitalised for and diagnosed with RSV infection (e.g. RSV lower respiratory tract infection, such as bronchiolitis or broncho-pneumonia), but is otherwise healthy. In one aspect, the subject is a young child aged 5 months to less than 24 months (such as e.g. 5 months to 23 months), aged 5 months to less than 36 months (such as e.g. 5 months to 35 months), aged 1 month to less than 24 months (such as e.g. 1 month to 23 months), or aged 1 month to less than 36 months (such as e.g. 1 month to 35 months) who is hospitalised for and diagnosed with RSV infection (e.g. RSV lower respiratory tract infection, such as bronchiolitis or broncho-pneumonia), but is otherwise healthy. In one aspect, the subject is an infant who is hospitalised for and diagnosed with infection (e.g. RSV lower respiratory tract infection, such as bronchiolitis or broncho-pneumonia), but is otherwise healthy. In one aspect, the subject is a toddler who is hospitalised for and diagnosed with RSV infection (e.g. RSV lower respiratory tract infection, such as bronchiolitis or broncho-pneumonia), but is otherwise healthy.

In the method of the present invention the polypeptide of the invention, such as SEQ ID NO: 71, is administered by inhalation to subjects suffering RSV infection, such as RSV lower respiratory tract infection, at the selected dosing schedules such that treatment occurs.

The activity of the polypeptide of the invention can be assessed by measuring the reduction in viral load during the treatment. The viral load can, e.g. be determined in nose mucus of the young child. Mucus can be removed from the nose e.g. by nasal suction with a nasal aspirator, a rubber bulb syringe or a nasal swab. The viral load can be determined by any method known in the art, such as e.g. polymerase chain reaction, or culturing.

The activity of the polypeptide of the invention can also be assessed by measuring certain biomarkers in serum such as e.g. IL-8 and KL-6.

Interleukin-8 (IL-8) is an important mediator of host response to injury and infection. IL-8 levels in serum can be measured by any method known per se using techniques known to the skilled person, such as e.g. following commercially available assays: the Human IL-8 ELISA Kit (Life Technologies; Cat# KHC0081), the Human IL-8 ELISA Kits (Thermo Fisher Scientific Inc.; Cat# EH2IL8, EH2IL82, EH2IL85), or the AlphaLISA IL8 Immunoassay Research kit (PerkinElmer Inc.; Cat# AL224C, AL224F).

Kerbs von Lungren 6 antigen (KL-6) is a high-molecular-weight glycoprotein, expressed on the surface of alveolar type II cells. Serum levels of KL-6 are elevated in a variety of interstitial lung diseases that are characterized by alveolar epithelial cell damage. Serum KL-6 has been associated with the severity of RSV bronchiolitis and it was suggested that it may be a useful biomarker for the severity of RSV bronchiolitis (Kawasaki et al. 2009, J. Med. Virol. 81: 2104-8). KL-6 levels in serum can be measured by any method known per se using techniques known to the skilled person, such as e.g. following commercially available assays: the KL-6 Human ELISA (BioVendor; Cat# RSCYK243882R), the Krebs Von den Lungen 6 Immunoassay Kit (BIOTREND Chemikalien GmbH; Cat# E05k0061), or the KL-6 ELISA kit (Biorbyt; Cat# orb153677).

Following assessments can be performed to evaluate clinical activity of the polypeptide of the invention: heart rate and peripheral capillary $O_2$ saturation ($SpO_2$) levels; feeding: (type of feeding support, sufficiency of feeding), with particular attention to hydration and breathing comfort during feeding; respiratory rate; wheezing (during expiration/inspiration); crackles/crepitations during lung auscultation; daytime coughing; (sleep disturbance from) night-time coughing; (respiratory muscle) retractions (supraclavicular, intercostal, and subcostal); general appearance (activity, irritation, interest in environment, and responsiveness); and duration of hospitalization.

Based on the clinical activity parameters, additional scores such as Clinical response, Respiratory Distress Assessment Instrument (RDAI) score and Respiratory Assessment Change Score (RACS) can be calculated.

The polypeptide of the invention inhibits an early event in the viral life cycle, preventing extracellular virus from infecting virus-naïve cells by inhibiting fusion of the virion to the target cell. The methods and dosing schedules of the invention are used for inhibiting these early events in the viral life cycle and preventing extracellular virus from infecting virus-naïve cells by inhibiting fusion of the virion to the target cell.

In neutralisation assays (in Hep-2 cell cultures, as further described herein) the in vitro concentration of 90 ng/mL was determined as the concentration at which the polypeptide of the invention reaches 90% of their maximal inhibitory antiviral effect ($IC_{90}$). Subsequently, the $IC_{90}$ determined in vitro was multiplied by 100, to account for unknown and difficult to assess variables, since (i) the rate of replication of RSV in Hep-2 cell culture may not fully reflect the in vivo situation, (ii) infectivity and replication rate of the wide variety of clinical strains may vary considerably, and (iii) although a number (n=6) of clinical virus strains have been assessed for their sensitivity to the inhibitory action of the polypeptide of the invention, they may not represent the full spectrum of clinical strains.

The resulting value (9 microgram/mL or more) was considered the target concentration that would be required in the lower respiratory tract to result in clinically meaningful reduction of RSV infectivity. This concentration was calculated to be sufficient to completely saturate all target available at peak viral titres in an RSV-infected infant, and is also supported by the local target concentrations that showed efficacy in nonclinical studies in RSV-infected neonatal lambs and cotton rats. Accordingly, the present invention relates to a method for the treatment of RSV infection, such as RSV lower respiratory tract infection, in a young child, said method comprising the administration to the child suffering the RSV infection, of a polypeptide of the invention, wherein the polypeptide is administered to the child by inhalation at a target concentration of 9 microgram/mL (wherein this value is understood to optionally encompass a range of ±0.5 microgram/mL) or more. The invention also relates to a polypeptide of the invention for use in treatment of RSV infection, such as RSV lower respiratory tract infection, in a young child, wherein the polypeptide is administered to the child suffering RSV infection by inhalation at a target concentration of 9 microgram/mL (wherein this value is understood to optionally encompass a range of ±0.5 microgram/mL) or more.

In the present invention, a paediatric model was developed (see FIG. 1) to provide guidance on appropriate dosing regimens, and predict local and systemic PK indices for the polypeptide of the invention, as well as their associated variability. The main goal was to ensure concentration values ($C_{trough}$) above the estimated target concentration in the lower respiratory tract (9 µg/mL), taking into account growth and developmental processes such as organ maturation, changes in blood flow, body composition, and ontogeny of elimination mechanisms. The paediatric model was developed via multi-step scaling, initially using nonclinical data, later using predicted and measured clinical PK parameters of the polypeptide of the invention in adults, and subsequent extrapolation to children by scaling (i) anatomical and physiological parameters, (ii) the clearance processes, and (iii) the absorption process.

The developed paediatric model was used to estimate the required dose to reach and maintain a local concentration equal to or above the estimated target concentration in 95% of individuals throughout the treatment period. Based on simulations with this paediatric model, the deposited dose that would need to be present in the lower respiratory tract after one administration was 0.024 mg polypeptide of the invention per kg body weight. Accordingly, the present invention relates to a method for the treatment of RSV infection, such as RSV lower respiratory tract infection, in a young child, said method comprising the administration to the child suffering the RSV infection, of a polypeptide of the invention, wherein the polypeptide is administered to the child by inhalation at a deposited dose of 0.020-0.040 mg/kg daily, more specifically at a deposited dose of 0.020-0.035 mg/kg daily, such as e.g. 0.024 mg/kg daily (wherein this value is understood to optionally encompass a range of ±0.002 mg/kg). The invention also relates to a polypeptide of the invention for use in treatment of RSV infection, such as RSV lower respiratory tract infection, in a young child, wherein the polypeptide is administered to the child suffering RSV infection by inhalation at a deposited dose of 0.020-0.040 mg/kg daily, more specifically at a deposited dose of 0.020-0.035 mg/kg daily, such as e.g. 0.024 mg/kg daily (wherein this value is understood to optionally encompass a range of ±0.002 mg/kg).

Further simulations showed that breathing patterns representative for RSV-infected infants and toddlers resulted in deposition of ~10% of the inhaled amount of polypeptide of the invention in the lower respiratory tract (7-13%, depending on age and particle size). Correspondingly, a dose of 0.24 mg/kg would need to be inhaled (inhaled dose) to reach a deposited dose of 0.024 mg/kg in the lower respiratory tract after one administration. Accordingly, the present invention also relates to a method for the treatment of RSV infection, such as RSV lower respiratory tract infection, in a young child, said method comprising the administration to the child suffering the RSV infection, of a polypeptide of the invention, wherein the polypeptide is administered to the child by inhalation at an inhaled dose of 0.20-0.40 mg/kg daily, more specifically at an inhaled dose of 0.20-0.35 or 0.20-0.45 mg/kg daily, such as e.g. 0.24 mg/kg daily (wherein this value is understood to optionally encompass a range of ±0.02 mg/kg). The invention also relates to a polypeptide of the invention for use in treatment of RSV infection, such as RSV lower respiratory tract infection, in a young child, wherein the polypeptide is administered to the child suffering RSV infection by inhalation at an inhaled dose of 0.20-0.40 mg/kg daily, more specifically at an inhaled dose of 0.20-0.45 or 0.20-0.45 mg/kg daily, such as e.g. 0.24 mg/kg daily (wherein this value is understood to optionally encompass a range of ±0.02 mg/kg).

Studies on aerosol deposition were done with the Sophia anatomical infant nose-throat (SAINT) model in which the polypeptide was administered with a vibrating mesh nebulizer, more specifically a vibrating mesh nebulizer with a constant flow of 2 L/min additional air or $O_2$, such as e.g. the FOX nebulizer (Janssens et al. 2001, Journal of aerosol medicine: the official journal of the International Society for Aerosols in Medicine 14: 433-41). The results showed that, from the total dose filled into the nebuliser, approximately 20% is expected to be inhaled. The nominal dose filled in the nebuliser to ensure an inhaled dose of 0.24 mg/kg would therefore be 1.2 mg/kg. Accordingly, the present invention also relates to a method for the treatment of RSV infection, such as RSV lower respiratory tract infection, in a young child, said method comprising the administration to the child suffering the RSV infection, of a polypeptide of the invention, wherein the polypeptide is administered to the child by inhalation at a nominal dose of 1.00-2.00 mg/kg daily, more specifically at a nominal dose of 1.00-1.75 mg/kg daily, such as e.g. 1.20 mg/kg daily (wherein this value is understood to optionally encompass a range of ±0.06 mg/kg). The invention also relates to a polypeptide of the invention for use in treatment of RSV infection, such as RSV lower respiratory tract infection, in a young child, wherein the polypeptide is administered to the child suffering RSV infection by inhalation at a nominal dose of 1.00-2.00 mg/kg daily, more specifically at a nominal dose of 1.00-1.75 mg/kg daily, such as e.g. 1.20 mg/kg daily (wherein this value is understood to optionally encompass a range of ±0.06 mg/kg).

In one aspect, the polypeptide is administered daily for 2 to 5 consecutive days, or more, such as daily for 2 consecutive days, for 3 consecutive days, for 4 consecutive days, for 5 consecutive days, or more, preferably for 3 consecutive days.

The above dose regimens are also referred to herein as the "selected dosing schedules" or "selected dose(s)".

In a preferred aspect the polypeptide of the invention used in the above methods of the invention is SEQ ID NO: 71.

Accordingly, the present invention relates to a method for the treatment of RSV infection, such as RSV lower respiratory tract infection, in a young child, said method comprising the administration to the child suffering the RSV infection, of SEQ ID NO: 71, wherein SEQ ID NO: 71 is administered to the child by inhalation at a target concentration of 9 microgram/mL (wherein this value is understood to optionally encompass a range of ±0.5 microgram/mL) or more. The invention also relates to SEQ ID NO: 71 for use in treatment of RSV infection, such as RSV lower respiratory tract infection, in a young child, wherein SEQ ID NO: 71 is administered to the child suffering RSV infection by inhalation at a target concentration of 9 microgram/mL (wherein this value is understood to optionally encompass a range of ±0.5 microgram/mL) or more.

Accordingly, the present invention relates to a method for the treatment of RSV infection, such as RSV lower respiratory tract infection, in a young child, said method comprising the administration to the child suffering the RSV infection, of SEQ ID NO: 71, wherein SEQ ID NO: 71 is administered to the child by inhalation at a deposited dose of 0.020-0.040 mg/kg daily, more specifically at a deposited dose of 0.020-0.035 mg/kg daily, such as e.g. 0.024 mg/kg daily (wherein this value is understood to optionally encompass a range of ±0.002 mg/kg). The invention also relates SEQ ID NO: 71 for use in treatment of RSV infection, such as RSV lower respiratory tract infection, in a young child, wherein SEQ ID NO: 71 is administered to the child suffering RSV infection by inhalation at a deposited dose of 0.020-0.040 mg/kg daily, more specifically at a deposited dose of 0.020-0.035 mg/kg daily, such as e.g. 0.024 mg/kg daily (wherein this value is understood to optionally encompass a range of ±0.002 mg/kg).

Accordingly, the present invention also relates to a method for the treatment of RSV infection, such as RSV lower respiratory tract infection, in a young child, said method comprising the administration to the child suffering the RSV infection, of SEQ ID NO: 71, wherein SEQ ID NO: 71 is administered to the child by inhalation at an inhaled dose of 0.20-0.40 mg/kg daily, more specifically at an inhaled dose of 0.20-0.35 or 0.20-0.45 mg/kg daily, such as e.g. 0.24 mg/kg daily (wherein this value is understood to optionally encompass a range of ±0.02 mg/kg). The invention also relates to SEQ ID NO: 71 for use in treatment of RSV infection, such as RSV lower respiratory tract infection, in a young child, wherein SEQ ID NO: 71 is administered to the child suffering RSV infection by inhalation at an inhaled dose of 0.20-0.40 mg/kg daily, more specifically at an inhaled dose of 0.20-0.35 or 0.20-0.45 mg/kg daily, such as e.g. 0.24 mg/kg daily (wherein this value is understood to optionally encompass a range of ±0.02 mg/kg).

Accordingly, the present invention also relates to a method for the treatment of RSV infection, such as RSV lower respiratory tract infection, in a young child, said method comprising the administration to the child suffering the RSV infection, of SEQ ID NO: 71, wherein SEQ ID NO: 71 is administered to the child by inhalation at a nominal dose of 1.00-2.00 mg/kg daily, more specifically at a nominal dose of 1.00-1.75 mg/kg daily, such as e.g. 1.20 mg/kg daily (wherein this value is understood to optionally encompass a range of ±0.06 mg/kg). The invention also relates to SEQ ID NO: 71 for use in treatment of RSV infection, such as RSV lower respiratory tract infection, in a young child, wherein SEQ ID NO: 71 is administered to the child suffering RSV infection by inhalation at a nominal dose of 1.00-2.00 mg/kg daily, more specifically at a nominal dose of 1.00-1.75 mg/kg daily, such as e.g. 1.20 mg/kg daily (wherein this value is understood to optionally encompass a range of ±0.06 mg/kg).

In one aspect, the polypeptide with SEQ ID NO: 71 is administered daily for 2 to 5 consecutive days, or more, such as daily for 2 consecutive days, for 3 consecutive days, for 4 consecutive days, for 5 consecutive days, or more, such as e.g. for 3 consecutive days.

Pharmaceutical Composition and Formulations

The invention further relates to a composition (also referred to herein as "composition(s) of the invention" or "formulation(s) of the invention") comprising the polypeptide of the invention at a certain concentration, and optionally one or more further components of such compositions known per se. Generally, for pharmaceutical use, the polypeptides of the invention may be formulated as a formulation or compositions (also referred to as "pharmaceutical composition(s) of the invention" or "pharmaceutical formulation(s) of the invention") comprising the polypeptide of the invention at a certain concentration and at least one pharmaceutically acceptable carrier, diluent or excipient and/or adjuvant, and optionally one or more further pharmaceutically active ingredient.

The polypeptide of the invention can be formulated and administered in any suitable manner known per se, for which reference is for example made to standard handbooks, such as Remington's Pharmaceutical Sciences 1990 ($18^{th}$ Ed., Mack Publishing Company, USA), Remington 2005 (the Science and Practice of Pharmacy, $21^{st}$ Ed., Lippincott Williams and Wilkins); or the Handbook of Therapeutic Antibodies (S. Dubel, Ed.), Wiley, Weinheim, 2007 (see for example pages 252-255).

As the polypeptide of the invention and/or composition comprising the same is administered by inhalation (i.e. to the respiratory tract), the formulation is preferably in a form suitable for administration by inhalation. In this respect, the pharmaceutical composition will comprise the polypeptide of the invention and at least one carrier, diluent or excipient suitable for administration to a subject by inhalation, and optionally one or more further active ingredients.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (e.g., serum albumin), amino acids (e.g., aspartic acid, glutamic acid, lysine, arginine, glycine), surfactants (e.g., sodium dodecyl sulfate (SDS), polysorbates such as Tween 20 and Tween 80, poloxamers such as Pluronics, and other nonionic surfactants such as poly(ethylene glycol) (PEG)), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18th ed., Mack Publishing Co., Easton, Pa.), which is incorporated herein in its entirety.

The phrase "carrier suitable for administration by inhalation" as used herein means a pharmaceutically acceptable material, composition or vehicle, such as a liquid or solid filler, diluent, excipient, or solvent, involved in carrying or transporting the agent (e.g. prophylactic or therapeutic agent) e.g. in the respiratory tract. Each carrier must be "acceptable" in the sense of being compatible with the other ingredients of the formulation and not injurious to the patient.

The carrier comprised in the composition of the invention preferably is an aqueous carrier such as e.g. distilled water, MilliQ® water or Water for Injection (WFI). The composition can be buffered by any buffer that is pharmaceutical acceptable. Preferred buffers for use in the composition of the invention include (without being limiting) PBS, phosphate buffer, TrisHCl, histidine buffer and citrate buffer, such as e.g. histidine pH 6.0-6.5, phosphate buffer pH 7.0, TrisHCl pH 7.5 and citrate buffer/phosphate buffer pH 6.5, in particular phosphate ($NaH_2PO_4/Na_2HPO_4$) buffer pH 7.0. Other pharmaceutically acceptable carriers may also be used in a formulation of the present application. Some examples of materials which can serve as pharmaceutically acceptable carriers include: sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and other non-toxic compatible substances employed in pharmaceutical formulations.

As demonstrated in the working examples, concentrations of 50 mg/mL have been used for pulmonary administration of the polypeptide of the invention. It is expected that other concentrations having values around these concentrations (and also outside these values, i.e., higher or lower than these values) therefore also can be used. For example, concentrations of 25, 30, 35, 40, 45, 55, 60, 65, 70, 75 mg/mL can be used. It will be clear to the skilled person that, in view of the specific nominal dose (mg/kg) determined in the present invention, the volume of the pharmaceutical composition filled in the nebulizer (fill volume) will depend on the concentration of the polypeptide of the invention in the a pharmaceutical composition.

In the method of the invention, the nominal dose to be filled in the nebuliser to ensure clinically meaningful reduction of RSV infectivity was determined to be 1.00-2.00 mg/kg daily, more specifically 1.00-1.75 mg/kg daily, such as e.g. 1.20 mg/kg daily (wherein this value is understood to optionally encompass a range of ±0.06 mg/kg). Depending on the weight of the young child, the volume of the pharmaceutical composition (at a particular concentration, such as e.g. 50 mg/mL of polypeptide of the invention) that should be loaded into the nebulizer (also referred to as the "fill volume") will differ. In line with other inhalation products, the administered dose of the polypeptides of the invention (and as such the fill volume of a pharmaceutical composition comprising the polypeptides of the invention at a particular concentration) can be standardised for (narrow) body weight categories (see e.g. Table B-2 and Table B-6 for a pharmaceutical composition of 50 mg/mL).

Inhalation Device—Nebulizer

The present invention also relates to a pharmaceutical device suitable for the delivery by inhalation of the polypeptide of the invention and suitable in the use of a composition comprising the same. The present invention, accordingly, relates to such a device comprising the polypeptide of the invention at the selected dose.

Various inhalation systems are e.g. described on pages 129 to 148 in the review ("Pulmonary Drug Delivery", Bechtold-Peters and Luessen, eds., supra). In the method of the present invention, the device is an inhaler for liquids (e.g. a suspension of fine solid particles or droplets) comprising the polypeptide of the invention. Preferably this device is an aerosol delivery system or a nebulizer comprising the polypeptide of the invention.

The aerosol delivery system used in the method of the invention may comprise a container comprising the composition of the invention and an aerosol generator connected to it. The aerosol generator is constructed and arranged to generate an aerosol of the composition of the invention.

In a preferred aspect, the aerosol delivery system is a nebulizer. Nebulizers produce a mist of drug-containing liquid droplets for inhalation. "Nebulization", as used in the present invention, means the conversion of a liquid to a fine spray. Nebulizers mix medicine with compressed air to create a fine mist that the patient breathes in through a facemask or mouthpiece.

Preferably a vibrating-mesh nebulizers is used. Vibrating-mesh nebulizers are divided into passively and actively vibrating-mesh devices (Newman 2005, J. Appl. Ther. Res. 5: 29-33). Passively vibrating-mesh devices (e.g. Omron MICROAIR® NE-U22 nebulizer) employ a perforated plate having up to 6000 micron sized holes. A vibrating piezoelectric crystal attached to a transducer horn induces "passive" vibrations in the perforated plate positioned in front of it, resulting in extrusion of fluid through the holes and generation of the aerosol. Actively vibrating-mesh devices (e.g. AERONEB® Pro nebulizer) may employ a "micropump" system which comprises an aerosol generator consisting of a plate with up to 1000 dome-shaped apertures and a vibrating element which contracts and expands on application of an electric current. This results in upward and downward movements of the mesh by a few micrometers, extruding the fluid and generating the aerosol. Other examples of vibrating-mesh nebulizers include the Akita2 Apixneb (Activaero, now Vectura, Germany), EFLOW® (PARI GmbH, Grafelingen, Germany; see also U.S. Pat. No. 5,586,550), AERONEB® (Aerogen, Inc., Sunnyvale, Calif.; see also U.S. Pat. Nos. 5,586,550; 5,938,117; 6,014,970; 6,085,740; 6,205,999), or the FOX nebulizer (Activaero, now Vectura, Germany), all adapted for pediatric use.

In a preferred aspect, a continuous flow nebuliser is used. Considering that young infants with bronchiolitis may require additional oxygen or air supply, maintaining a continuous oxygen or air supply of 2 L/min through the delivery system is recommended.

Accordingly, the nebulizer can be used with or without additional air or $O_2$ flow. Preferably, the nebulizer is used with additional air or $O_2$ flow, such as a flow of 2 L/min additional air or $O_2$.

An exemplary inhalation device for delivering the polypeptide of the invention to a patient may comprises (a) an aerosol generator with a vibratable mesh; (b) a reservoir for a liquid to be nebulised, said reservoir being in fluid connection with the vibratable mesh; (c) a gas inlet opening; (d) a face mask, having a casing, an aerosol inlet opening, a patient contacting surface, and a one-way exhalation valve or a two-way inhalation/exhalation valve in the casing having an exhalation resistance selected in the range from 0.5 to 5 mbar; and (e) a flow channel extending from the gas inlet opening to the aerosol inlet opening of the face mask, the flow channel having a lateral opening through which the aerosol generator is at least partially inserted into the flow channel, and a constant flow resistance between the gas inlet opening and the aerosol inlet opening of the face mask at a flow rate of 1 to 20 L/min.

Figure 33:
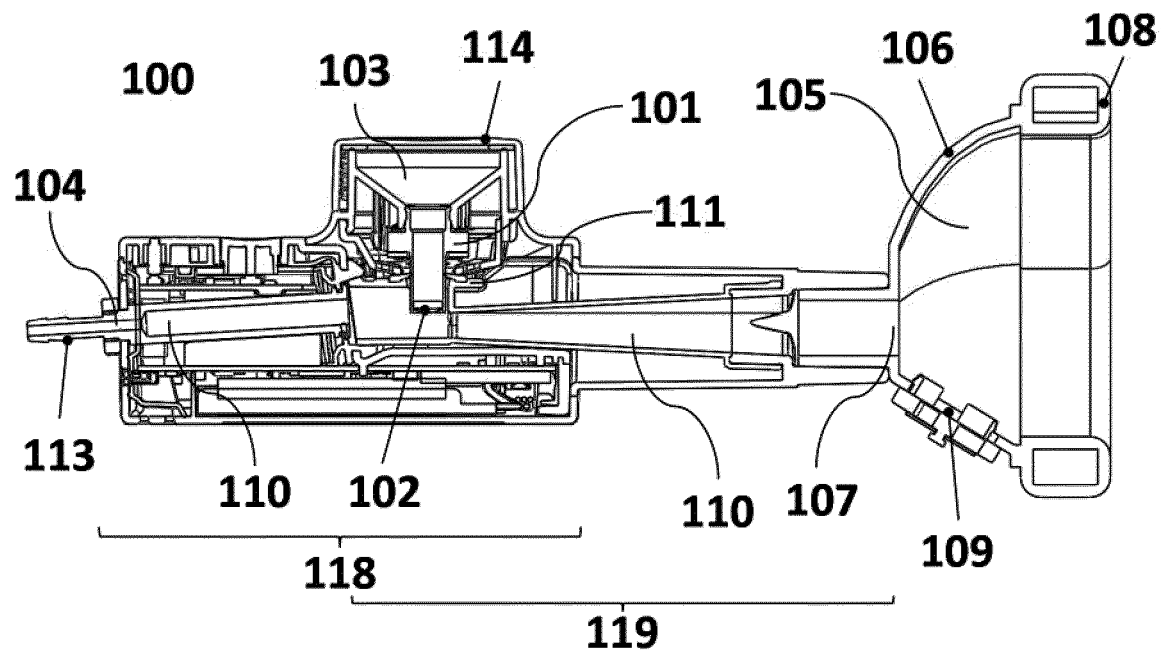
FIG. 33 shows a cross-sectional side view of a specific embodiment of the inhalation device according to the invention

A cross-sectional side view of one exemplary embodiment of such an inhalation device can be seen in FIG. 33. FIG. 33 depicts an inhalation device (100); an aerosol generator (101) with a vibratable mesh (102); a reservoir (103) in fluid connection with the vibratable mesh (102); a gas inlet opening (104); a face mask (105) with a casing (106), an aerosol inlet opening (107), a patient contacting surface (108), and a one-way exhalation valve or a two-way inhalation/exhalation valve (109); and a flow channel (110) leading from the gas inlet opening (104) to the aerosol inlet opening (107) of the face mask (105). The flow channel (110) has a lateral opening (111) through which the aerosol generator (101) is partially inserted with its downstream end. In the depicted embodiment, the reservoir is covered by a screw-on lid (114) and the gas inlet opening (104) is shaped as, or equipped with, a tube fitting (113).

Figure 34:
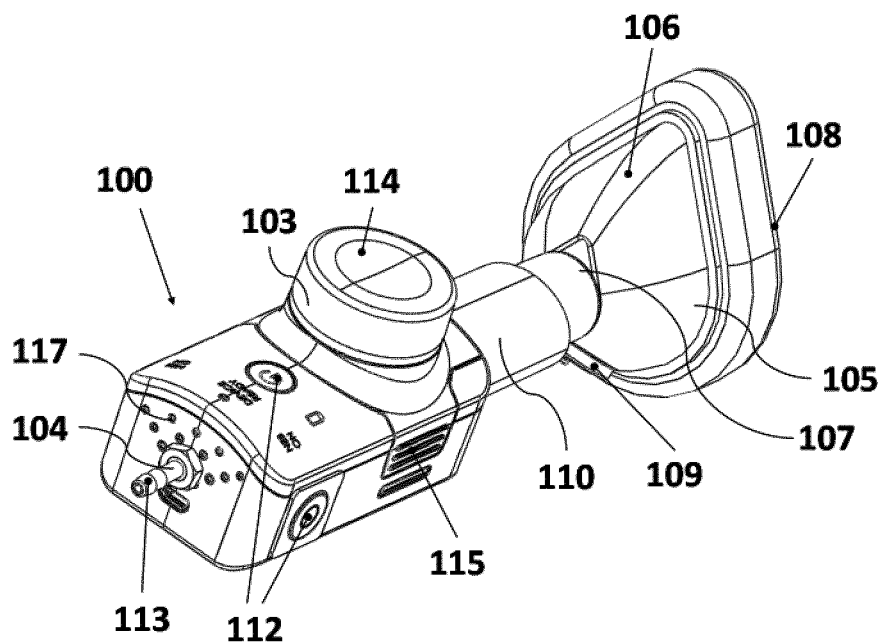
FIG. 34 shows a perspective view of a specific embodiment of the inhalation device according to the invention.
Figure 35:
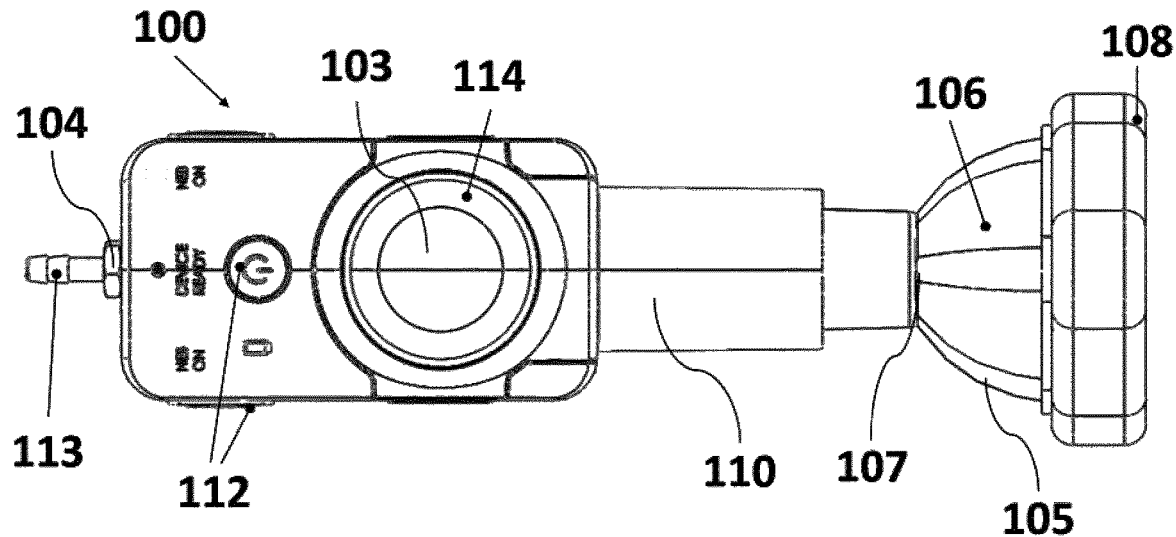
FIG. 35 shows a top view of a specific embodiment of the inhalation device according to the invention.
Figure 36:
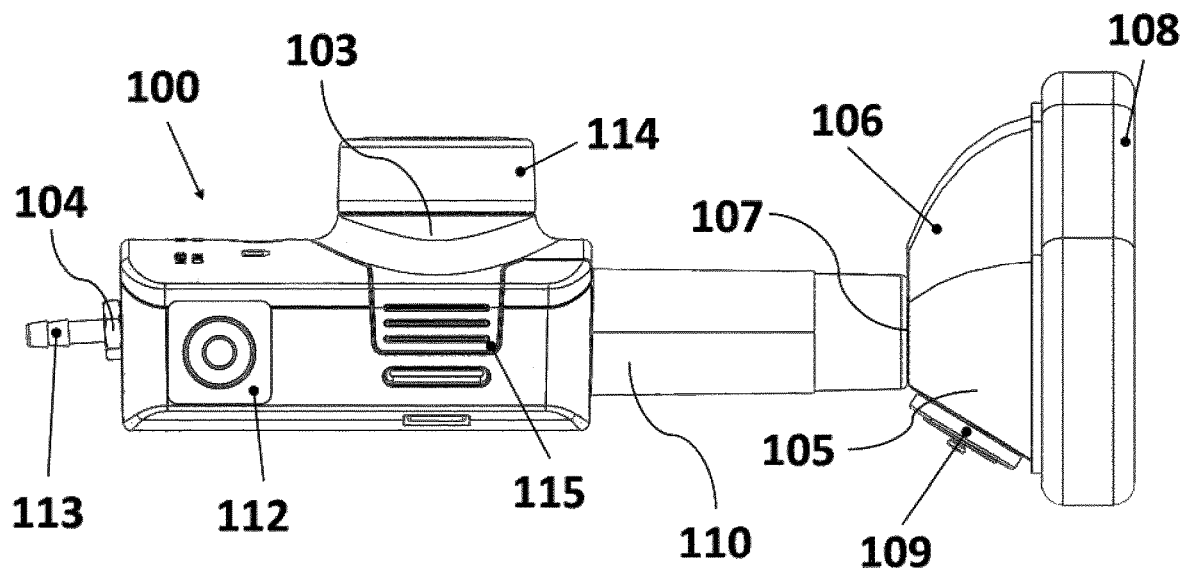
FIG. 36 shows a side view of a specific embodiment of the inhalation device according to the invention.
Figure 37:
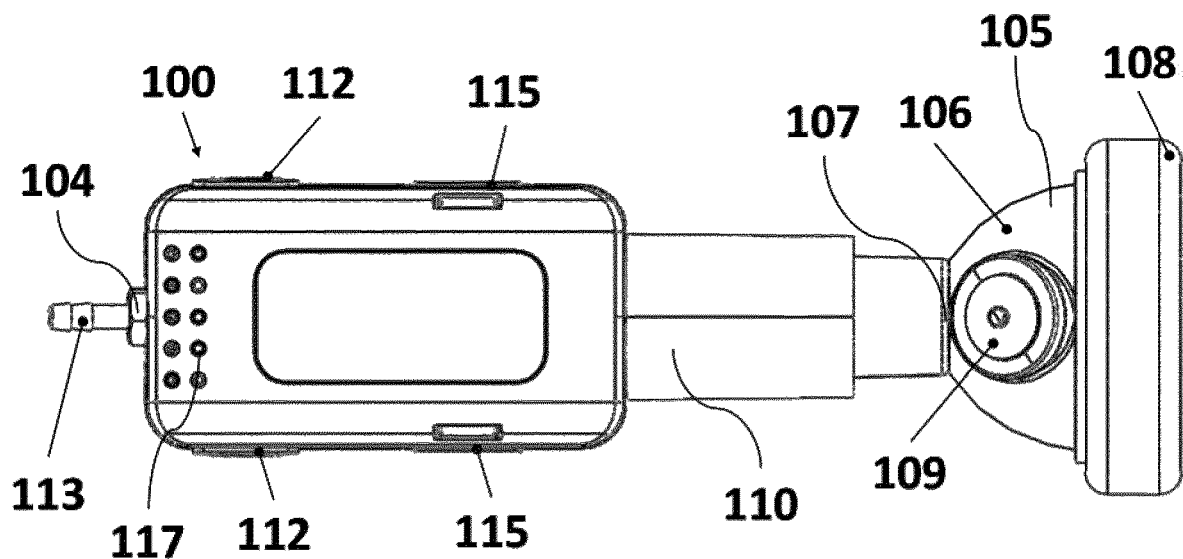
FIG. 37 shows a bottom view of a specific embodiment of the inhalation device according to the invention.
Figure 38:
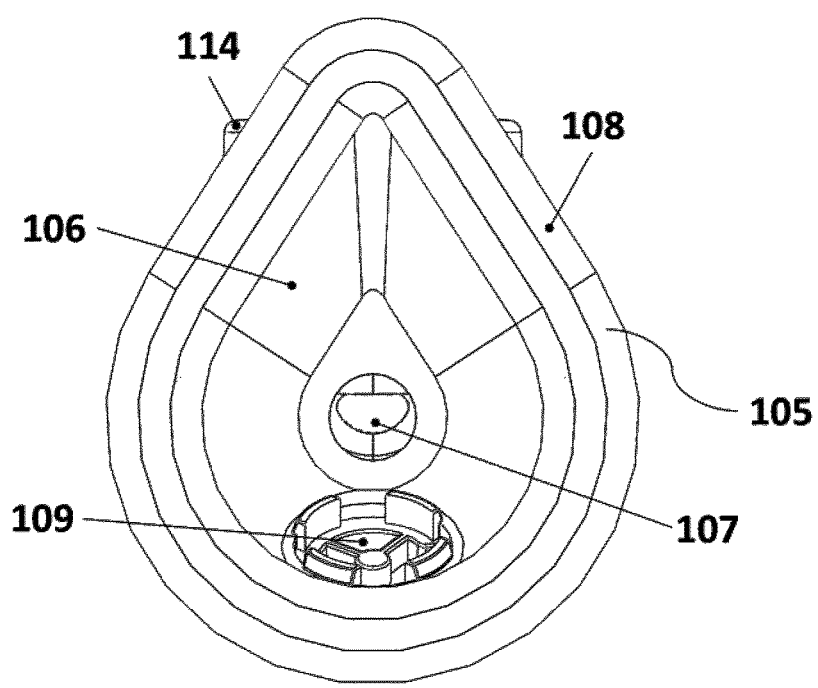
FIG. 38 shows a front view of a specific embodiment of the inhalation device according to the invention.

The exemplary inhalation device of FIG. 33 is further depicted in a perspective side view in FIG. 34 and in top, side and bottom views in FIGS. 35 to 37, respectively. The front and rear views of this exemplary inhalation device are provided in FIGS. 38 and 39, respectively.

In one aspect, the vibratable mesh (102) of the inhalation device used in the method of the invention may comprise from 1,000 to 4,000 openings whose smallest diameter is predominantly in the range from 1.5 to 3.0 µm.

In one aspect, the reservoir (103) of the inhalation device used in the method of the invention may have a volume of 0.1 to 10 mL, or from 0.5 to 5 mL, to accommodate the liquid, which is typically a pharmaceutical composition comprising an active ingredient. Preferably, the reservoir (103) is located at a superior position relative to the body of the aerosol generator (101). It may be closable by a screw-on or snap-on lid; see e.g. the screw-on lid (114) depicted in FIG. 33.

Since infants up to the age of 18 months are virtually obligate nose-breathers, controlled inhalation through a mouthpiece is not feasible and the interface requires special attention in terms of facemask type and size appropriate for the different ages.

The face mask (105) of the inhalation device used with the method of the invention may be configured to allow the exhalation by the patient through the mask. This is achieved by the valve which exhibits a rather small exhalation resistance. The valve, or the exhalation resistance of the valve, may be selected within the range specified above and in view of the patient.

Preferably, the nominal internal volume of the face mask is not more than about 120 mL. As used herein, the nominal internal volume is understood as the internal volume enclosed by the casing from the aerosol inlet opening to the patient contacting surface when the patient contacting surface is placed on a flat surface. This volume is slightly larger than the effective internal volume, or so-called dead space, which is the volume enclosed by the mask when placed against the face of a patient, and which therefore depends on the size and shape of the patient's face. If the patient is a school child, the nominal internal volume is preferably not more than about 90 mL, or even not more than about 80 mL, or not more than about 70 mL, or not more than about 60 mL, or not more than about 50 mL, or not more than about 40 mL, respectively, depending on the size of the face of the patient. It is currently preferred to select a mask with a nominal internal volume of not more than about 40 or 50 mL if the patient is a neonate.

It is further preferred to select the nominal internal volume of the face mask with respect to the patient's average tidal volume. Advantageously, the nominal internal mask volume is smaller than the tidal volume. For example, if the patient is a paediatric patient having an average tidal volume during normal breathing of about 80 mL, the nominal internal face mask volume should be smaller than this. In particular, the respective volume may be in the range from about 10% to about 80% of the average tidal volume. In further embodiments, the nominal internal face mask volume is not more than about 60%, or even not more than about 50%, of the patient's average tidal volume.

In one embodiment, the face mask may have a two-way inhalation- and exhalation valve having a resistance of not more than 3 mbar in either direction, and wherein the nominal internal volume of the face mask is not more than about 50 mL. This embodiment is particularly suitable for small paediatric patients such as neonates, infants, and toddlers. In another embodiment, the face mask may have one or more inhalation valves and one or more exhalation valves, wherein the exhalation valve has a resistance of not more than 3 mbar, and wherein the nominal internal volume of the mask is not more than about 70 mL. This embodiment is particularly suitable for toddlers and children.

Optionally, the face mask may comprise further inhalation and/or exhalation valves. If so, the effective exhalation pressure of the combined valves should still be in the specified range, i.e. between about 0.5 and 5 mbar. Optionally, the exhalation pressure may also be selected from about 0.5 mbar to about 3 mbar, such as about 1 mbar or about 2 mbar, respectively. The valve(s) provided in the face mask may have any structure suitable for providing this exhalation resistance; e.g. slit valves, duck bill valves or membrane valves, to mention only a few. For example, the valve may be a one-way valve with a cross-slit and an overlying membrane, such as a silicone membrane. In one direction, from the cross-slit to the membrane, the valve opens, whereas in the opposite direction the membrane will be pressed tightly onto the cross and thus blocks the valve. Depending on which way round the valve is inserted into the face mask, it can serve both as an inhalation or an exhalation valve.

The inhalation device used in the method of the invention may be connected to a gas source that provides a gas at a constant flow rate in the range from 1 to 5 L/min; said gas source being connected to the inhalation device such that the gas enters the flow channel through the gas inlet opening. The gas provided by said gas source may be selected from oxygen, air, oxygen-enriched air, a mixture of oxygen and nitrogen, and a mixture of helium and oxygen.

The gas inlet opening (104) is preferably connectable to an external gas source, either directly or indirectly via a tube or other conduct. The gas inlet opening (104) may be shaped as, or equipped with, a tube fitting (113) in order to facilitate the attachment of a gas source, as can be seen e.g. in FIGS. 33 and 34. The gas inlet opening (104) may be accommodated in a rear position of the inhalation device (100), as shown in FIGS. 33 to 37 and FIG. 39 for the exemplary embodiment.

In a preferred embodiment, the gas inlet opening (104) is the only inlet opening for allowing a gas to flow into the flow channel (110), with the exception of the aerosol generator, or the reservoir connected with the aerosol generator, through which very small amount of gas (typically air) may enter the device to replace the nebulized liquid.

In one embodiments not depicted herein, the device may comprise a flow restrictor in the flow channel upstream of the lateral opening which is adapted to restrict the flow of a gas in the flow channel to a constant flow rate selected in the range from 1 to 5 L/min.

In one aspect, the inhalation device used in the method of the invention may have a flow channel (110), which extends from the gas inlet opening (104) to the aerosol inlet opening (107) of the face mask (105). The flow channel may have a lateral opening (111), as exemplified by the device depicted in FIG. 34, through which the aerosol generator is at least partially inserted into the flow channel. Moreover, the flow channel may exhibit a constant flow resistance between the gas inlet opening and the aerosol inlet opening of the face mask at a flow rate of 1 to 20 L/min, and in particular at a flow rate in the range from about 1 L/min to about 5 L/min.

The flow channel may be configured to receive a gas from an external gas source through the gas inlet opening which forms the upstream end of the flow channel. The upstream portion of the flow channel, i.e. the segment from (and including) the gas inlet opening (104) to the lateral opening (111) through which the aerosol generator (101) is at least partially inserted, is preferably sized and shaped such as to achieve a laminar flow of a gas which in conducted through the flow channel at a constant flow rate selected in the range from 1 to 20 L/min, and in particular at a constant flow rate in the range from about 1 L/min to about 5 L/min.

The flow channel also may have a constant flow resistance between the gas inlet opening and the aerosol inlet opening of the face mask.

The lateral opening (111) which receives the aerosol generator (101) may preferably be located at an upper position of the flow channel (110) with respect to the normal orientation of the device in use, as is depicted e.g. in FIGS. 33 and 34. The opening is preferably sized to match the dimensions of the aerosol generator so that the opening is completely and tightly closed when the aerosol generator is received. Preferably, the aerosol generator is in a partially inserted position during use, and the downstream end of the aerosol generator protrudes towards (or even to) the longitudinal centre axis of the flow channel.

In one embodiment, the aerosol generator may be oriented such as to emit nebulised aerosol into the flow channel at an angle of approximately 90° to the longitudinal axis of the flow channel. In this case, the aerosol generator is arranged in an approximately vertical orientation and the vibrating mesh is approximately horizontal.

Optionally, the aerosol generator is selected and operated such as to have an aerosol generation rate (or nebulisation rate) of at least about 0.1 mL/min, or of at least 0.2 mL/min. In some embodiments, the aerosol generator has a nebulisation rate of at least 0.3 mL/min, 0.4 mL/min, 0.5 mL/min, 0.6 mL/min, or even at least 0.7 mL/min.

The flow channel's dimensions may be such that the total interior volume of the channel between the lateral opening and the aerosol inlet opening of the face mask is not more than about 30 mL. Optionally, it is not more than about 25 mL, or not more than about 20 mL, respectively. In some cases, the interior volume of the flow channel may be less than about 18 mL, or even less than about 15 mL.

In a specific embodiment, the flow channel may have an internal diameter at a position immediately upstream of the lateral opening of about 10 mm to about 13 mm; optionally in combination with a vibratable mesh that has a total diameter of about 6 mm to about 8 mm. It is noted that the diameter of the region of the mesh having the openings, or apertures, may be smaller than the total diameter, e.g. by about 1 to 3 mm.

In a specific embodiment, the ratio of the internal diameter of the flow channel immediately upstream of the lateral opening to the diameter of the vibratable mesh may be from about 1 to about 2.5, or from about 1.2 to about 2, respectively. Furthermore, the ratio of the internal diameter of the flow channel immediately upstream of the lateral opening to the diameter of the aperture region of the vibratable mesh may be from about 1.2 to about 4, such as from about 1.6 to about 3.

The inhalation device used in the method of the invention may also comprises a switch (112) for starting and stopping the operation of the aerosol generator (101), as shown e.g. in FIG. 34. In this context, the operation of the aerosol generator comprises the continuous vibration of the vibratable mesh.

In one aspect, the inhalation device used in the method of the invention may comprises a) a base unit (118) comprising an electronic controller for controlling the aerosol generator (101), and an upstream portion of the flow channel including the gas inlet opening (104); and b) a mixing channel unit (119), comprising a downstream portion of the flow channel including the lateral opening (111), wherein the downstream portion comprises a segment where the flow channel widens in the downstream direction, said segment being positioned downstream of the lateral opening.

Figure 39:
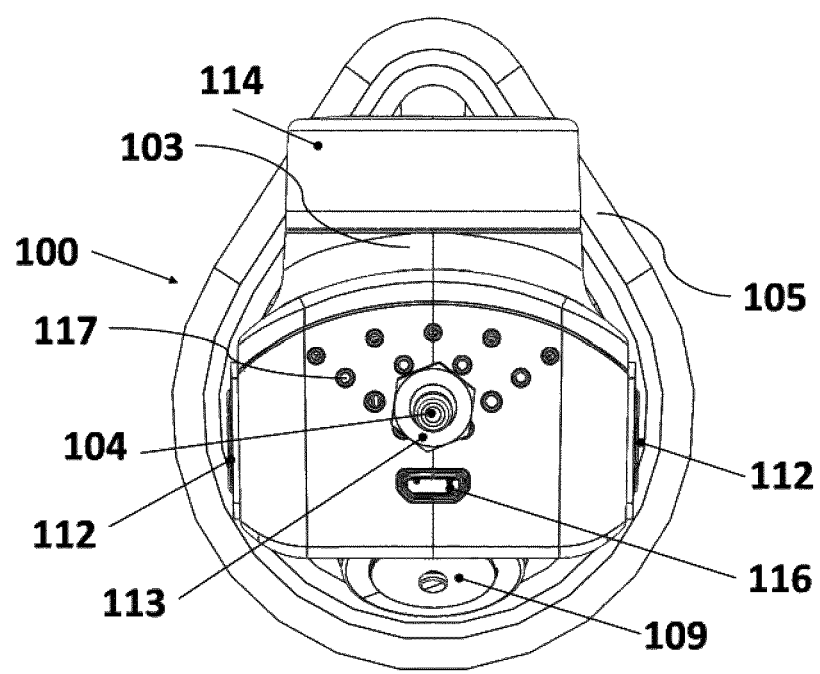
FIG. 39 shows a rear view of a specific embodiment of the inhalation device according to the invention.

Optionally, the base unit with the electronic controller may further comprise, or house, a battery (e.g. a rechargeable battery), data storage means and/or a USB-port (116) for charging and data retrieval, such as depicted in FIG. 39.

Further optionally, small holes (117) may optionally be provided, e.g. at the rear of the inhalation device as shown in FIGS. 34 and 39, and/or at the bottom side of the inhalation device as shown in FIG. 37; in order to allow for air-cooling of e.g. the electronic controller and any other parts of the base unit (118) which may generate warmth. However, these small holes (117) are not in fluid connection with the flow channel (110).

For examples of inhalation devices for use with the method of the invention reference is made to the co-pending International patent application by Ablynx N.V. and Vectura GmbH with the same filing date as the present application, entitled "Inhalation device for use in aerosol therapy of respiratory diseases".

The inhalation device or nebulizer is loaded with the pharmaceutical composition of the invention. Accordingly, the present invention also relates to an inhalation device or nebulizer containing a pharmaceutical composition comprising the polypeptide of the invention. In a preferred aspect, the inhalation device or nebulizer contains a pharmaceutical composition that comprises SEQ ID NO: 71. As indicated above, the polypeptide of the invention can be present in the nebulizer at any suitable concentration such as 25, 30, 35, 40, 45, 50, 55, 60, 65, 70, 75 mg/mL, preferably at a concentration of 50 mg/mL.

To ensure clinically meaningful reduction of RSV as described herein, the polypeptide of the invention is administered at a nominal dose of 1.00-2.00 mg/kg daily, preferably 1.00-1.75 mg/kg, such as e.g. 1.20 mg/kg daily (wherein this value is understood to optionally encompass a range of ±0.06 mg/kg). Depending on the weight of the young child, the volume of pharmaceutical composition) (at a concentration of 50 mg/mL of polypeptide of the invention) that should be loaded into the nebulizer (also referred to as the "fill volume") will be as follows (see also Table B-2):

| Weight category | Fill Volume | Fill Dose | Nominal dose (mg/kg) |
| --- | --- | --- | --- |
| 5.0-6.0 kg | 0.150 mL | 7.5 mg | 1.50-1.25 |
| 6.1-8.0 kg | 0.200 mL | 10.0 mg | 1.64$^c$-1.25 |
| 8.1-10.0 kg | 0.250 mL | 12.5 mg | 1.54-1.25 |
| 10.1-12.0 kg | 0.300 mL | 15.0 mg | 1.49-1.25 |
| 12.1-14.0 kg | 0.350 mL | 17.5 mg | 1.45-1.25 |
| 14.1-16.0 kg | 0.400 mL | 20.0 mg | 1.42-1.25 | or as follows (see also Table B-6):

| Weight category | Fill Volume | Fill Dose | Nominal dose (mg/kg) |
| --- | --- | --- | --- |
| 3.5-3.9 kg | 0.100 mL | 5.0 mg | 1.43-1.28 |
| 4.0-5.0 kg | 0.130 mL | 6.5 mg | 1.63-1.30 |
| 5.1-6.0 kg | 0.150 mL | 7.5 mg | 1.47-1.25 |
| 6.1-8.0 kg | 0.200 mL | 10.0 mg | 1.64-1.25 |
| 8.1-10.0 kg | 0.250 mL | 12.5 mg | 1.54-1.25 |
| 10.1-12.0 kg | 0.300 mL | 15.0 mg | 1.49-1.25 |
| 12.1-14.0 kg | 0.350 mL | 17.5 mg | 1.45-1.25 |
| 14.1-16.0 kg | 0.400 mL | 20.0 mg | 1.42-1.25 |
| 16.1-19.0 kg | 0.500 mL | 25.0 mg | 1.32-1.55 |

The above doses are also referred to herein as the "selected dosing schedules".

Accordingly, the present invention relates to an inhalation device or nebulizer comprising 0.150-0.400 mL or 0.100-0.500 mL (such as 0.100 mL, 0.130 mL, 0.150 mL, 0.200 mL, 0.250 mL, 0.300 mL, 0.350 mL, 0.400 mL, 0.500 mL) of a 50 mg/mL composition of a polypeptide of the invention, preferably SEQ ID NO: 71. More specifically, the present invention relates to an inhalation device or nebulizer comprising 0.150-0.400 mL or 0.100-0.500 mL (such as 0.100 mL, 0.130 mL, 0.150 mL, 0.200 mL, 0.250 mL, 0.300 mL, 0.350 mL, 0.400 mL) of a 50 mg/mL composition of a polypeptide of the invention, preferably SEQ ID NO: 71 for use in the treatment of RSV infection, such as e.g. RSV lower respiratory tract infection, in a young child.

In one aspect, the young child is age less than 24 months.

In one aspect, the young child is age less than 36 months (3 years).

In one aspect, the young child is age 1 month to less than 24 months.

In one aspect, the young child is age 1 month to less than 36 months (3 years).

In one aspect, the young child is age 5 months to less than 24 months.

In one aspect, the young child is age 5 months to less than 36 months (3 years).

In one aspect, the young child is an infant.

In one aspect, the young child is a toddler.

In one aspect, the young child is diagnosed with RSV lower respiratory tract infection but is otherwise healthy.

In one aspect, the young child is hospitalised for RSV lower respiratory tract infection.

Additional Therapeutic Agents

The polypeptides of the invention may be administered as a monotherapy or in combination with other pharmaceutically active compounds or principles that are or can be used for the treatment of RSV infection, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

As such, the present invention also provides methods and dosing schedules for pulmonary administration of a polypeptide of the invention that bind and neutralize hRSV, wherein the polypeptide is administered in combination with at least one additional therapeutic agent.

Without being limiting, additional therapeutic agents can be selected from the standard of care during hospitalisation for RSV infections, such as RSV low respiratory tract infection, including (without being limiting) bronchodilators, antibiotics (e.g. in case of secondary bacterial infection [surinfection] during hospitalisation), apinephrine, anticholinergics, antipyretica and/or nonsteroidal antiinflammatory medication.

In one aspect, the polypeptide of the invention is administered in combination with a bronchodilator. Accordingly, the present invention also relates to a method for the treatment of RSV infection in a young child, said method comprising the administration to the child suffering the RSV infection, of a polypeptide of the invention, wherein the polypeptide is administered to the child by inhalation at the selected dosing schedules in combination with a bronchodilator. In the method of the invention, the polypeptide of the invention and the bronchodilator are administered to the respiratory tract (i.e. by inhalation) as a combination therapy (kit of parts). In this method, the polypeptide of the invention and the bronchodilator are used as part of a combined treatment regimen. More specifically, both parts of this combination therapy are administered to the respiratory tract (i.e. by inhalation) simultaneously, separately or sequentially.

There are two main classes of bronchodilators, i.e. the sympaticomimetics, including the short-acting and the long-acting beta2-mimetics, and the anticholinergics. Short-acting mimetics include (but are not restricted to) salbutamol, terbutaline, fenoterol, pirbuterol and tuloteroterol. They can be used as a base or as an acceptable pharmaceutical salt. The long-acting beta2-mimetics include (but are not restricted to) formoterol and salmeterol. They can also be used as a base or as an acceptable pharmaceutical salt. The anticholinergic drugs include (but are not restricted to) ipratropium, oxitropium and tiotropium.

Without being limiting, additional bronchodilators for use in the method of the invention include Accu Hale, albuterol, bitolterol, ephedrine, epinephrine, isoetharine, isoproterenol, metaproterenol, pirbuterol, racepinephrine, ritodrine, terbutaline, levosabutamol, levabuterol, clenbuterol, amphetamine, methamphetamine, cocaine, theophylline, caffeine, theobromine, THC, and MDPV.

The bronchodilator class of molecules with very long duration of action will have to be administered only once a day (e.g. tiotropium). Long acting beta2-mimetics are usually administered twice a day like formoterol and salmeterol. Finally, there are short-acting bronchodilators such as salbutamol, terbutaline, ipratropium or oxitropium which have to be administered 4 to 6 times a day. Based on such information, treatment schedules can be designed in order to take optimal advantage of the combination therapy. The treatment schedules may encompass the simultaneous, separate or sequential administration of the polypeptide of the invention and the bronchodilator. The most common devices for the administration of the combination therapy (kit of parts) are a nebulizer, a metered dose inhaler (MDI), and a combination of these.

In one aspect, the polypeptide of the invention and the bronchodilator are administered simultaneously. In this embodiment, the polypeptide of the invention and the bronchodilator are administered in admixture in inhalable form.

Without being limiting, the inhalable form of the polypeptide of the invention and the bronchodilator can be an aerosol obtained from simultaneously nebulizing (e.g. with a nebulizer) the polypeptide of the invention and the bronchodilator, both preferably present in the same composition (of the invention).

In another aspect, the polypeptide of the invention and the bronchodilator are administered separately. In this embodiment, the polypeptide of the invention and the bronchodilator are administered in separate inhalable form. Without being limiting, the separate inhalable form of the polypeptide of the invention and/or of the bronchodilator can be an aerosol obtained from nebulizing (e.g. with a nebulizer) the polypeptide of the invention or the bronchodilator, separately present in a composition (of the invention). Alternatively, the separate inhalable form of the polypeptide of the invention and/or of the bronchodilator can be an aerosol obtained from nebulizing (e.g. with a nebulizer) the polypeptide of the invention and a separate aerosol obtained from breakup into droplets (e.g. with a metered dose inhaler (MDI)) of the bronchodilator dissolved or suspended in the volatile propellant, followed by rapid evaporation of these droplets. As such, the polypeptide of the invention and the bronchodilator are administered with two different (types of) inhalers, each producing a separate inhalable form. Without being limiting, following combinations can be proposed:

Inhalation of the bronchodilator with a MDI and inhalation of the polypeptide of the invention with a nebulizer;

Inhalation of the bronchodilator with a nebulizer and inhalation of the polypeptide of the invention with another nebulizer.

In another aspect, the polypeptide of the invention and the bronchodilator are administered sequentially. In this embodiment, the polypeptide of the invention and the bronchodilator are administered separately and sequentially in inhalable form. Without being limiting, the inhalable form of the polypeptide of the invention and/or of the bronchodilator can be an aerosol obtained from nebulizing (e.g. with a nebulizer) the polypeptide of the invention or the bronchodilator, separately present in a composition (of the invention). Alternatively, the separate inhalable form of the polypeptide of the invention and/or of the bronchodilator can be an aerosol obtained from nebulizing (e.g. with a nebulizer) the polypeptide of the invention and a separate aerosol obtained from breakup into droplets (e.g. with a metered dose inhaler (MDI)) of the bronchodilator dissolved or suspended in the volatile propellant, followed by rapid evaporation of these droplets. For this sequential administration of the combination therapy, the polypeptide of the invention and the bronchodilator should be present in two different (separate) compositions of the invention that are separately loaded into the inhaler device, in order that two separate, sequential inhalable forms can be generated. In this embodiment, the polypeptide of the invention and the bronchodilator may be administered with two different (types of) inhaler. However, the use of two different inhalers is not necessarily required as in some devices (such as e.g. in a nebulizer) the separate compositions can be loaded sequentially. Without being limiting, following combinations can be proposed:

Inhalation of the bronchodilator with a MDI followed by inhalation of polypeptide of the invention with a nebulizer;

Inhalation of the bronchodilator with a nebulizer followed by inhalation of polypeptide of the invention with a nebulizer (which can be the same or different);

Inhalation of the polypeptide of the invention with a nebulizer followed by inhalation of the bronchodilator with a MDI;

Inhalation of the polypeptide of the invention with a nebulizer followed by inhalation of bronchodilator with a nebulizer (which can be the same or different).

Preferred intervals for the sequential administration of the polypeptide of the invention and the bronchodilator will depend on the polypeptide of the invention and the bronchodilator used (as is described above) and may include from 5 minutes to 24 hours or more, such as e.g. 5 minutes, 10 minutes, 15 minutes, 20 minutes, 30 minutes, 1 hour, 4 hours, 6 hours, 8 hours, 12 hours, etc.

In a preferred aspect, the bronchodilator is a short-acting beta2-agonist, such as e.g. salbutamol.

In a preferred aspect, the bronchodilator, such as a short-acting beta2-agonist, is administered with a MDI prior to administration of the polypeptide of the invention with a nebulizer. For example, the bronchodilator, a short-acting beta2-agonist, can be administered 10-15 minutes prior to the administration of the polypeptide of the invention. For example, the short-acting beta2-agonist such as salbutamol is administered to the young child at a dose of 200 micrograms (e.g. two puffs of 100 microgram) 15 minutes prior to administration of the polypeptide of the invention.

In another preferred aspect, the bronchodilator is administered with a nebulizer prior to administration of the polypeptide of the invention with a nebulizer. In this preferred aspect, the polypeptide of the invention and the bronchodilator can be administered with the same nebulizer (i.e. each of the polypeptide of the invention and the bronchodilator can be present in a separate composition that is sequentially loaded into the nebulizer) or with two different nebulizers.

In another preferred aspect, the polypeptide of the invention and the bronchodilator are administered simultaneously with a nebulizer. In this preferred aspect, the polypeptide of the invention and the bronchodilator are preferably present in one single compositions of the invention which is loaded into the nebulizer. Else, the polypeptide of the invention and the bronchodilator are present in two different compositions of the invention that are both loaded into the nebulizer.

EXAMPLES

Figure 3:
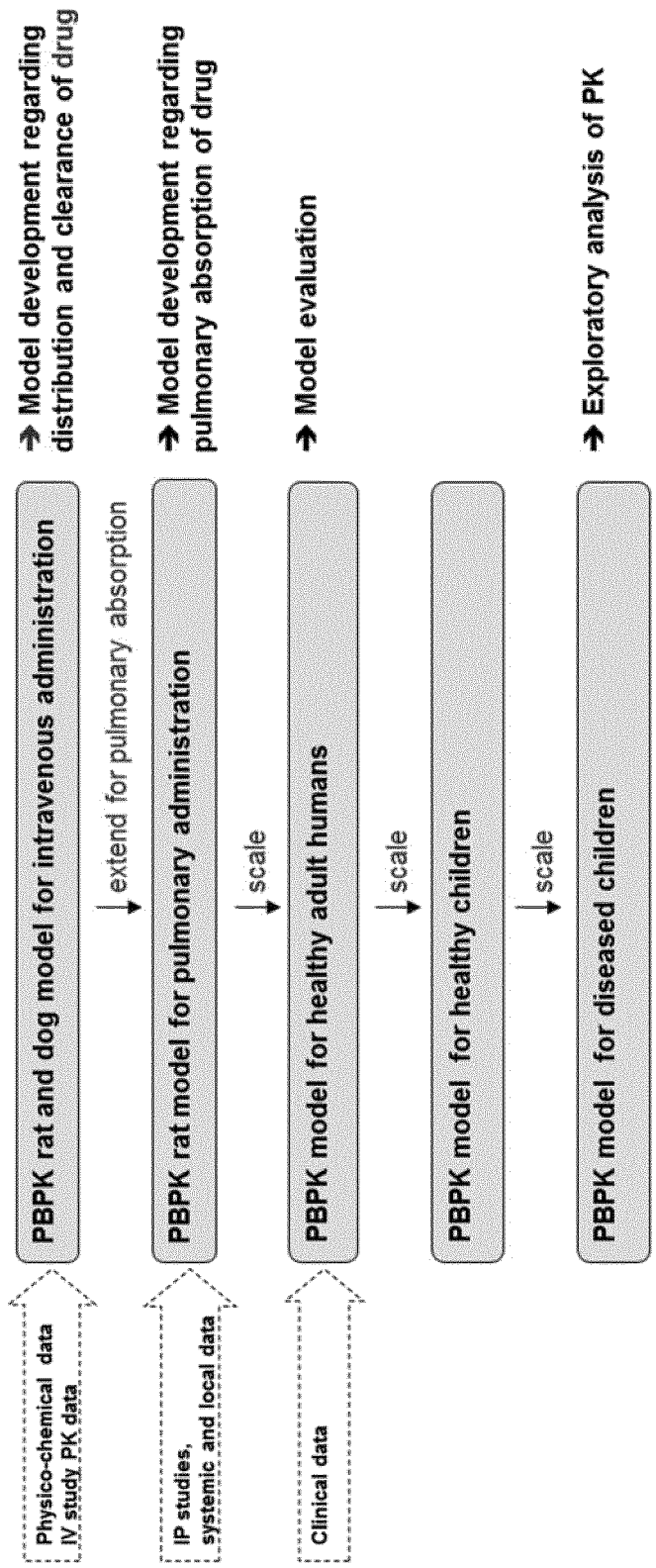
FIG. 3 is a schematic diagram depicting PBPK model-building and scaling steps. IP: intrapulmonary; IV: intravenous; physic-chemical data: characterization of SEQ ID NO: 71.

Example 1: Development of a Model for Dose Determinations in a Pediatric Population A PBPK model for the diseased children was developed in a multi-step scaling approach (FIG. 3; Examples 2-10) using preclinical as well as predicted and measured clinical data (Table B-1).

Dose selection was based on multiples of the $IC_{90}$ value generated from typical in vitro microneutralization assays in order to achieve efficacy. The average $IC_{90}$ value of SEQ ID NO: 71 for the least sensitive prototypic RSV B 18537 strain as determined in micro-neutralization assays was ~90 ng/mL (n=20). A value 100 fold over this $IC_{90}$ (9 µg/ml) was taken as target concentration in order to account for possible differences in RSV clinical isolate sensitivity.

As the target (RSV F protein) is not expressed in humans, and there is no possibility for extrapolating efficacy from adults to children, dose determination can only be based on a modelling approach. In the present approach, a model was developed that takes into account the anatomy and physiology of the young children, growth and development processes such as organ maturation, changes in blood flow, body composition, and ontogeny of elimination mechanisms, including changes in the respiratory system (see FIG. 1, and the more detailed explanation further below).

Figure 2:
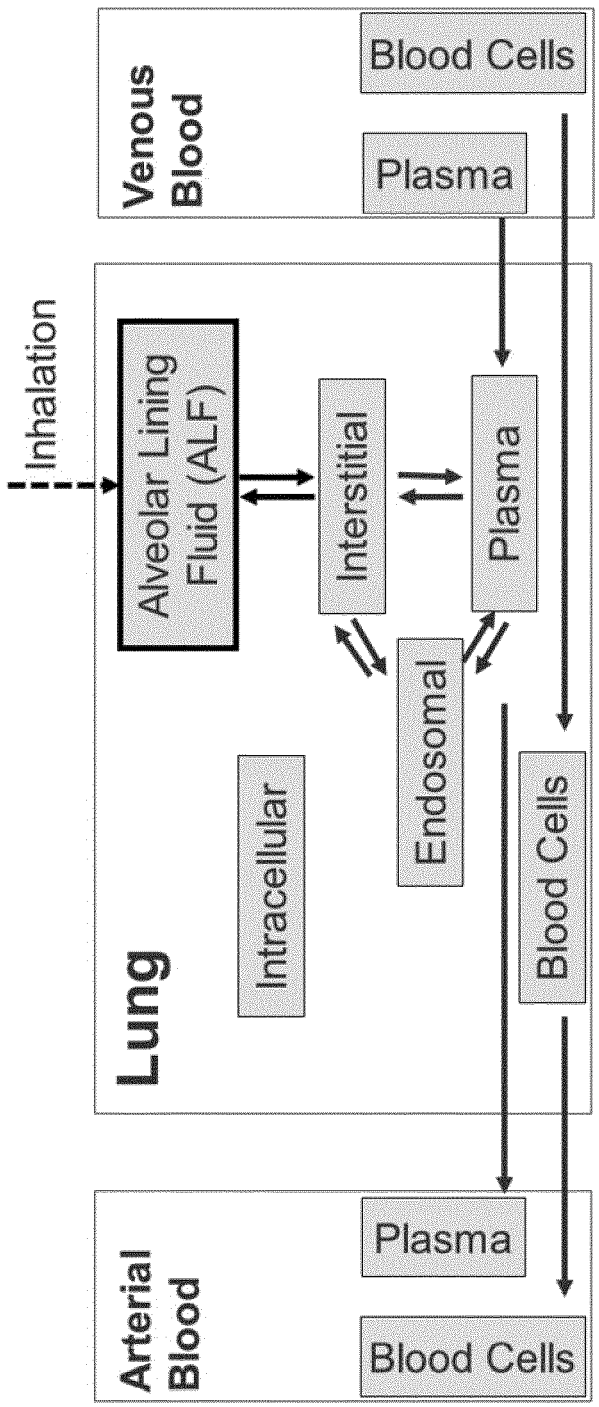
FIG. 2 is a graphical representation of the lung organ in the model for pulmonary administration of the present invention. The extension of the model structure compared to a standard PK-SIM® model is marked by the bold box that represents the alveolar lining fluid (ALF compartment).

PBPK modelling (Barrett et al. 2012, Clin. Pharmacol. Ther. 92: 40-9; Khalil and Laer 2011, J. Biomed. Biotechnol. Epub 2011 Jun. 1) was used to bridge pediatric and adult pharmacology. This was done by establishing an inhalation PBPK model for adults, which was then scaled to children. The PBPK models was built using the software PK-Sim® (Bayer Technology Services, Leverkusen, Germany; www.pk-sim.com, version 5.1.3 for PBPK model building, and version 5.2.2 and 5.3.2 for population simulations). PK-Sim® is a commercially available tool for PBPK modelling of drugs in laboratory animals and humans. PK-Sim® includes a generic PBPK model for protein therapeutics and macromolecules (FIG. 2). For a detailed description about the general PBPK model structure implemented in PK-Sim® see Willmann et al. (2007, J. Pharmacokinet. Pharmacodyn. 34: 401-431; 2005, 1: 159-168; 2003, Biosilico 1: 121-124). This model was used to build the PBPK model for intravenous (IV) administration and the base model for pulmonary administration.

In order to describe the absorption from the alveolar space, an additional compartment representing the alveolar lining fluid (ALF) was inserted into the lung of the standard whole body PBPK model exported from PK-Sim® (FIG. 2). The alveolar lining fluid contains the amount of dose deposited in alveolar space following inhalation. The volumes of the ALF compartment for the different species were calculated from literature values for the alveolar surface area and the thickness of the alveolar lining fluid (Tschumperlin and Margulies 1999, J. Appl. Physiol., 86: 2026-33; Patton 1996, Advanced Drug Delivery Reviews 19: 3-36; Bastacky et al. 1995, J. Appl. Physiol. 79: 1615-28). The volume of the ALF compartment was assumed to be constant after inhalation of aerosol due to fast reabsorption of inhaled water.

Also a diffusional exchange pathway connecting the alveolar space to the lung tissue (interstitium) was inserted into the model. The diffusion rate was calculated by the following first order equation:

$$dN/dt = P_{alv} * A_{alv} * (C_{alf} - C_{int})$$

with N: amount of drug $P_{alv}$: alveolar permeability (epithelial cell barrier). The parameter value was fitted to plasma concentration-time profiles following inhalation in rats.

$A_{alv}$: alveolar surface areas from literature.

$C_{alf}$: concentration of drug in ALF.

$C_{int}$: concentration of drug in lung interstitium.

Following inhalation, aerosol particles are deposited in various regions of the respiratory tract. To estimate the fraction deposited in the lower respiratory tract following inhalation of SEQ ID NO: 71, aerosol deposition for different paediatric age groups was scaled using a dedicated tool incorporated into the PBPK model, Multiple-Path Particle Dosimetry (MPPD) V2.11 (2002-2009, a detailed description can be found on http://www.ara.com/products/mppd.htm). The MPPD Model was developed by Applied Research Associates, Inc. and The Hamner Institutes for Health Sciences, USA, in collaboration with the National Institute of Public Health and the Environment (RIVM), The Netherlands, and the Ministry of Housing, Spatial Planning and the Environment, The Netherlands. It allows the description of the average regional depositions in the head, tracheobronchial and alveolar regions, and average deposition per airway generation, for different paediatric age groups, and for particles of different sizes. Overall, regional deposition depends on lung morphology (which is age specific), particle properties (size and density distribution) and breathing pattern (frequency, volume). As such, the MPPD tool calculates the deposition of aerosols in the respiratory tract of adults and children (ages: 3, 21, 23 and 28 months, 3, 8, 9, 14 and 18 years) for particles of different sizes. Deposition is calculated using theoretically derived efficiencies for deposition by diffusion, sedimentation and impaction within the airway or airway bifurcation. Filtration of aerosols by the head is determined using empirical efficiency functions.

Example 2: PBPK Model Evaluation: PBPK IV Model

PBPK IV models were established using the following information: i) compound-specific information on physicochemical characteristics of SEQ ID NO: 71, data from ii) an initial PK study in rats (Table B-1: study 1), data from iii) a toxicity study in rats (Table B-1: study 2) and iv) a cardiovascular safety pharmacology study in dogs (Table B-1: study 3) after IV administration. This first level of model building (IV models) considered distribution and clearance processes.

Figure 6:
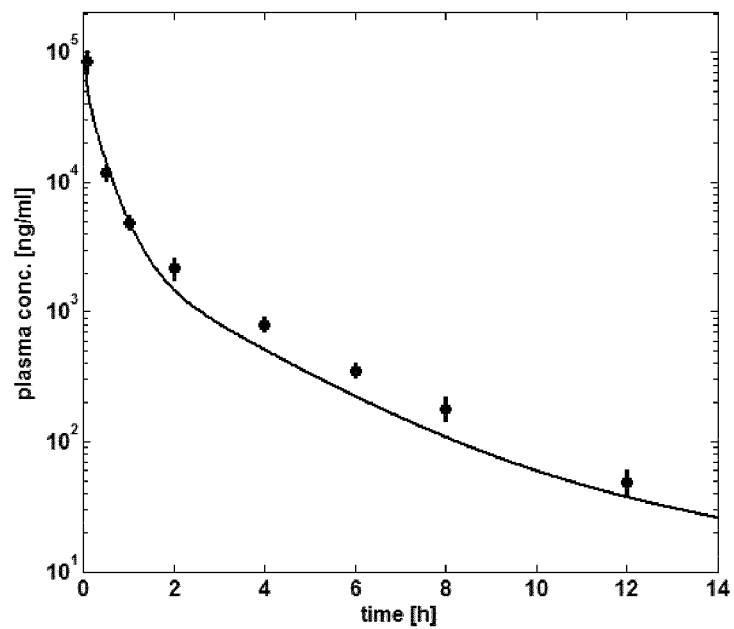
FIGS. 6A-6B are a pair of graphs providing a comparison of experimental vs. simulated plasma concentration-time profile of SEQ ID NO: 71 after (A) single dose IV application in rats (dose 5 mg/kg). Symbols: experimental data, line: simulation; (B) multiple dosing IV application in dogs (ascending dose of 3 mg/kg, 10 mg/kg, and 30 mg/kg). Symbols: experimental data, line: simulation.
Figure 6:
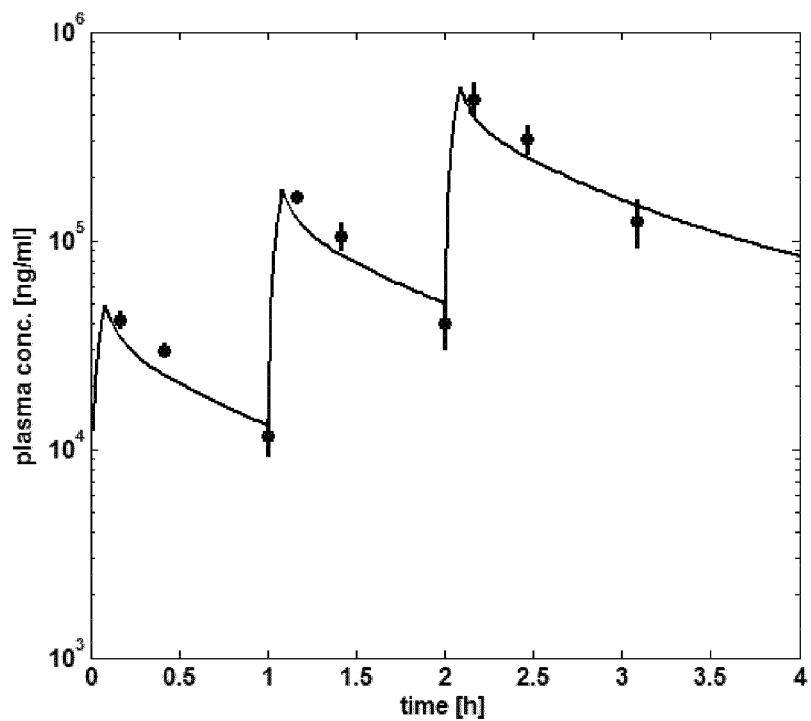

Two parameters, the hydrodynamic radius of SEQ ID NO: 71 and the renal clearance (CL), were estimated by fitting the experimental plasma concentration profiles (FIGS. 6A and B). The hydrodynamic radius of SEQ ID NO: 71 obtained was 2 nm which is smaller than the expected experimental value of 3.5 nm. The radius of 2 nm matches the radius of the monovalent unit of the trivalent polypeptide. The small drug radius obtained after the parameter identification might thus be explained by the flexibility of the polypeptide. In rats, best results were obtained with a renal CL of 58% of the glomerular filtration rate (GFR).

Example 3: PBPK Model Evaluation: Pulmonary Delivery in Rats

In order to account for the absorption process, pulmonary delivery was modelled in the second level of model building. The model for IV application using a hydrodynamic drug radius of 2 nm and a renal clearance of 58% of GFR as described in Example 2 was extended to pulmonary absorption by addition of a pulmonary compartment as described in Example 1. This part was established based on experimental plasma concentration-time profiles as well as local drug amounts in the lungs from single dose (Table B-1: study 1) and repeated dose toxicity studies (Table B-1: study 4) conducted in rats.

Figure 7:
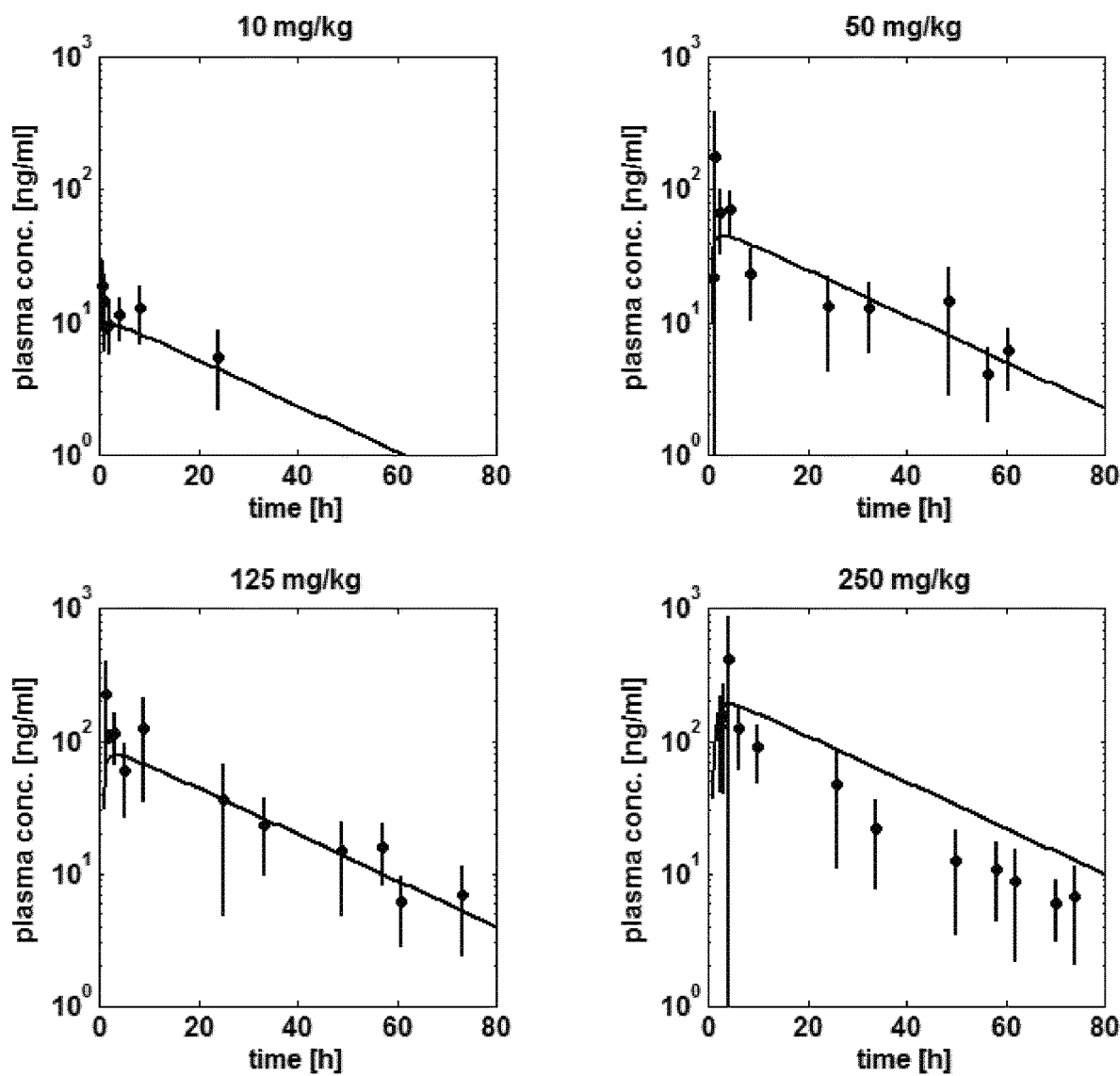
FIG. 7 is a series of graphs providing a comparison of experimental vs. simulated plasma concentration-time profiles of SEQ ID NO: 71 after pulmonary application in rats (Table B-1: study 1). Symbols: experimental data, line: simulation.

The alveolar permeability and the fraction of dose deposited in the alveolar absorption space were fitted to match the experimental plasma concentration-time profiles following pulmonary administration in rats (Table B-1: study 1) (FIG. 7). The experimental data matched well by simulation curves yielding an alveolar permeability $P_{alv}$ of 4.58E-9 cm/min and a fraction of dose deposited in the alveolar space of 0.37%.

Figure 8:
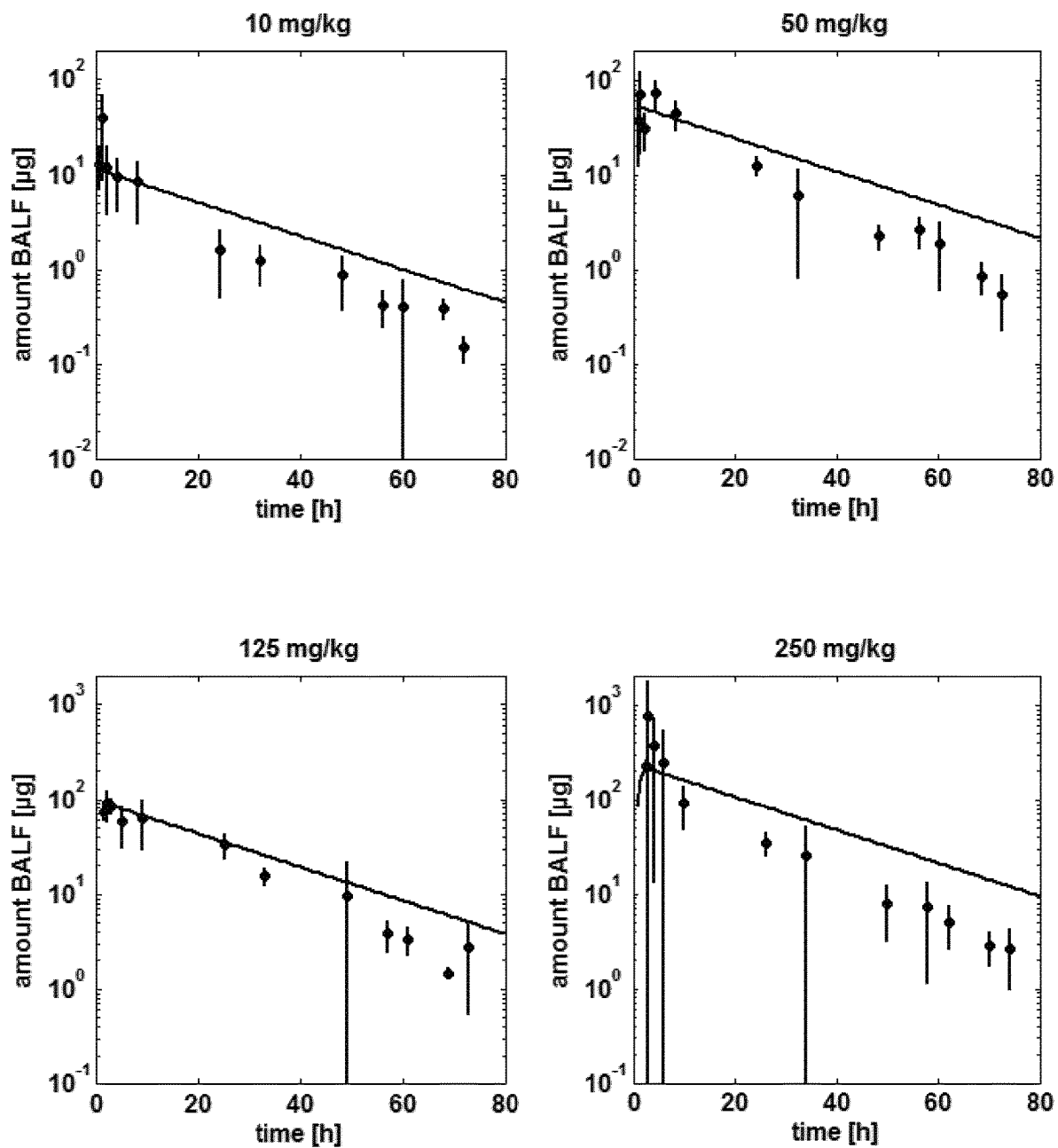
FIG. 8 is a series of graphs providing a comparison of experimental amount of SEQ ID NO: 71 in BALE after pulmonary application in rats (Table B-1: study 1) to simulated amount of SEQ ID NO: 71 in the alveolar absorption compartment. Symbols: experimental data (experimental BALF data from right lung were scaled to total lung according to weights of lung lobes), line: simulation.

The same model was used to compare the simulated amount of SEQ ID NO: 71 in the ALF absorption compartment to the amount experimentally found in the bronchoalveolar lavage fluid (BALF) (FIG. 8). For all doses, calculated amounts of SEQ ID NO: 71 matched the experimental values, with the simulated half-life being only slightly larger than the observed one.

For the simulation of the repeated dose study (Table B-1: study 4), the same value for the alveolar permeability was used as for the single dose study above (4.58E-9 cm/min).

Figure 9:
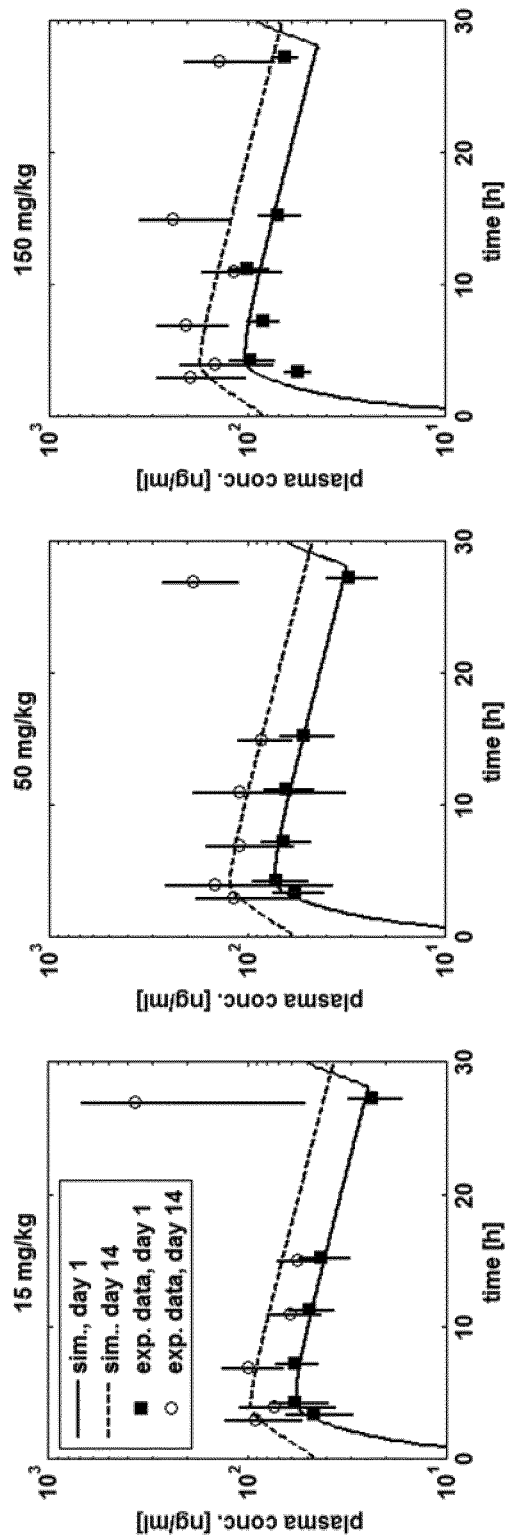
FIG. 9 is a series of graphs providing a comparison of experimental vs. simulated plasma concentration-time profiles of SEQ ID NO: 71 on day 1 and 14 after pulmonary application in rats (Table B-1: study 4). Symbols: experimental data, lines: simulation.
Figure 10:
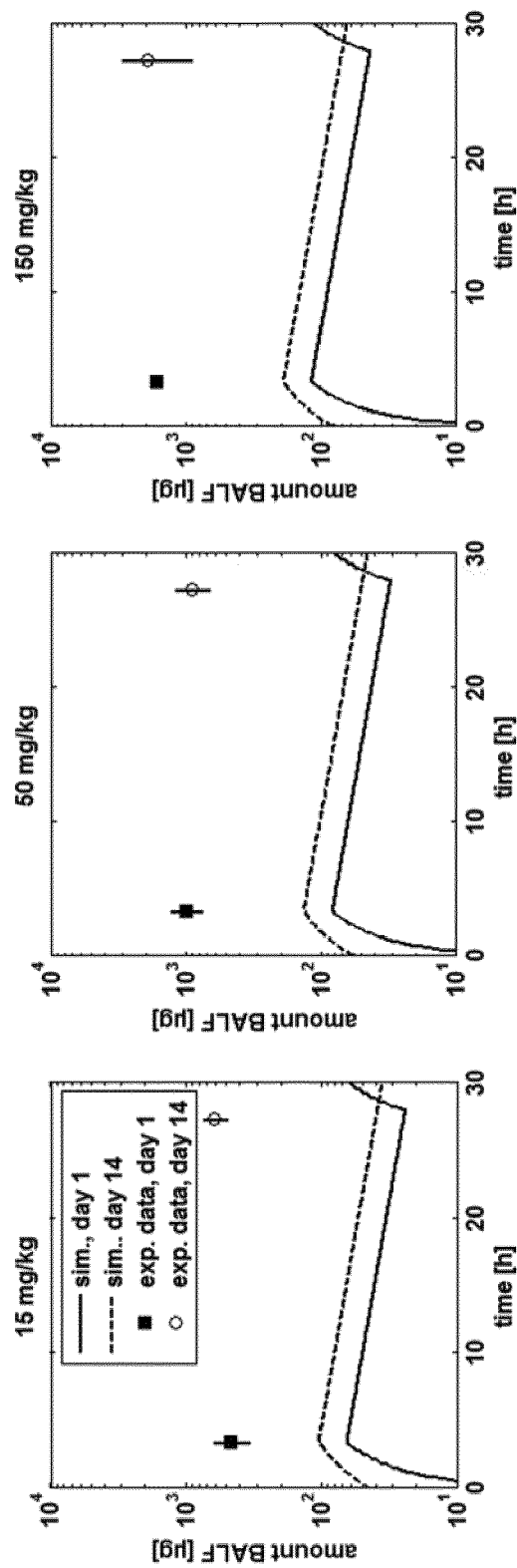
FIG. 10 is a series of graphs providing a comparison of experimental amount of SEQ ID NO: 71 in BALF after pulmonary application in rats (Table B-1: study 4) to simulated amount in the alveolar absorption compartment on day 1 and 14. Symbols: experimental data, line: simulation.
Figure 11:
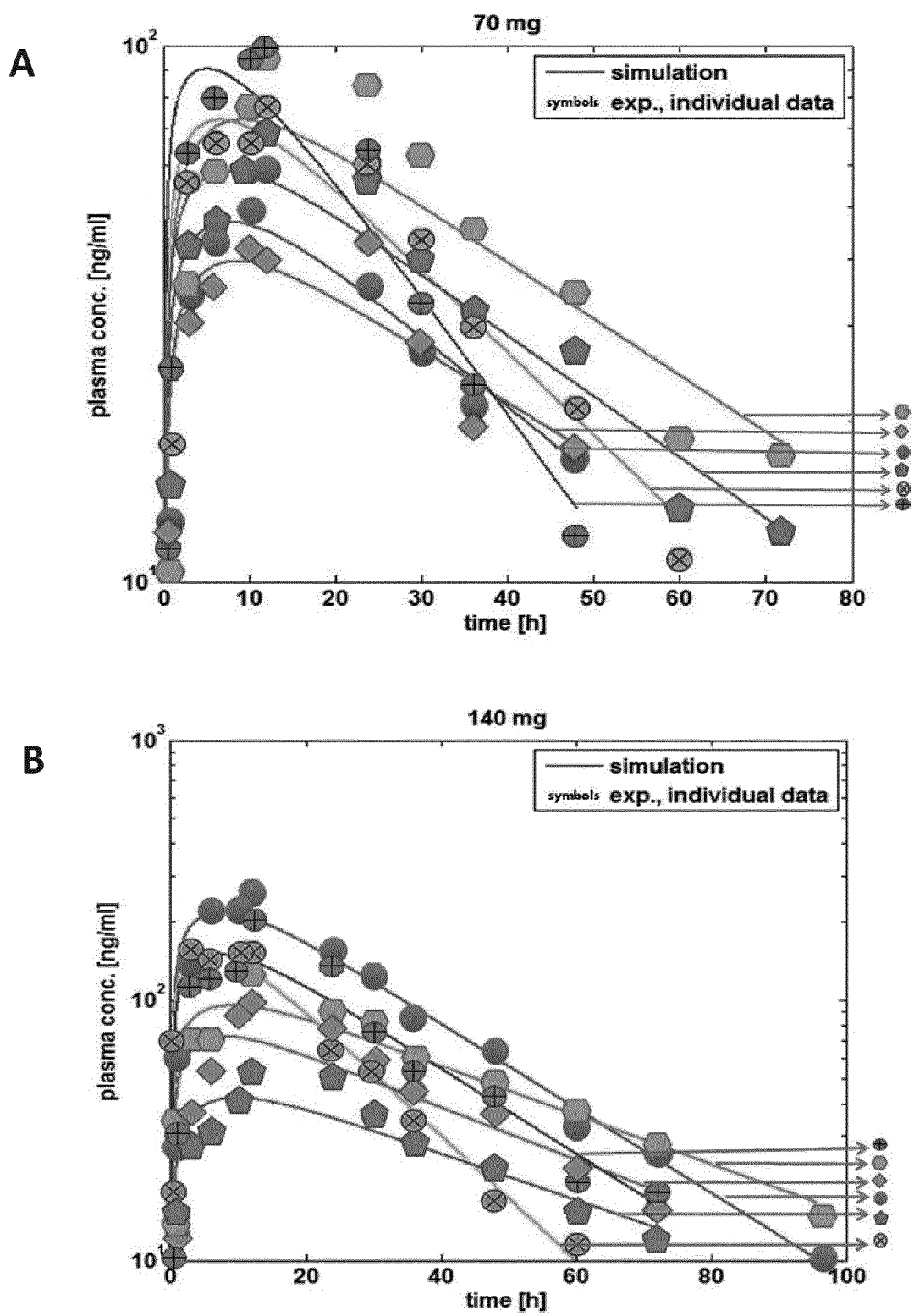
FIGS. 11A-11C are a series of graphs providing a comparison of experimental vs. simulated plasma concentration-time profiles for single individuals after pulmonary application of SEQ ID NO: 71 (Table B-2: study 5) at (A) 70 mg; (B) 140 mg; (C) 210 mg. Symbols: experimental data, line: simulation.
Figure 11:
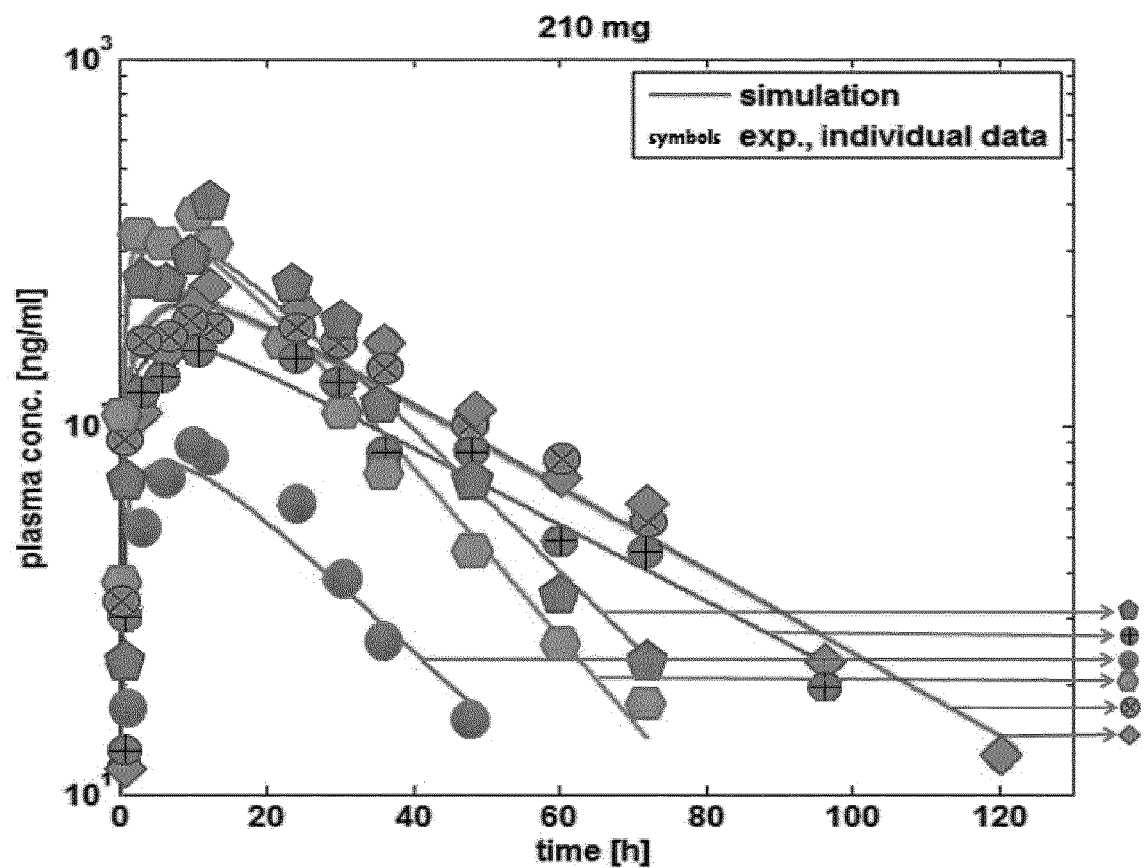
Figure 12:
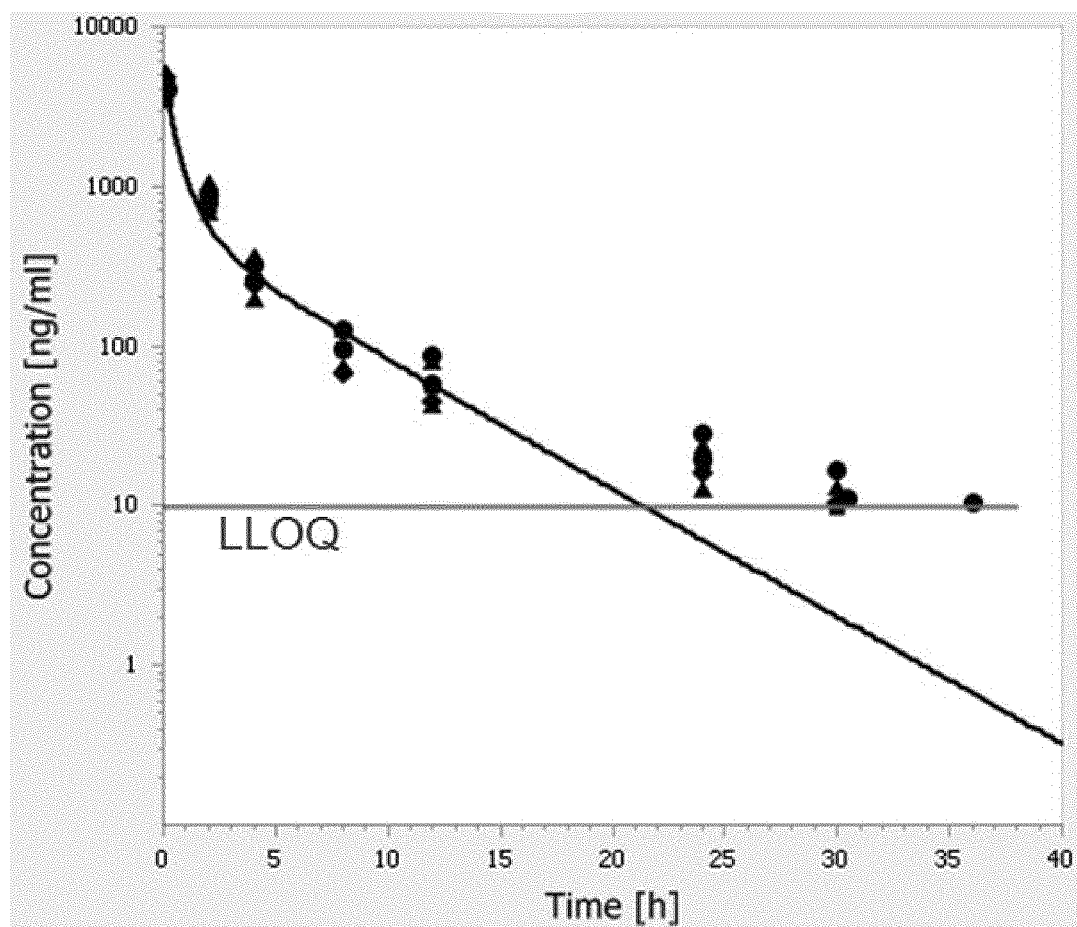
FIG. 12 is a graph providing a comparison of individual experimental plasma concentration-time profiles of SEQ ID NO: 71 following IV administration (Table B-1: study 6) to the simulation result of the human model scaled from rats. The grey line marks the LLOQ.
Figure 13:
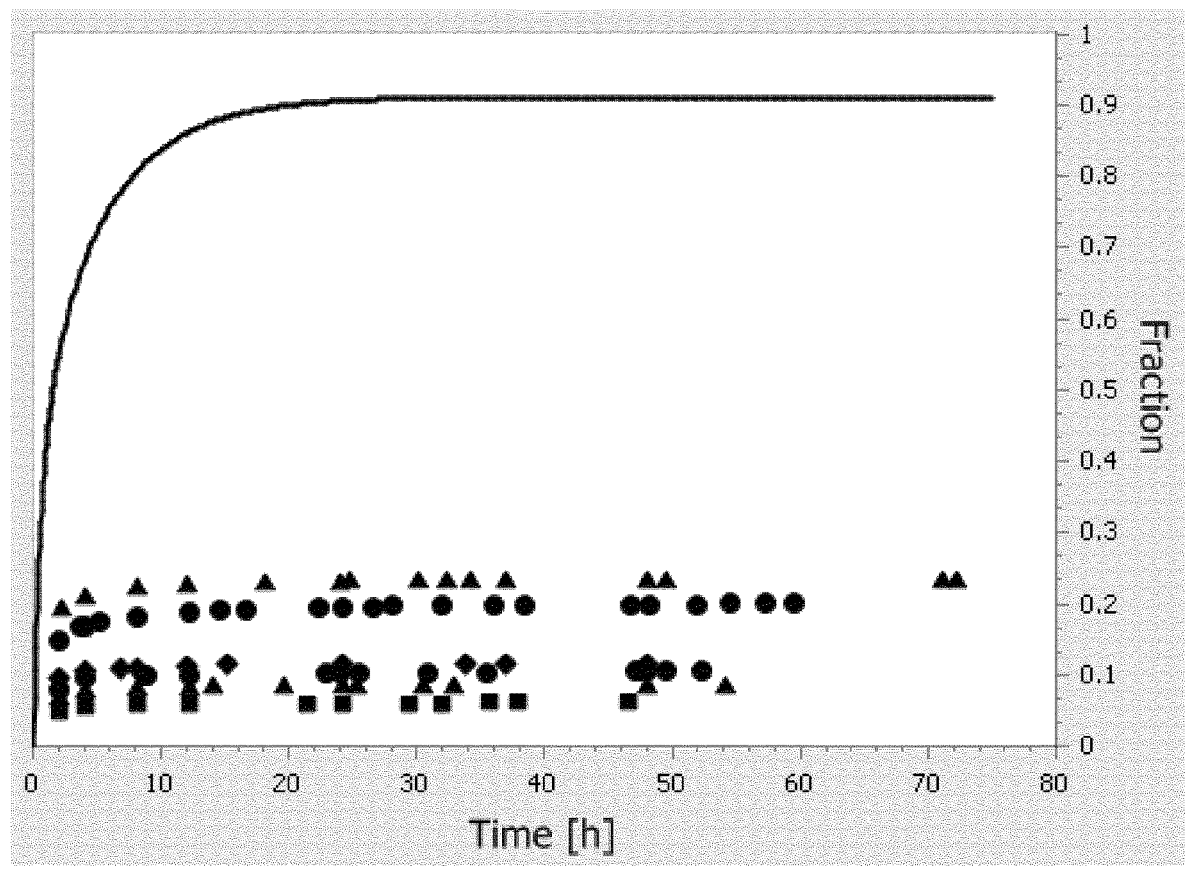
FIG. 13 is a graph providing a comparison of experimental individual cumulative fraction of dose excreted into urine following IV administration (Table B-1: study 6) to the simulation results of the human model scaled from rats.
Figure 14:
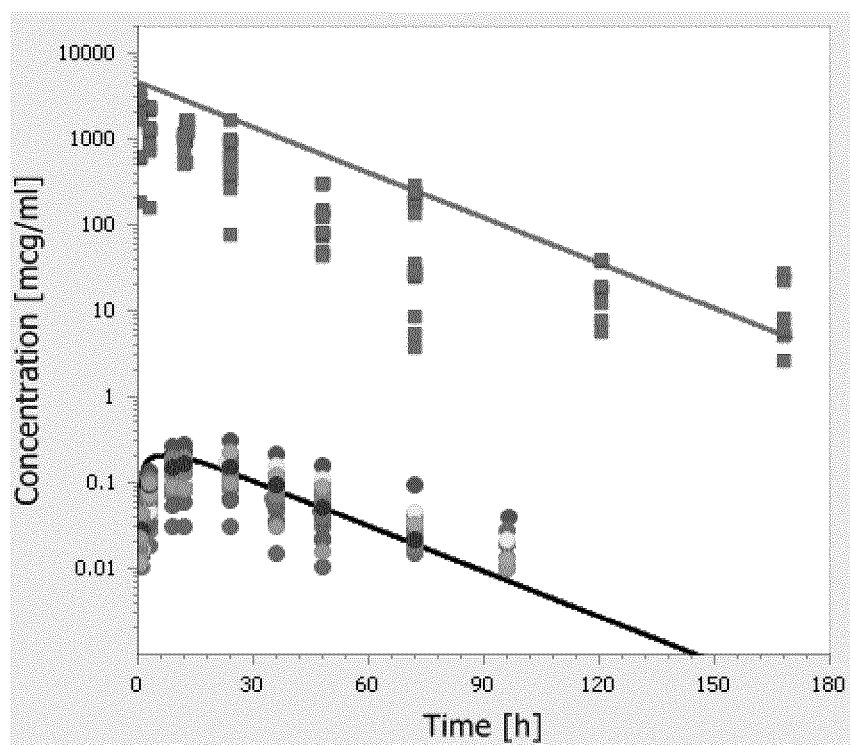
FIGS. 14A-14B are a pair of graphs providing a comparison of individual experimental plasma (circles) and ALF (squares) concentration-time profiles of SEQ ID NO: 71 following single dose inhalation (A) and multiple dose inhalation (B) from the second clinical study (Table B-1: study 6) to the simulation results (lines) of the human model scaled from rats.
Figure 14:
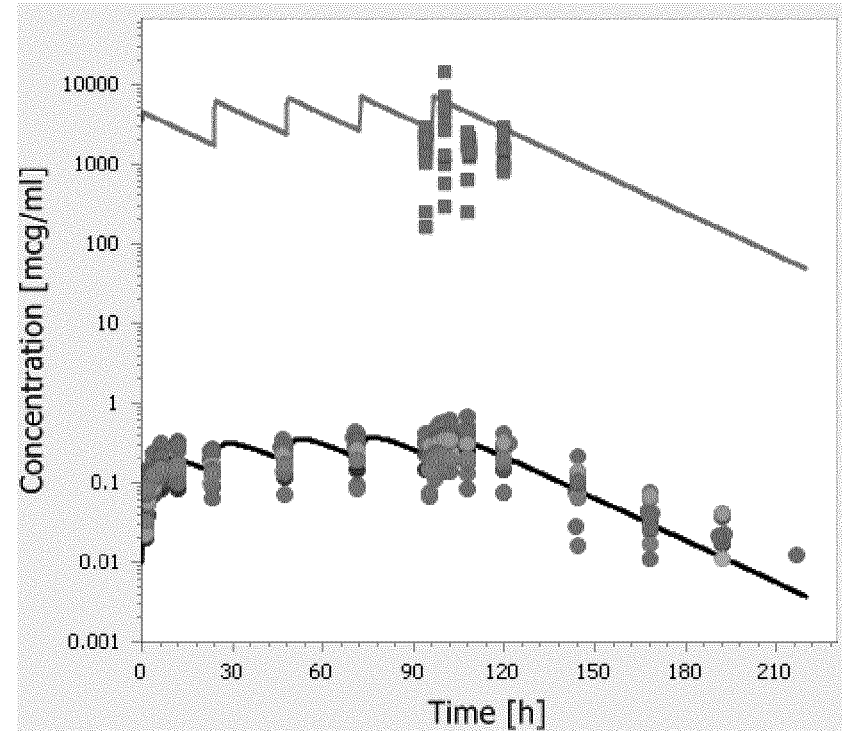

Simulation of plasma concentration curves of SEQ ID NO: 71 after pulmonary application once daily for 14 days yielded an excellent match with experimental data on day 1 and day 14 (FIG. 9) after adjusting the fraction of dose deposited in the alveolar absorption space. In contrast to the previous study, different values for the fraction of the dose deposited needed to be assumed to obtain reasonable fits (1.8% for 15 mg/kg, 0.93% for 50 mg/kg and 0.47% for 150 mg/kg). The tendency of smaller alveolar deposition with increasing aerosol particle diameter may explain the different plasma PK curves for the different dose groups.

The simulated amounts in the ALF absorption compartment using the same model as in FIG. 9 were compared to the amounts experimentally found in the bronchoalveolar lavage fluid (BALF) (FIG. 10). The simulated curves deviated strongly (one order in magnitude) from the experimental amounts. This discrepancy might be explained by the contributions from trachea/bronchi in the BALF data, as the experimental amount in BALF contains contributions from the whole respiratory tract, while the simulated amount refers only to the amount in the alveolar absorption space. The deviation between experiment and simulation is much larger than in the study 1. This might be explained by a larger drug recovery in study 4, possibly due to the different BALF sampling procedures (whole lung including trachea in study 4, right lung in study 1). The accumulation/half-live of the experimental BALF data was well described by the simulations and was similar to the accumulation/half-life in plasma.

Example 4: PBPK Model Evaluation: Pulmonary Administration in Healthy Adult Human 4.1 First Clinical Study (Table B-1: Study 5)

Safety, tolerability and PK of inhalation of SEQ ID NO: 71 were initially evaluated in a Phase I study in healthy male volunteers (Table B-1: study 5). The Phase I study included a single-ascending dose part in 44 subjects, in which six dose levels ranging from 2.1 mg to 210 mg were tested. Subsequent, a multiple dose part was initiated in 16 healthy males, in which the subjects received SEQ ID NO: 71, twice daily at a total daily dose of 150 mg and 210 mg respectively, for five days.

4.2 Model Evaluation

The PBPK model in rats was scaled to humans by adapting physiological parameters such as organ volumes, blood and lymph flow in organs from the human PK-Sim® database. The hydrodynamic radius of SEQ ID NO: 71 and the renal CL were set to 2 nm and 58% of GFR as in all previous calculations in rats. The alveolar absorption was described by the same mechanism as in rats. The thickness of the ALF and the alveolar permeability were assumed to be the same as for rats whereas the alveolar surface area was scaled to 102.2 $m^2$ (Patton 1996, Advanced Drug Delivery Reviews 19: 3-36).

The human plasma PK data from this first clinical study in humans (Table B-1: study 5) were used to evaluate the model and scaling rationale. The fraction deposited in the alveolar space had to be fitted to the experimental data. However, variation of this parameter (equivalent to a variation in the effective dose) resulted only in a shift of the simulated profile along the concentration axis while the shape of the profile was conserved. Thus, the simulations had predictive character for the concentration profile including the terminal half-life determined by the absorption rate.

In FIG. 11 the simulated plasma concentration-time profiles of SEQ ID NO: 71 were compared to experimental data from single healthy volunteers after pulmonary administration of SEQ ID NO: 71. Best fitting results were obtained using a value of 15% for the fraction of dose deposited in the alveolar space. FIG. 11 shows that the absorption rate in healthy human volunteers was predicted very well by the PBPK model scaled from the rat model and that therefore in humans the same value for the alveolar permeability can be assumed as in rats.

Example 5: PBPK Model Evaluation: IV and Pulmonary Administration in Healthy Adult Human 5.1 Second Clinical Study (Table B-1: Study 6)

Another phase I study was performed to assess the PK of single and repeated doses of SEQ ID NO: 71, administered by inhalation to healthy adult male volunteers. Single i.v. administration of SEQ ID NO: 71 was also included in the study, to provide additional information for subsequent PK modeling and simulations. Forty-four subjects were randomized and treated: 23 subjects with SEQ ID NO: 71 single dose inhalation, 15 subjects with SEQ ID NO: 71 multiple dose inhalation, and 6 subjects with SEQ ID NO:71 i.v. infusion. The study investigated the concentration of SEQ ID NO: 71 locally (in the bronchial and alveolar space) and/or systemically when administered by oral inhalation or intravenous administration.

5.2 Model Evaluation

The model was further validated and refined with urinary and alveolar lining fluid (ALF) data from the second clinical trial after IV and pulmonary administration (Table B-1: study 6).

The same human model which was evaluated using the first clinical (Table B-1: study 5), was compared to the plasma concentration-time curves and urinary excretion data after IV administration of the second clinical study (Table B-1: study 6).

The simulations with the human model scaled from rats matches the experimental IV data very well for the first 12 hours after administration. The experimental data points 24 h after administration, however, were underestimated by the simulation and also the later time points seem to be underestimated (FIG. 12).

The amount of drug found experimentally in urine (6-23%) was much less than in the simulation (91%) (FIG. 13). Thus, the renal clearance of the model (58% of GFR) seemed to be too large. Under consideration of the urinary data which became available in this second clinical study (Table B-1: study 6), the renal clearance of the model had to be reduced. In order to still describe the plasma concentration time curve, an additional clearance process had to be introduced to the model.

The originally developed mean human model was also evaluated with inhalation data from the second clinical study (Table B-1: study 6) (FIG. 14). The original model was used without any changes (including the 15% fraction of dose deposited in alveolar space). The experimental ALF concentrations used for comparison were corrected using the urea dilution method (Conte et al. 1995, Antimicrob. Agents Chemother. 39: 334-8).

The simulated plasma concentration-time curve after inhalation matched the experimental data well. In the initial phase the experimental plasma concentrations were slightly underestimated. In the initial phase, also the experimental plasma concentrations from the first clinical study (Table B-1: study 5) were slightly lower than those from the second clinical study (Table B-1: study 6). Also the simulated ALF concentrations are in agreement with the experimental data, although the experimental data were slightly overestimated, i.e. the mean model matched the higher individual ALF concentrations.

Example 6: PBPK Model Refinement 6.1 Model Refinement

The following model characteristics were refined following the model evaluation:
1. The hydrodynamic radius was adapted in order to better describe the plasma concentration-time profile for time points later than 24 h after IV administration.
2. The renal clearance was reduced in order to match the experimentally observed fraction of dose in urine. For proteins with a size of approximately 40 kDa a renal clearance <10% is reported in literature (Galaske et al. 1979, Kidney Int. 16: 394-403; Maack et al. 1979, Kidney Int. 16: 251-70), justifying the reduction of renal clearance. In order to be able to still describe the observed plasma concentration profile after IV administration, an additional first order clearance process within all plasma compartments was added in the model. The additional clearance process can be attributed to plasma proteases. The first order rate constant was fitted to the plasma concentration profile after IV administration.
3. For the inhalation model, an alternative literature value for the alveolar thickness was used to better describe the ALF concentrations after inhalation. In the originally established models, an alveolar thickness of 0.068 µm was used as cited in the review by Patton 1996 (Advanced Drug Delivery Reviews 19: 3-36). A value of 0.2 µm was used in the refined model. This alternative value was likewise cited by Patton. The same value was reported independently as area-weighted average of the alveolar thickness for rat (Dall'Acqua et al. J. Biol. Chem. 281: 23514-24). Using the larger thickness of 0.2 µm results in an increased alveolar volume and consequently in decreased alveolar concentrations. If the alveolar permeability was increased correspondingly, the overall absorption rate and thus the systemic concentrations did not change. Thus, in the refined model the following scaled alveolar permeability was used: 4.58E-9 cm/min×0.2/0.068=1.35E-8 cm/min.

Figure 15:
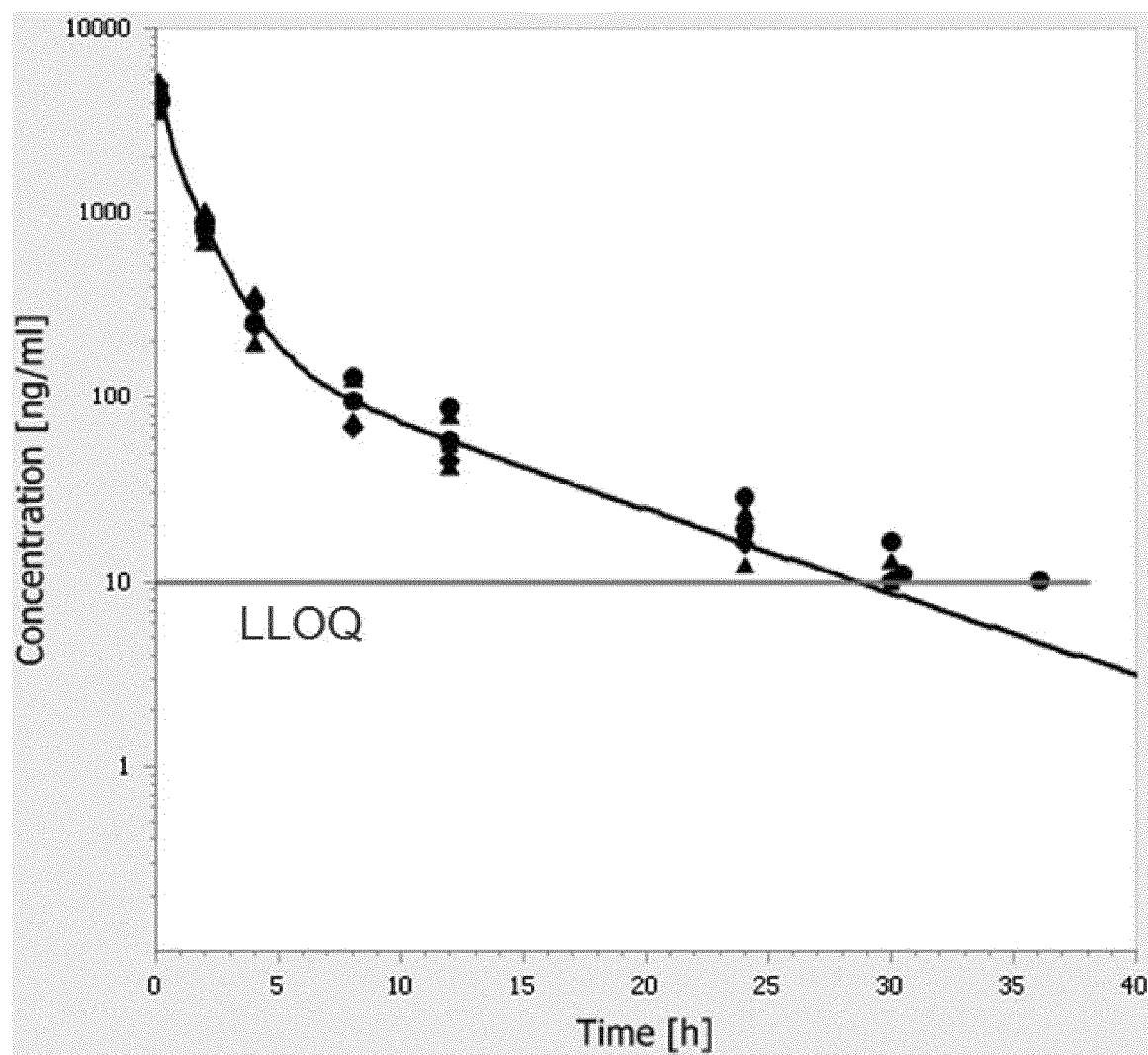
FIG. 15 is a graph providing a comparison of individual experimental plasma concentration-time profiles of SEQ ID NO: 71 following IV administration (Table B-1: study 6) to the simulation results of the refined human IV model (hydrodynamic radius: 2.46 nm; renal clearance: 5% of GFR and additional plasma clearance process). The grey line marks the LLOQ.
Figure 16:
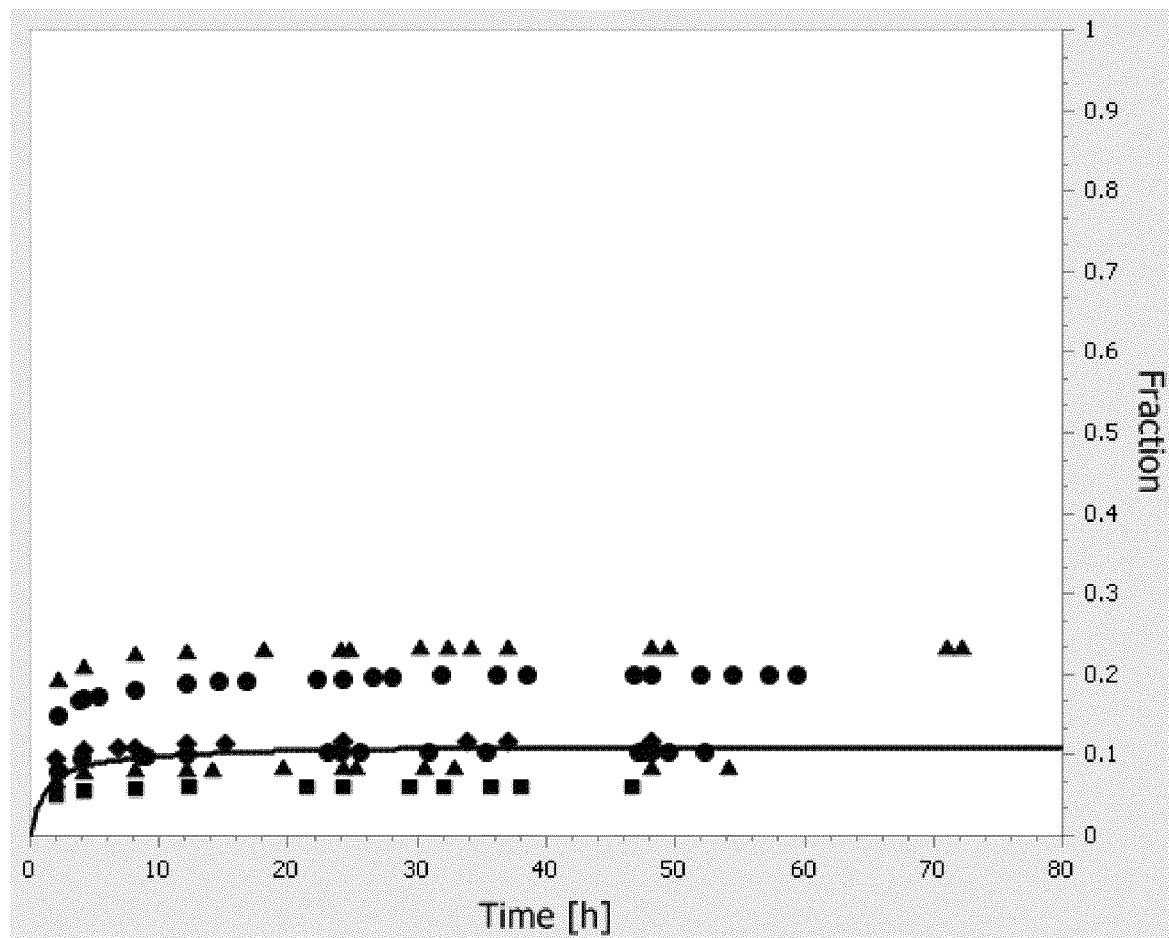
FIG. 16 is a graph providing a comparison of experimental individual cumulative fraction of dose excreted into urine following IV administration (Table B-1: study 6) to the simulation results of the refined human IV model (hydrodynamic radius: 2.46 nm; renal clearance: 5% of GFR and additional plasma clearance process).

Simulations performed with the refined model yielded mean plasma and urine concentration-time profiles that matched the experimental data of the second clinical study (Table B-1: study 6) very well (FIGS. 15 and 16). For the fitted hydrodynamic radius a value of 2.46 nm was obtained, for the renal clearance a value of 5% of GFR and for the additional plasma clearance rate constant of 0.0142 min$^{-1}$.

Figure 17:
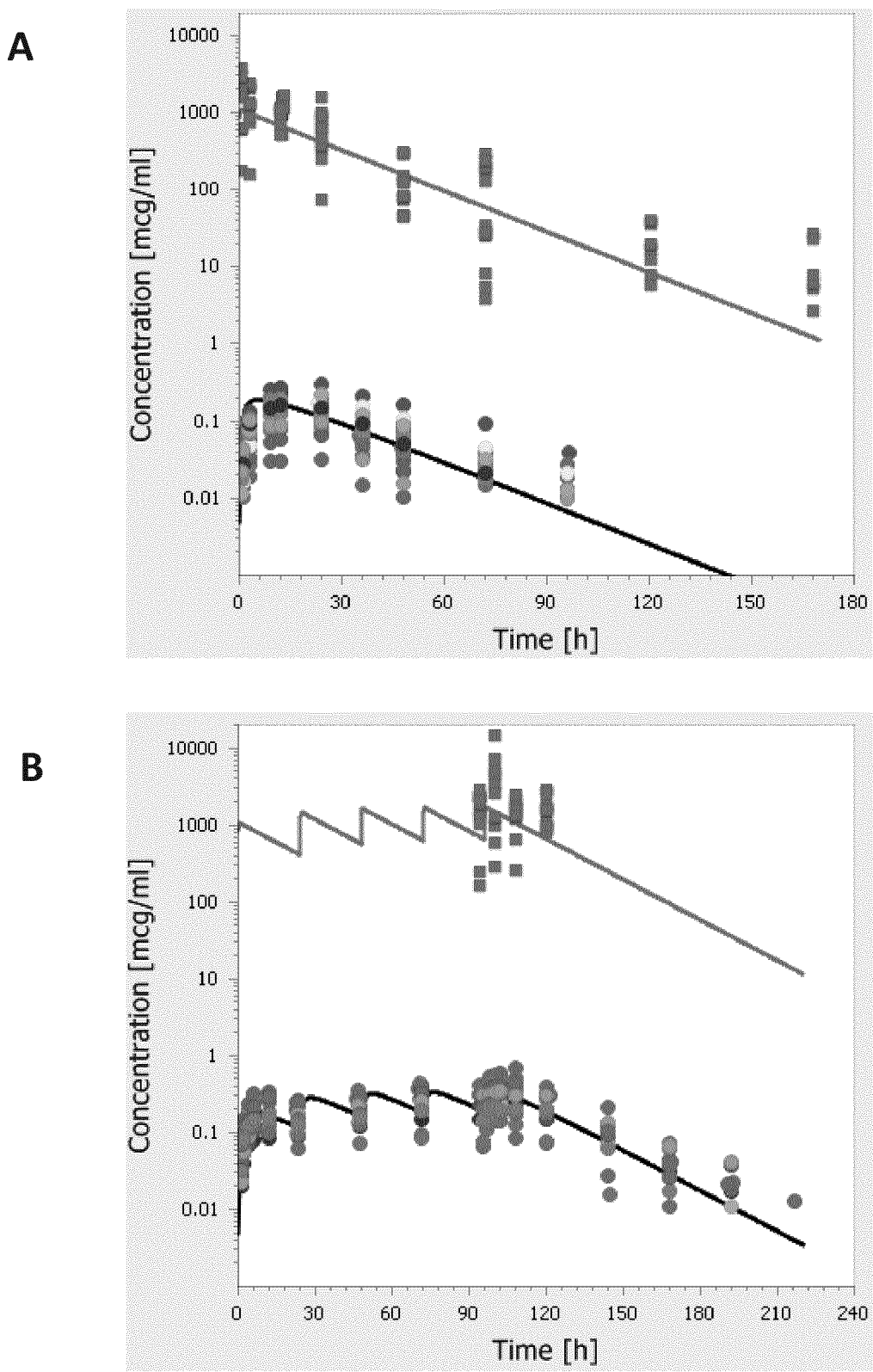
FIGS. 17A-B are a pair of graphs providing a comparison of individual experimental plasma (circles) and ALF (squares) concentration-time profiles of SEQ ID NO: 71 following single dose inhalation (A) and multiple dose inhalation (B) from the second clinical study (Table B-1: study 6) to the simulation results (lines) of the refined human model for inhalation (hydrodynamic radius: 2.46 nm, renal clearance: 5% of GFR, additional plasma clearance process, and alternative value for the alveolar thickness: 0.2 µm).

Using the alternative literature value for the alveolar thickness, the experimental ALF concentrations were described very well (FIG. 17). For the simulations with the refined model, the fraction of dose deposited in the alveolar space was additionally slightly adapted (10.6%) in order to obtain a better description of the plasma concentrations.

6.2 Population Simulation with Refined Model

To evaluate population simulations for the refined adult model, population simulation results were compared to the PK data from the second clinical study (Table B-1: study 6) as well as for the first clinical studies (Table B-1: study 5). Populations comprising of 1000 male individuals of the European ICRP2002 population were generated possessing demographic parameters uniformly distributed within the ranges from the two studies.

Figure 18:
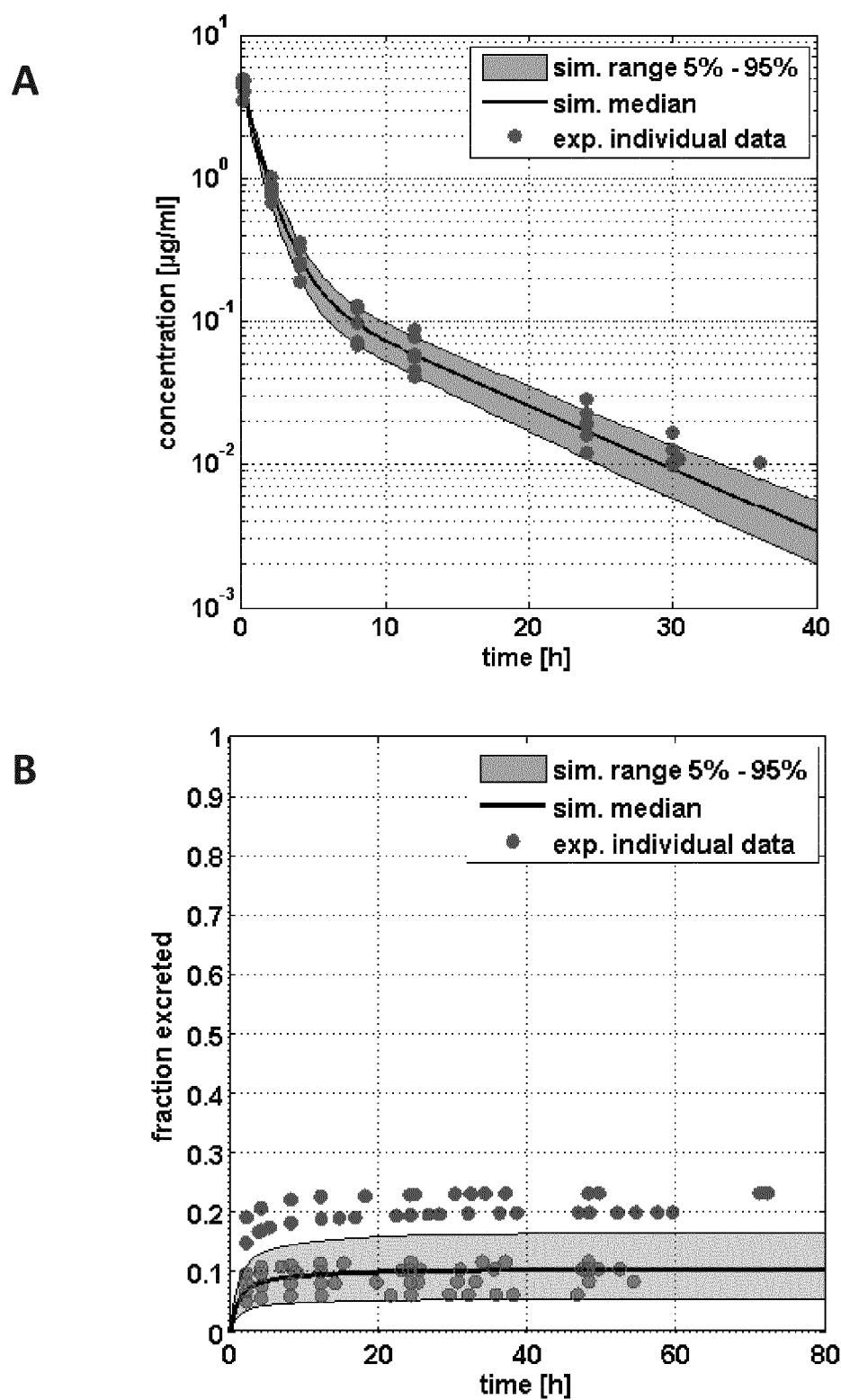
FIGS. 18A-18B are a pair of graphs providing a comparison of individual experimental plasma concentration-time profiles (A) and cumulative urinary excretion (B) of SEQ ID NO: 71 vs. results from a population simulation after IV application (Table B-1: study 6). Shaded area: $5^{th}$-$95^{th}$ percentile of population simulation, solid line: median of population simulation, circles: individual experimental data.

Comparison of individual experimental plasma concentration-time profiles and cumulative urinary excretion of SEQ ID NO: 71 (Table B-1: study 6) vs. results from a population simulation after IV application are shown in FIG. 18.

Figure 19:
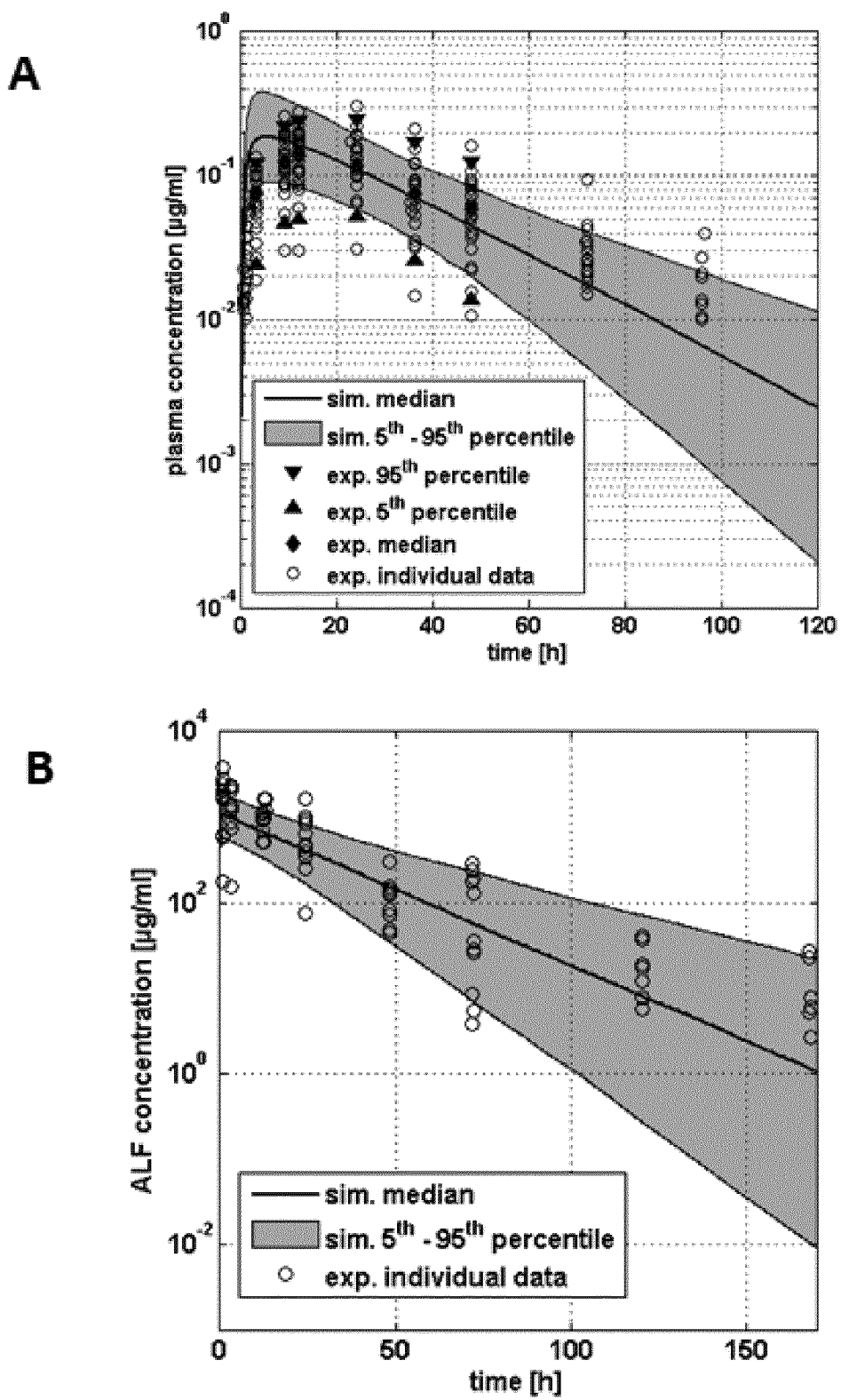
FIGS. 19A-19B are a pair of graphs providing a comparison of individual experimental plasma (A) and ALF (B) concentration-time profiles of SEQ ID NO: 71 vs. results from a population simulation for the second clinical study (Table B-1: study 6), for single dose pulmonary application. Shaded area: 5th-95th percentile of population simulation, solid line: median of population simulation, open circles: individual experimental data. Filled symbols (plasma profile): Median, 5th and 95th percentile of the experimental data (only shown if data for all individuals (n=23) were available).
Figure 20:
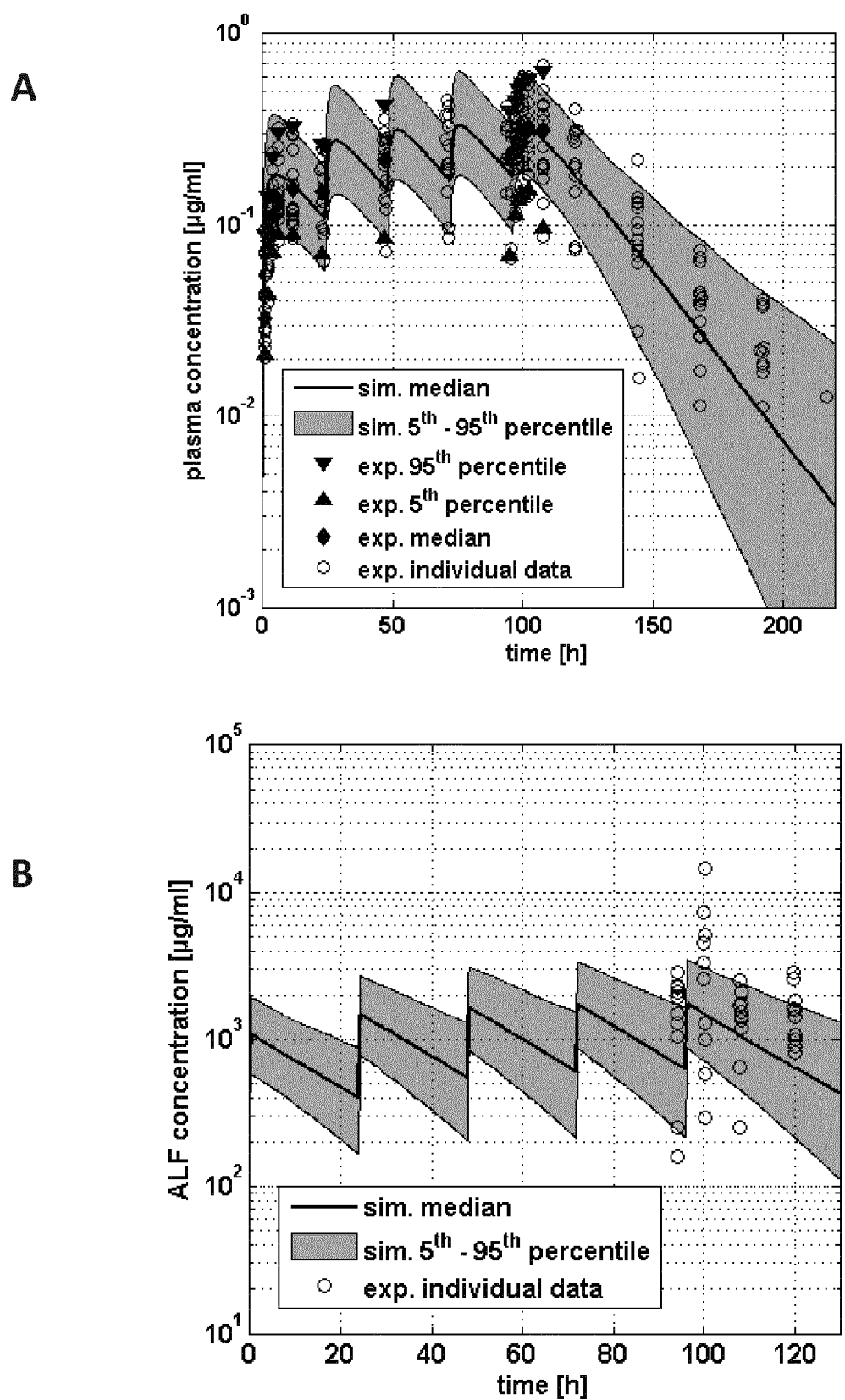
FIGS. 20A-20B are a pair of graphs providing a comparison of individual experimental plasma (A) and ALF (B) concentration-time profiles of SEQ ID NO: 71 vs. results from a population simulation for the second clinical study (Table B-1: study 6), for multiple dose pulmonary application. Shaded area: 5th-95th percentile of population simulation, solid line: median of population simulation, open circles: individual experimental data. Filled symbols (plasma profile): Median, 5th and 95th percentile of the experimental data (only shown if data for all individuals (n=15) were available).

Comparisons of population simulations to experimental plasma and ALF concentrations after single inhalation and multiple inhalations from the second human study (Table B-1: study 6) are shown in FIG. 19 and FIG. 20, respectively.

Figure 21:
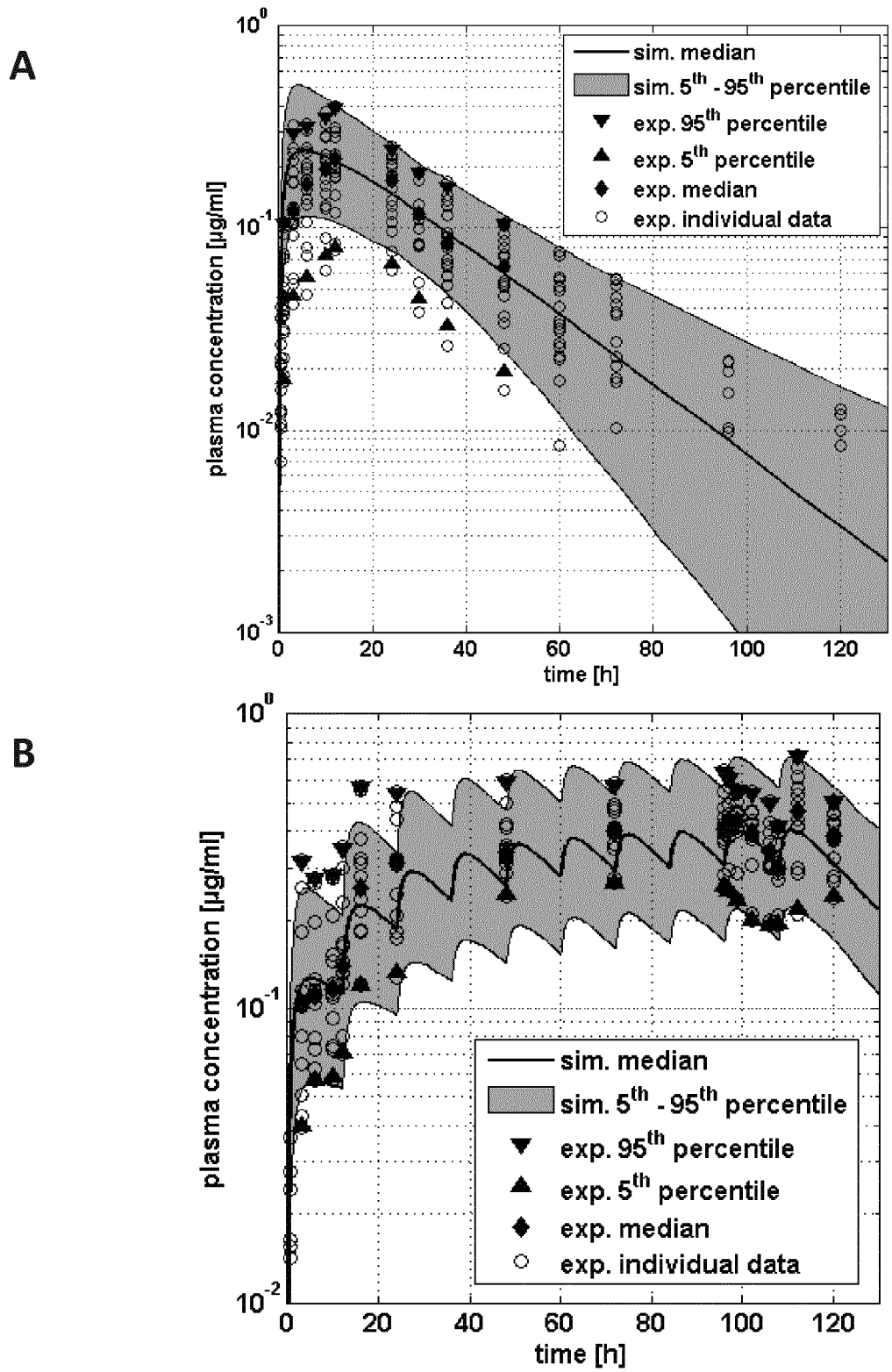
FIGS. 21A-21B are a pair of graphs providing a comparison of individual experimental plasma concentration-time profiles of SEQ ID NO: 71 vs. results from a population simulation for single dose inhalation (A) and multiple dosing inhalation (B) for the first human study (Table B-1: study 5). Shaded area: $5^{th}$-$95^{th}$ percentile of population simulation, solid line: median of population simulation, open circles: individual experimental data, filled symbols: Median, $5^{th}$ and $95^{th}$ percentile of the experimental data (only shown if data for all individuals were available, n=18 for single dosing and n=12 for multiple dosing).

Population simulations using the refined model were also re-evaluated by comparing to the data from the first human study (Table B-1: study 5) (FIG. 21).

For both studies, the population simulations agree reasonably well the experimental data.

Example 7: Scaling of Adult PBPK Model to Healthy Children

The refined adult PBPK model was subsequently extrapolated to children by scaling (i) anatomical and physiological parameters, (ii) the clearance processes, and (iii) the absorption process, largely based on established parameters and equations available from literature (Edginton et al. 2006, Clin. Pharmacokinet. 45: 1013-1034; Rhodin et al. 2009, Pediatr. Nephrol. 24: 67-76; Hislop et al. 1986, Early Hum. Dev. 13: 1-11).

Figure 4:
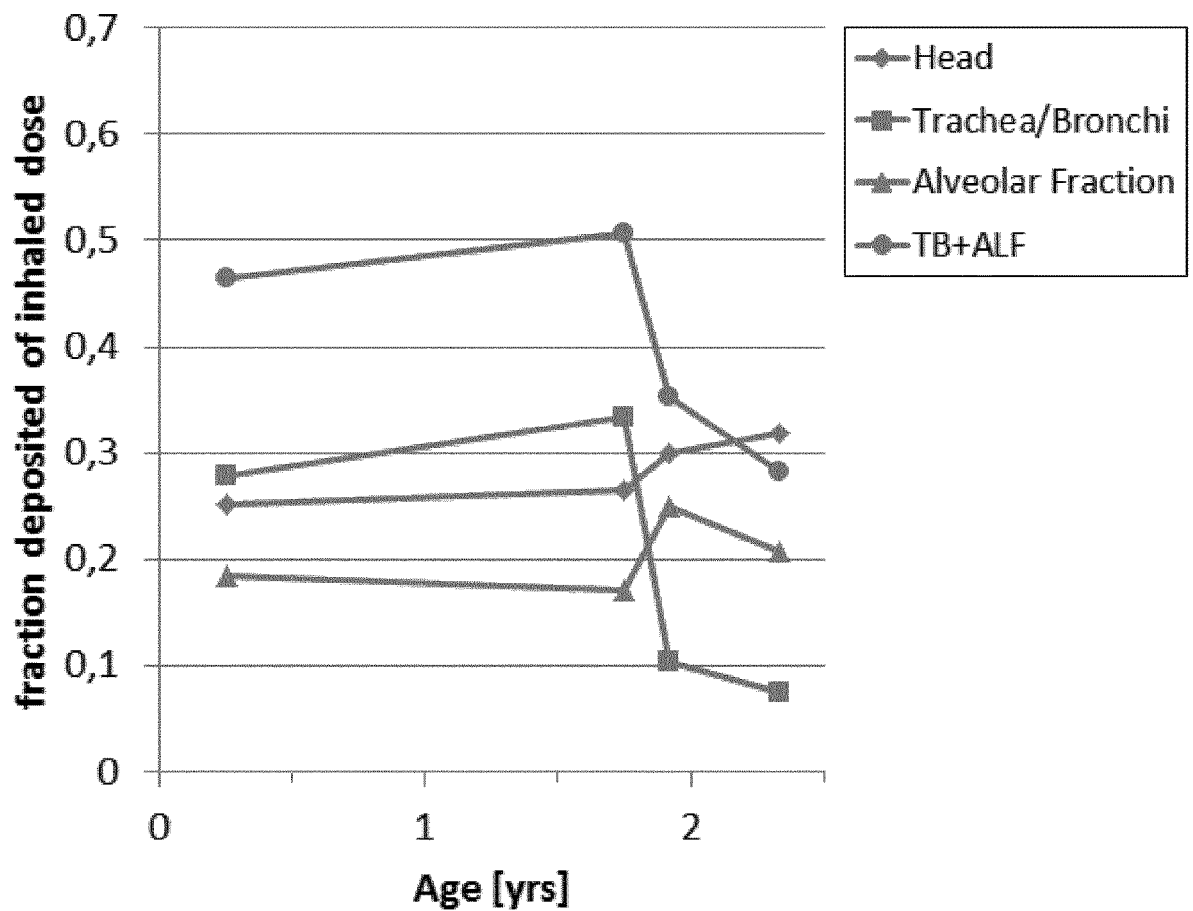
FIG. 4 is a graph depicting the fraction of inhaled dose deposited in the different regions of the respiratory tract as calculated with the MPPD tool for quiet nasal inhalation. Age specific lung model: 3 months, 21 months, 23 months and 28 months.

To estimate the fraction of inhaled dose deposited in the alveolar absorption space, the MPPD tool was used. The ages 3 months, 21 months, 23 months and 28 months are available within the MPPD tool. The particle size distribution used was 2.63 µm MAD (mass median diameter) and a geometric standard deviation of 1.46. A quiet nasal inhalation was used for the breathing parameters. For the other parameters the MPPD default settings were used. The fraction of inhaled dose in the alveolar space was calculated to be around 20% (FIG. 4).

The pediatric PK-Sim populations with standard variability of anthropometric and physiological parameters (e.g. organ volumes, blood flows, GFR) were used. Virtual Caucasian populations for eight age groups each with 1000 individuals and an even ratio of both genders were generated to estimate the population pharmacokinetics. The age groups were: 0-1 weeks, 1-2 weeks, 2-4 weeks, 1-3 months, 3-6 months, 6-9 months, 9-12 months, 12-24 months, 2-3 years, 3-4 years, 4-5 years and 5-6 years (preterm born children excluded).

Three additional parameters were varied in the population simulation: the alveolar permeability, the fraction of dose deposited in alveolar space and the additional plasma clearance process. For all three parameters a lognormal distribution was assumed. For the alveolar permeability (geometric mean: 1.35E-8 cm/min) a geometric standard deviation of 1.4 was used as estimated from the individual fits to the first human adult clinical study (Table B-1: study 5). The dose in the alveolar space was chosen as to reach the alveolar target concentration. A geometric standard deviation of 2 was used for the fraction of dose in alveolar space for all age groups. A once daily inhalation for 5 days was used as application schema for the simulations (inhalation time: 3 min for each inhalation). For each administration of the multiple dose scheme, the value of the fraction of dose in alveolar space was taken from the distribution independently from the values for the other administrations. For the additional plasma clearance a geometric standard deviation of 1.1 was used as for the adult populations (geometric mean: 0.0142 min$^{-1}$).

Figure 22:
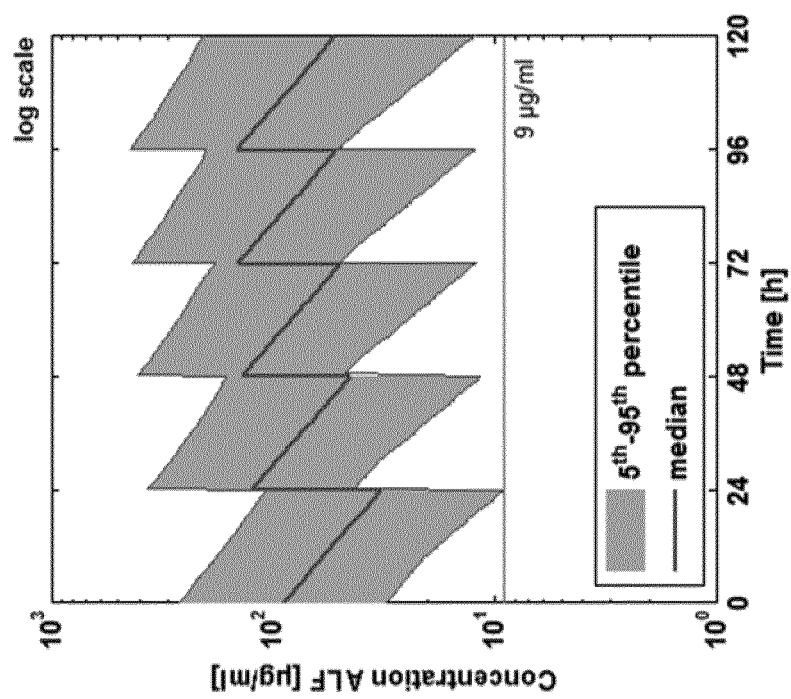
FIGS. 22A-22B are a pair of graphs providing an ALF concentration-time curve for the group 0-1 week old children. The grey line marks the target concentration of 9 µg/ml. A: linear concentration scale; B: log concentration scale.
Figure 22:
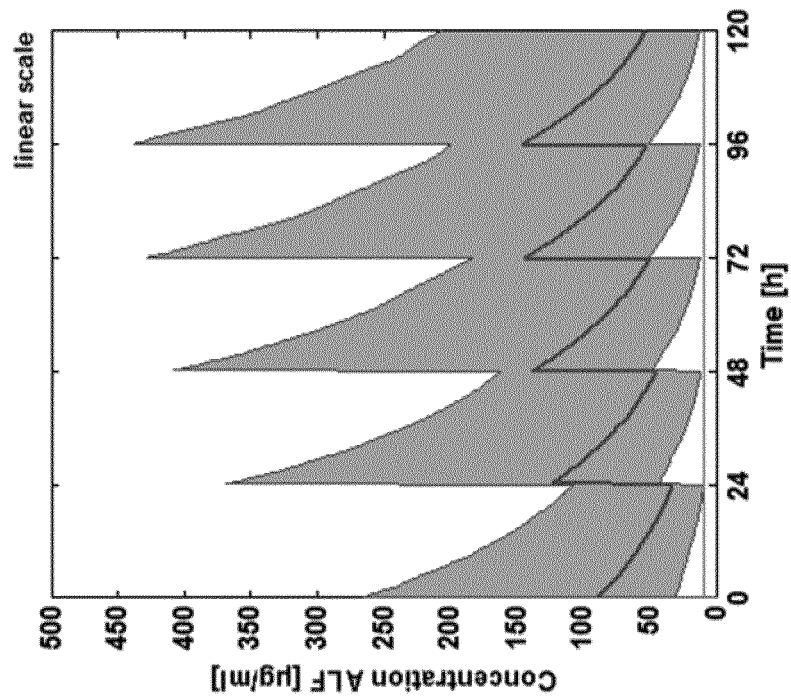

According to the modelling objective, the dose was chosen to reach at least 9 µg/mL (100*IC90) for 95% of the individuals for the whole dosing interval. Regarding dose, the primary important parameter driving systemic as well as local PK in the PBPK model appeared to be the amount of drug in alveolar absorption space. Based on the PBPK simulations, the target concentration of 9 µg/ml was reached using an amount of 0.024 mg/kg body weight (deposited dose) in the alveolar space for all age groups. Since the alveolar surface area and with that, the alveolar volume, scaled with the body weight, the alveolar concentration was virtually not age dependent for a body weight normalized dose. A deposited dose of 0.024 mg/kg body weight in the alveolar absorption space was thus used for all simulations of the plasma concentrations (FIG. 22).

Example 8: Scaling of Adult PBPK Model to Diseased Children

The adult PBPK model was then scaled to diseased children, to account for potential physiological differences related to the disease. Since literature data directly comparing RSV-infected vs. healthy children are sparse, a sensitivity analysis was performed for the key parameters adapted/fitted during the model development process (fraction deposited in the alveolar space, clearance, alveolar permeability, thickness of the alveolar space, and hydrodynamic drug radius). Based on the available nonclinical results, the available literature (Kilani et al. 2004, Chest 126: 186-91; Singh et al. 2007, Am. J. Physiol. Lung Cell Mol. Physiol. 293: L436-45; Domachowske and Rosenberg 1999, Clin. Microbiol. Rev. 12: 298-309; Johnson et al. 2007, Mod. Pathol. 20: 108-19), and taking into account the predictions of variability on PK indices already incorporated into the model, no specific changes for the clearance and/or absorption from the alveolar space were required to account for RSV infection.

Figure 5:
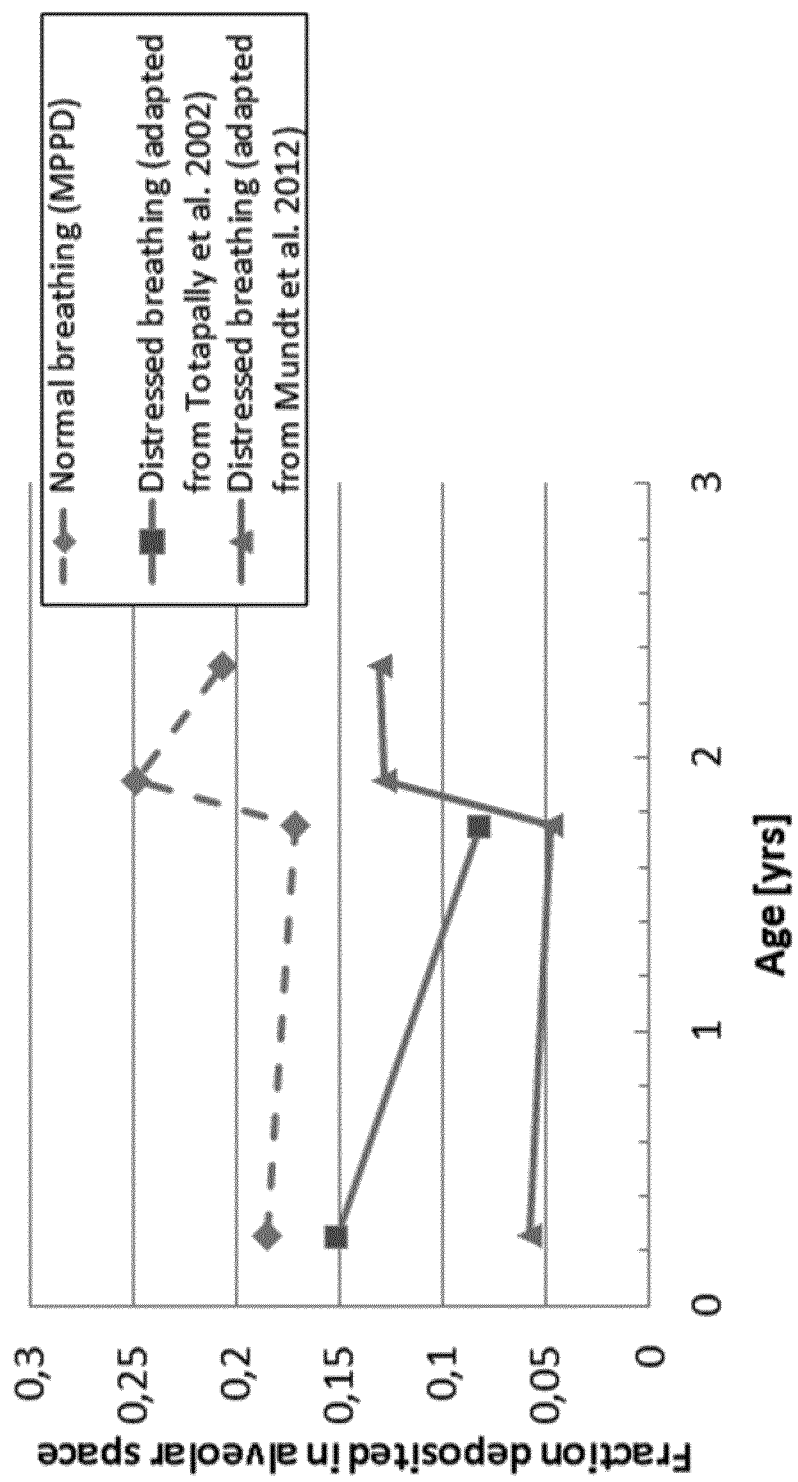
FIG. 5 is a graph depicting the age dependent fraction of inhaled dose deposited in the alveolar space as calculated with the MPPD tool for different distressed breathing scenarios compared to results from normal breathing.

With respect to the fraction deposited in the alveolar space, MPPD calculations considering altered breathing pattern reflecting the RSV infection were used to estimate the fraction of inhaled dose deposited in the alveolar space in RSV infected children. In the first scenario, the breathing frequency and the tidal volume of children younger than one year observed by Totapally et al. 2002 (Crit. Care 6: 160-5) were used. In the second scenario, the same relative changes in breathing frequency and tidal volume that were employed by Mundt et al. 2012 (ISRN Pediatr. 2012 p. 721295) to mimic the effects of bronchiolitis were used to adopt the respective MPPD default values. The fractions deposited in the alveolar space predicted by the MPPD tool with the distressed breathing patterns were lower compared to the results for normal breathing, especially for the scenario using the breathing pattern adopted from Mundt et al 2012 (FIG. 5).

The simulations showed that breathing patterns representative for RSV-infected infants and toddlers (age range of 5 to 24 months) resulted in deposition of ~10% of the inhaled amount of SEQ ID NO: 71 in the lower respiratory tract (7-13%, depending on age and particle size). Correspondingly, a dose of 0.24 mg/kg would need to be inhaled (inhaled dose) to reach a deposited dose of 0.024 mg/kg in the lower respiratory tract after one administration.

Example 9: Dose Determination for Treatment of RSV Lower Respiratory Tract Infections in Young Children Vibrating mesh type nebulisers are considered the most appropriate technology for nebulisation of a immunoglobulin single variable domains such as SEQ ID NO: 71 (WO 2011/098552). In the study further described (see Example 11), SEQ ID NO: 71 is administered using the FOX nebuliser (Activaero, now Vectura, Germany) adapted for paediatric use. The nebuliser is always used with a flow of 2 L/min additional air or $O_2$, and is equipped with a paediatric facemask (in 2 sizes).

The Sophia anatomical infant nose-throat (SAINT) model was used to generate data specifically for administration of SEQ ID NO: 71 with the above nebulizer (Janssens et al. 2001). The SAINT model is an anatomically correct cast/representation of the upper airways of a 9 month old child, built using stereolithographic techniques and used for studying aerosol deposition in young children. The administration conditions that will be used in the clinical setting were closely mimicked, including breathing patterns representative for healthy and RSV-infected infants and toddlers. The results showed that, from the total dose filled into the nebuliser, approximately 20% is expected to be inhaled. The dose filled in the nebuliser to ensure an inhaled dose of 0.24 mg/kg is therefore 1.2 mg/kg (nominal dose).

In line with other inhalation products, the administered dose of SEQ ID NO: 71 is standardised for (narrow) body weight categories (6 dose groups, with incremental steps of 1 or 2 kg, see Table B-2 and Table B-6). This is supported by safety margins and also takes into account feasibility of accurately measuring and filling the appropriate volume into the nebuliser with a (0.01 mL) graduated 1 mL syringe. The appropriateness of the body weight categories was also confirmed via additional PBPK simulations.

Taking into account the device specifications, the administration time corresponding to the weight-based categories varies from 45 seconds (5.0-6.0 kg subject) to 120 seconds (14.1-16.0 kg subject). A residual volume of ~7 µL (independent of the fill volume) remains in the reservoir of the nebuliser and has been taken into account in the fill volumes listed in Table B-2.

Taking into account the device specifications, the administration time corresponding to the weight-based categories varies from 30 seconds (3.5-3.9 kg subject) to 150 seconds (16.1-19.0 kg subject). A residual volume of ~7 µL (independent of the fill volume) remains in the reservoir of the nebuliser and has been taken into account in the fill volumes listed in Table B-6.

Example 10: Population Simulations

Population simulations were done for the six dose groups as described in Example 9, estimating the plasma and ALF concentrations in young children (age range from 5 to 24 months).

Figure 23:
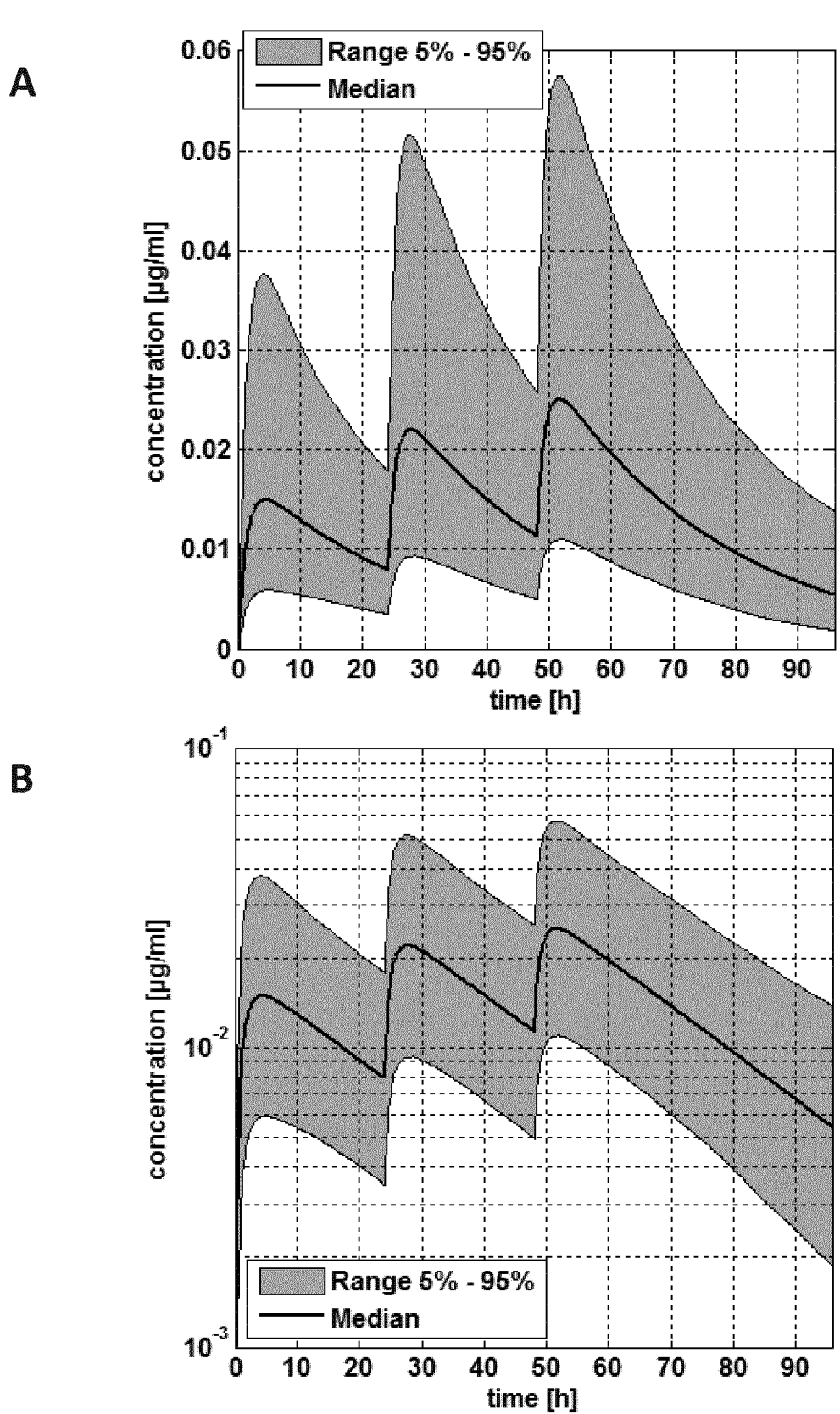
FIGS. 23A-23B are a pair of graphs providing a plasma concentration-time curve for the pooled population (5-24 months old children). Administration scheme: 0-24-48 h. A: linear concentration scale; B: log concentration scale.
Figure 24:
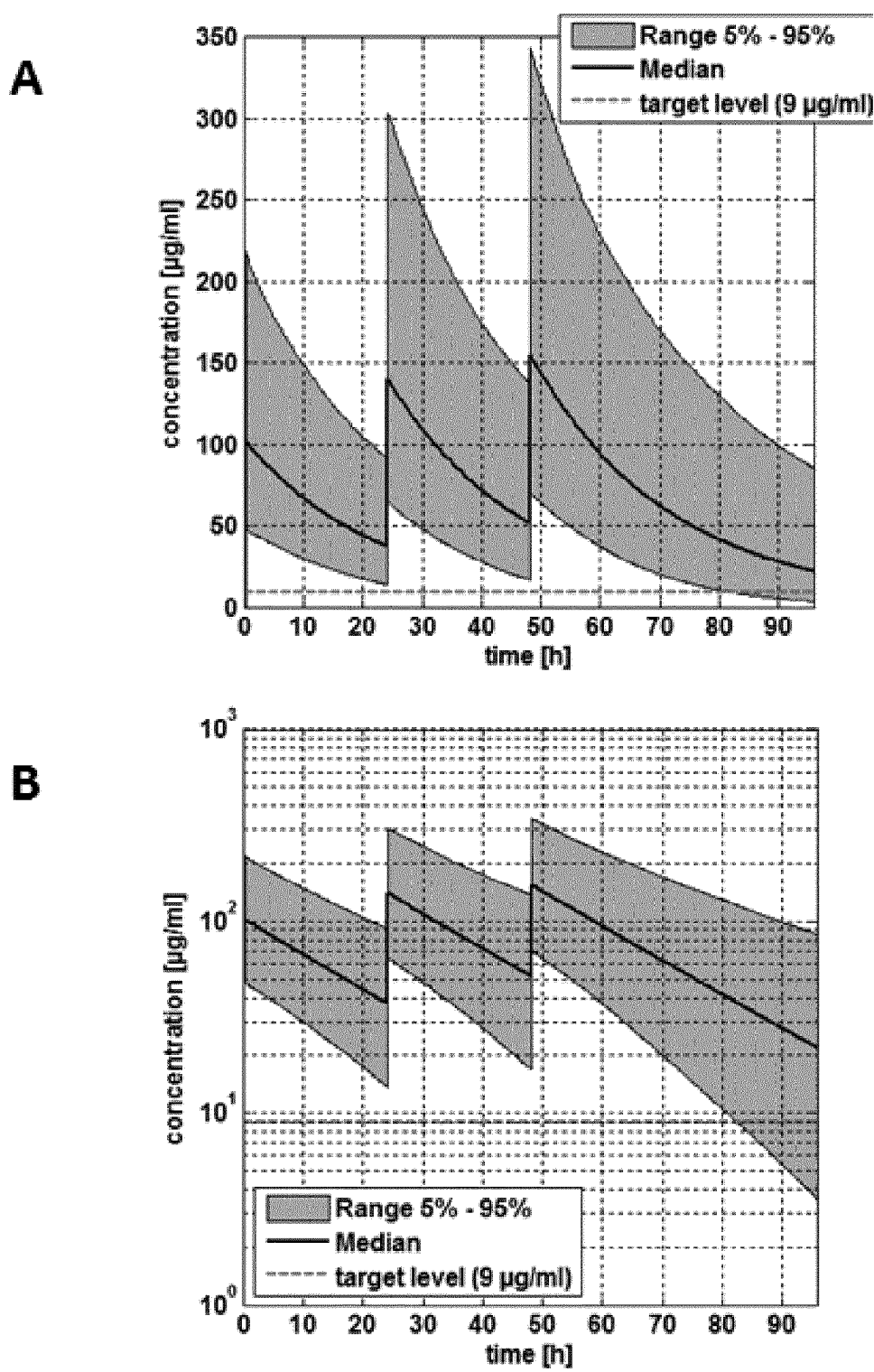
FIGS. 24A-24B are a pair of graphs providing an ALF concentration-time curve for the pooled population (5-24 months old children). Administration scheme: 0-24-48 h. A: linear concentration scale; B: log concentration scale.
Figure 25:
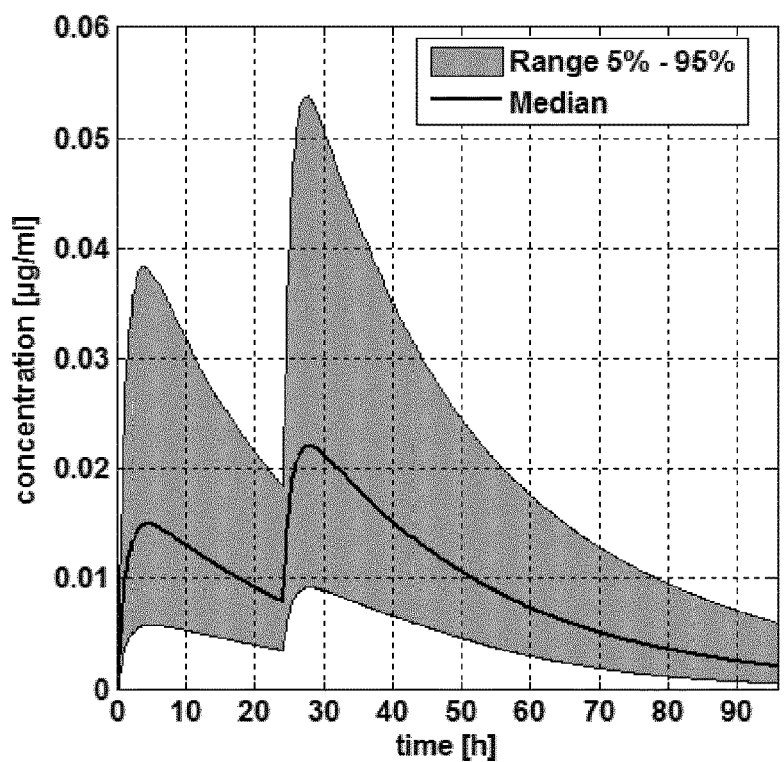
FIGS. 25A-25B are a pair of graphs providing a plasma concentration-time curve for the pooled population (5-24 months old children). Administration scheme: 0-24 h. A: linear concentration scale; B: log concentration scale.
Figure 25:
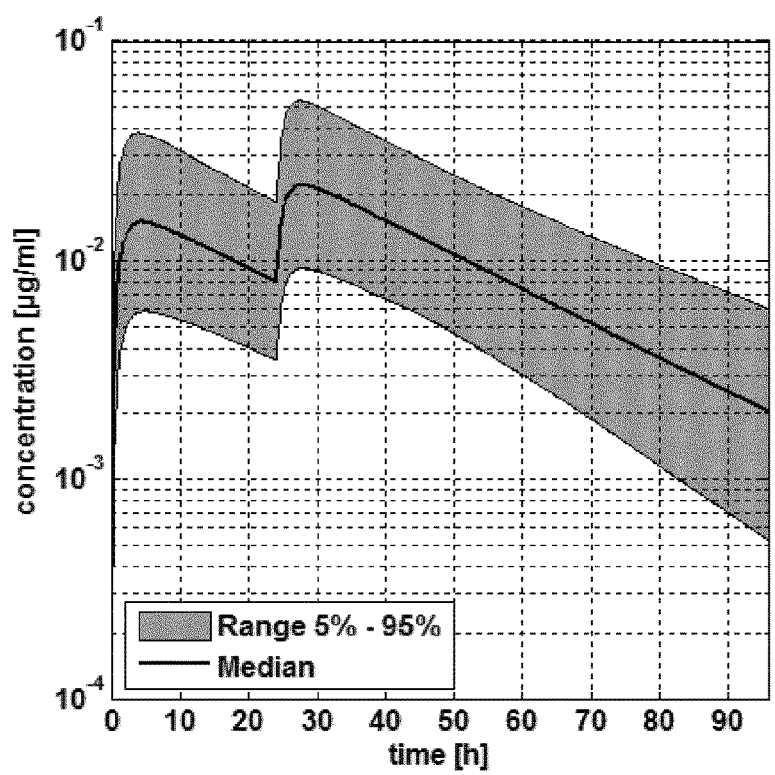
Figure 26:
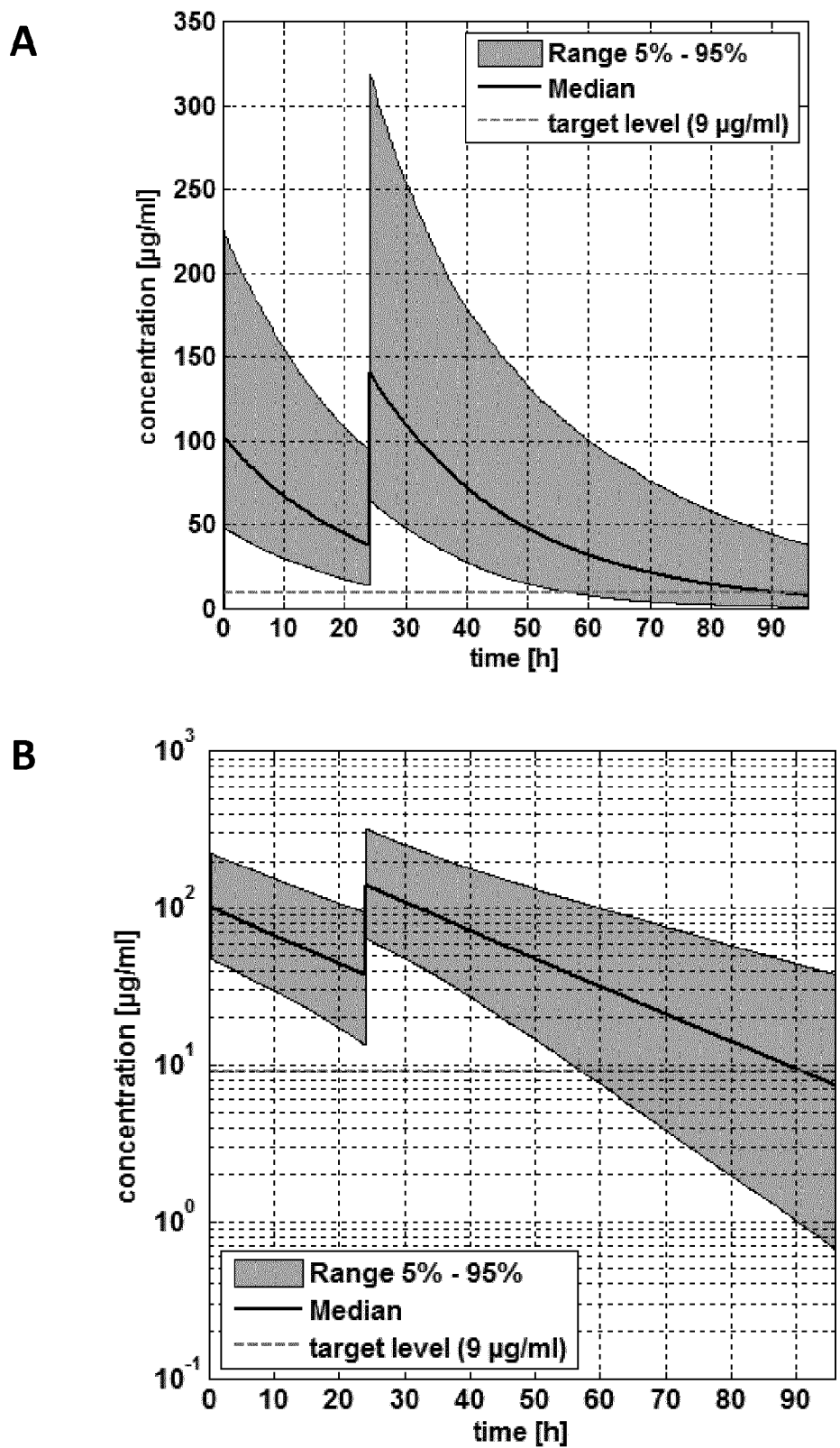
FIGS. 26A-26B are a pair of graphs providing an ALF concentration-time curve for the pooled population (5-24 months old children). Administration scheme: 0-24 h. A: linear concentration scale; B: log concentration scale.

The simulations were performed for different administration schemes:
Three administrations once daily (0, 24, 48 h);
Two administrations once daily (0 and 24 h);
Single administration (0 h);
The plasma and ALF concentration time profiles for the 0, 24, 48 h administration scheme are given in FIG. 23 and FIG. 24, respectively. During 72 h (3×24 h) after the first inhalation the alveolar concentration was larger than 14 µg/ml for 95% of the individuals. This is larger than in the previous simulations (9 µg/ml) due to the reduced geometric standard deviation of the fraction deposited and the dosing in the six dose groups (due to the body weight range within the groups the dose in alveolar space can be slightly larger than 0.024 mg/kg). Only 34 h after the last administration the $5^{th}$ concentration percentile drops below the target concentration of 9 µg/ml. The plasma and ALF concentration time profiles for the 0-24 h administration scheme are given in the FIG. 25 and FIG. 26, respectively. For the administration scheme 0-24 h, the $5^{th}$ percentile of the alveolar concentration for the total population drops below 9 µg/ml after 57 h. It is below the target concentration of 9 µg/ml for 20% of the time during 72 h after the first administration. The median alveolar concentration of the total population drops below 9 µg/ml after 91 h.

Figure 27:
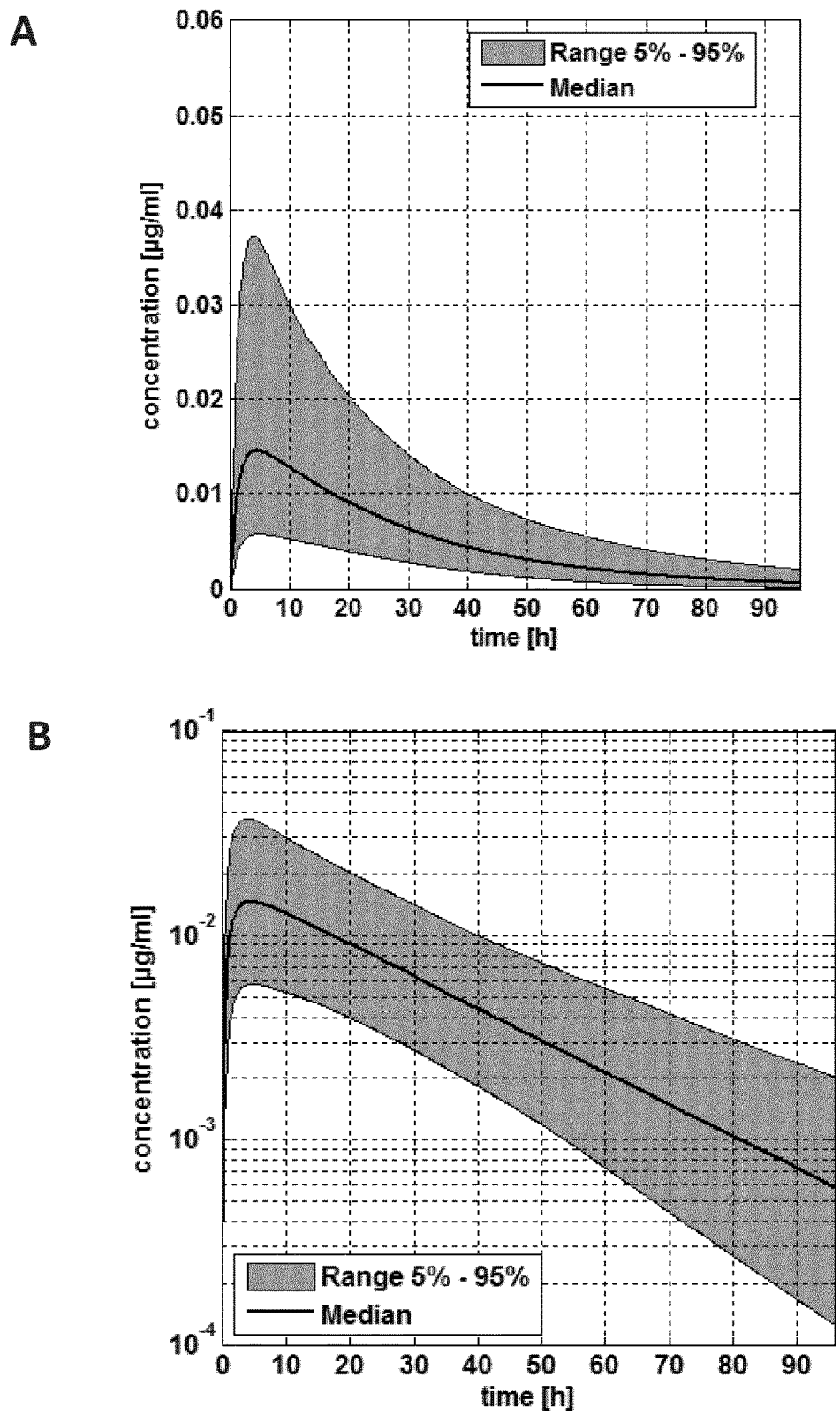
FIGS. 27A-27B are a pair of graphs providing a plasma concentration-time curve for the pooled population (5-24 months old children). Administration scheme: single dose. A: linear concentration scale; A: log concentration scale.
Figure 28:
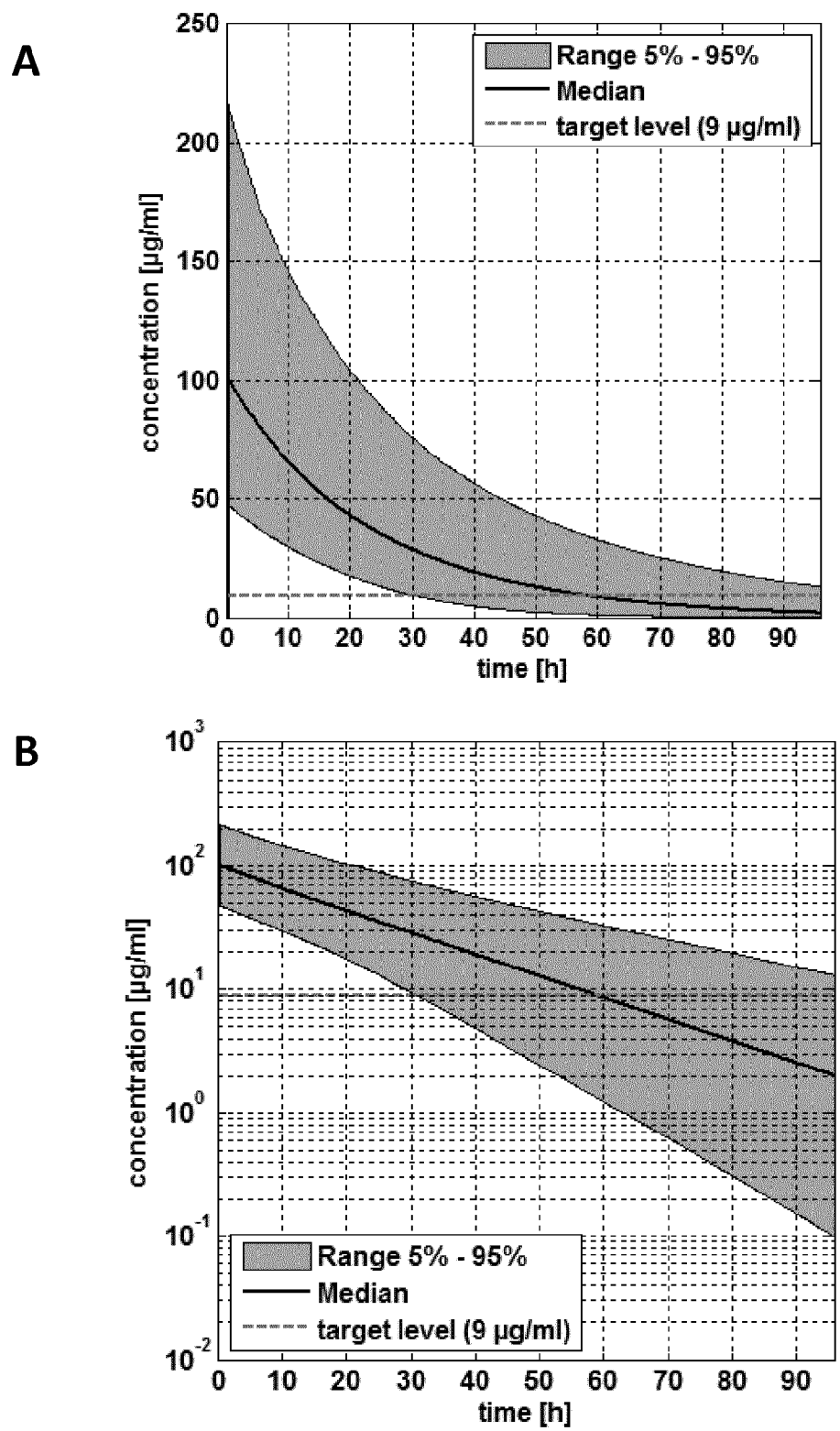
FIGS. 28A-28B are a pair of graphs providing an ALF concentration-time curve for the pooled population (5-24 months old children). Administration scheme: single dose. A: linear concentration scale; B: log concentration scale.
Figure 29:
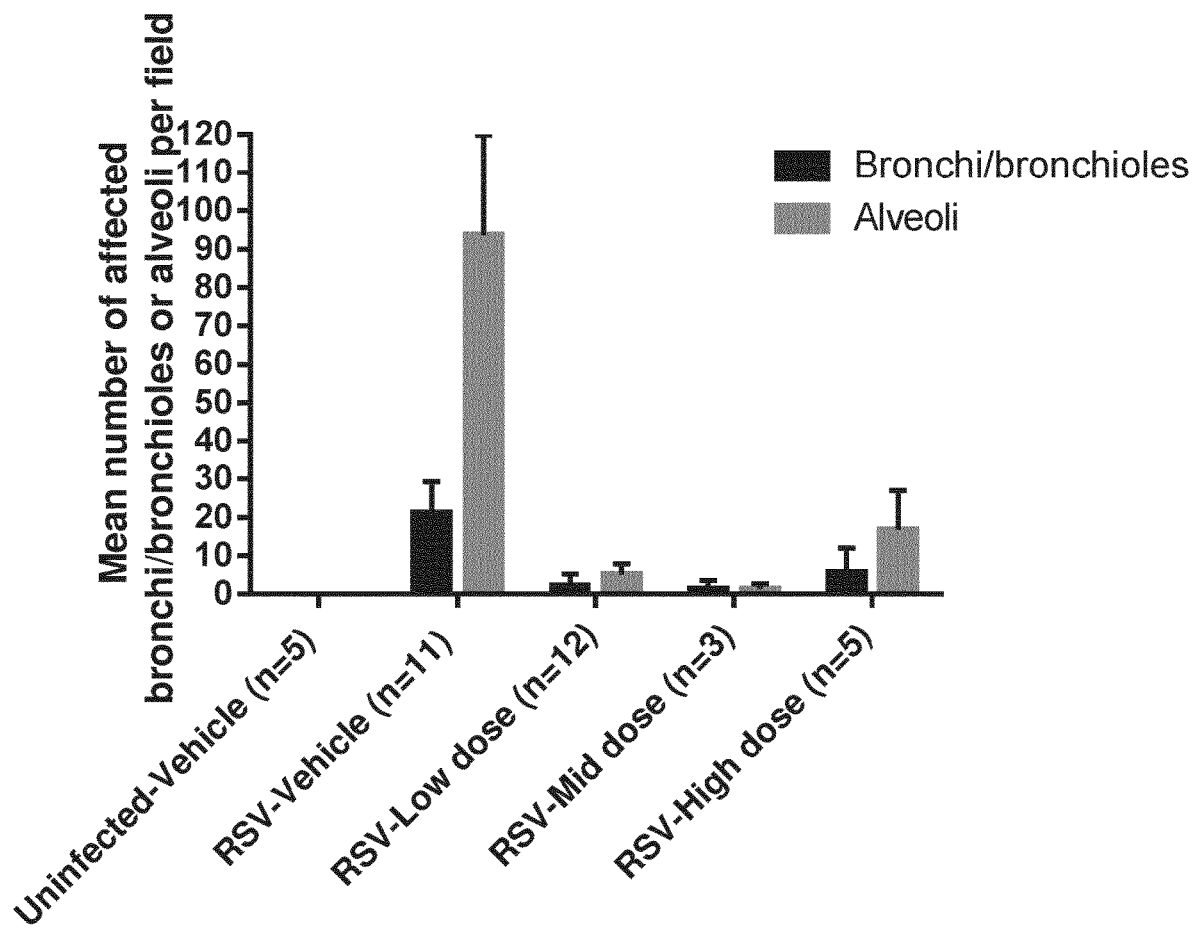
FIG. 29 is a graph depicting viral antigen detection in the lungs of hRSV-infected neonatal lambs. On day 6 post-infection 2 lung pieces per lobe of the right cranial, left cranial, left middle and left caudal lobes were sampled. Viral antigen was detected by immunohistochemistry and the number of affected bronchi/bronchioles or alveoli per field were counted. The results are expressed as mean of all the assessed lobes for all animals in three studies combined±SEM.
Figure 30:
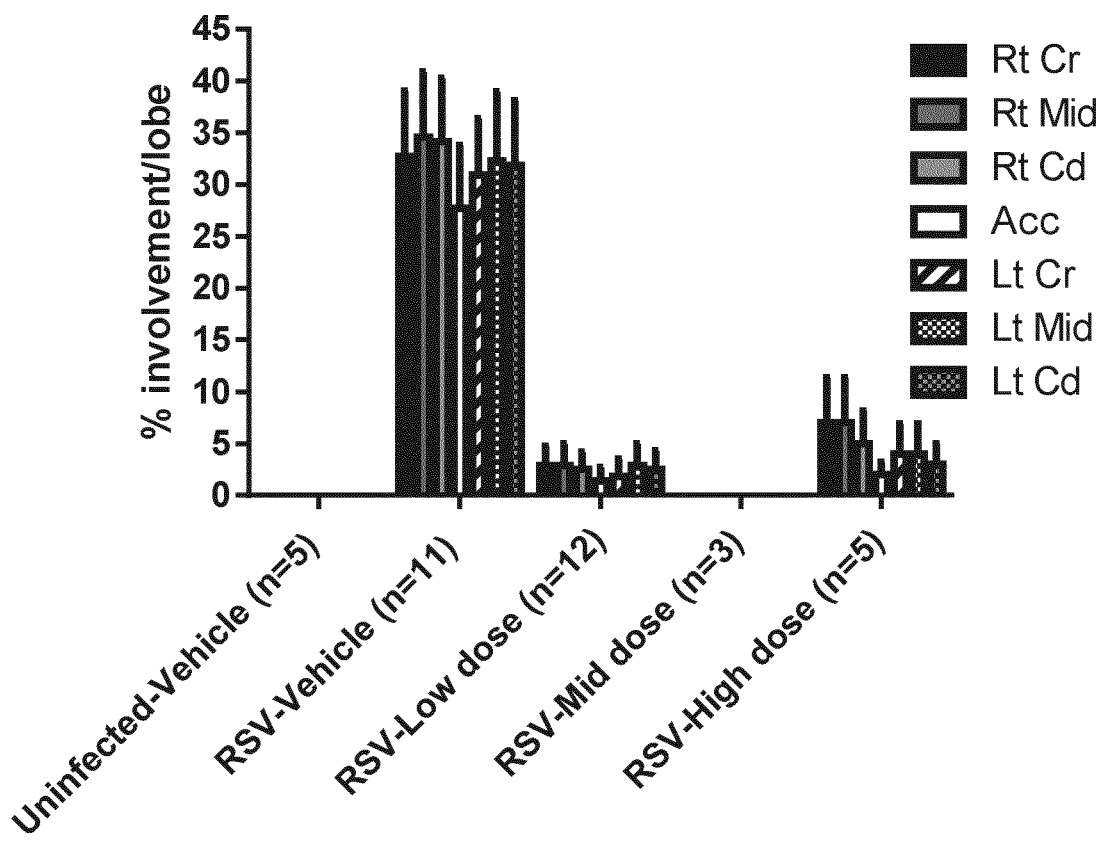
FIGS. 30A-30B are a pair of graphs depicting the results of the analysis described in Example 12. A. Gross lung examination of viral lesions Rt Cr: right cranial lobe; Rt Mid: right middle lobe; Rt Cd: right caudal lobe; Acc: accessory lobe; Lt Cr: left cranial lobe; Lt Mid: left middle lobe; Lt Cd: left caudal lobe. Results are depicted as mean per dose level and per lobe for all animals from 3 studies combined±SEM. B. Histological lung consolidation score in hRSV-infected neonatal lambs. The lungs of the phase 2 lambs were scored for lesions. Consolidation score is an overall score of the typical hRSV lesion. It means that several features were grouped into one overall score. Results are depicted as mean for all animals from 3 studies combined±SEM.
Figure 30:
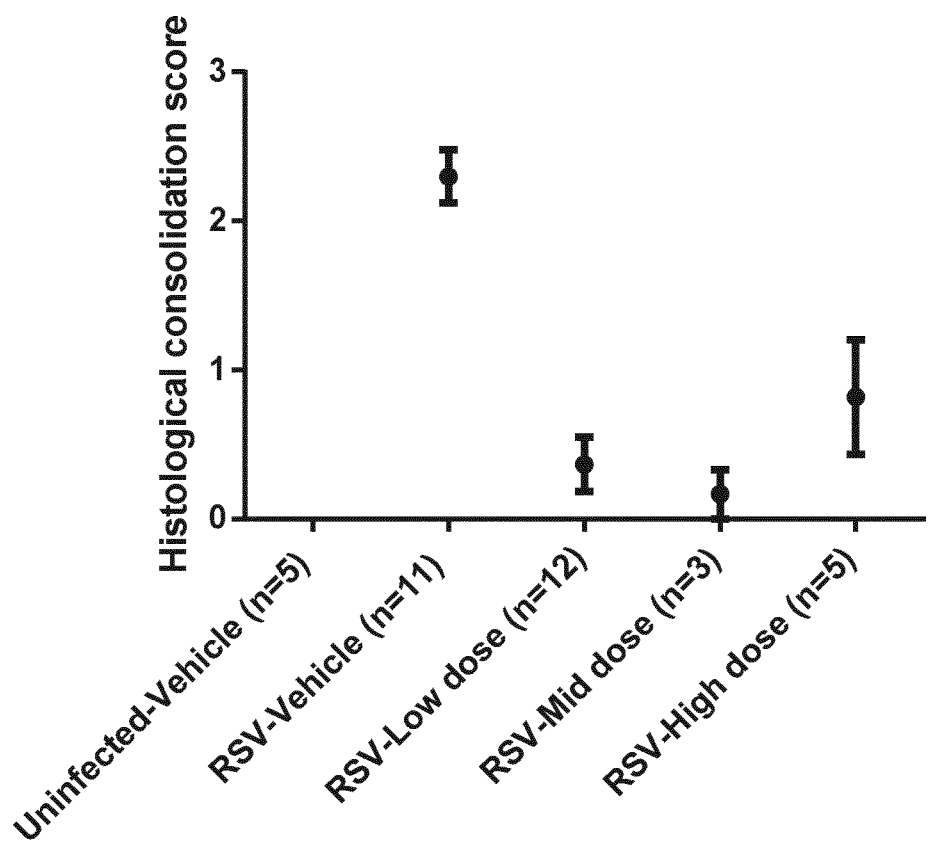
Figure 31:
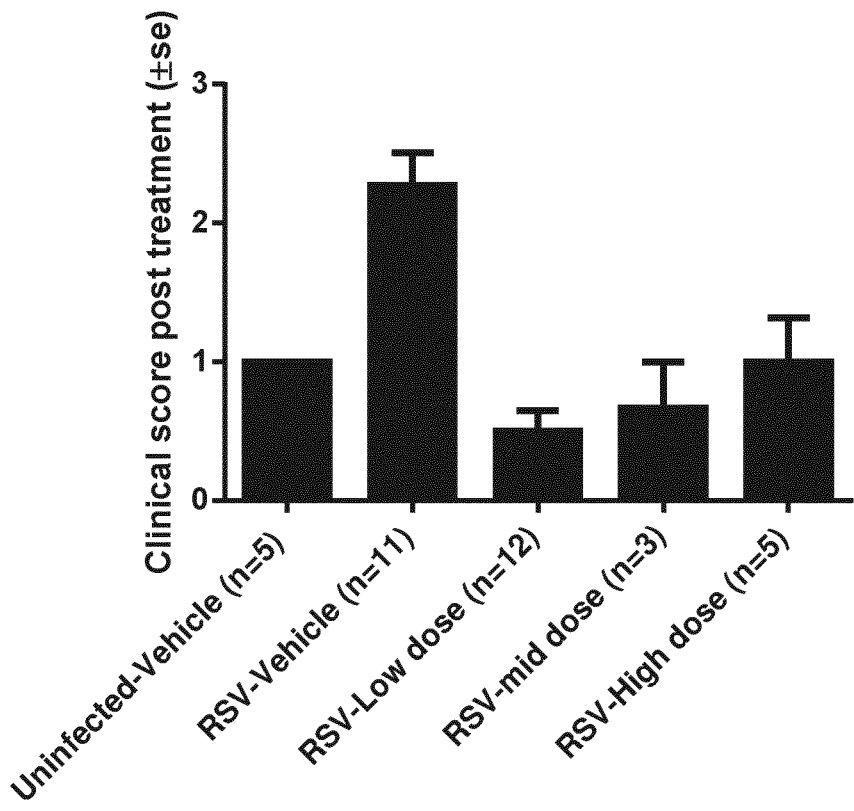
FIG. 31 is a graph depicting a clinical composite score. Clinical composite scores were determined based the criteria indicated in Table B-4. Results are depicted as mean per dose level for all animals from 3 studies combined±SEM.
Figure 32:
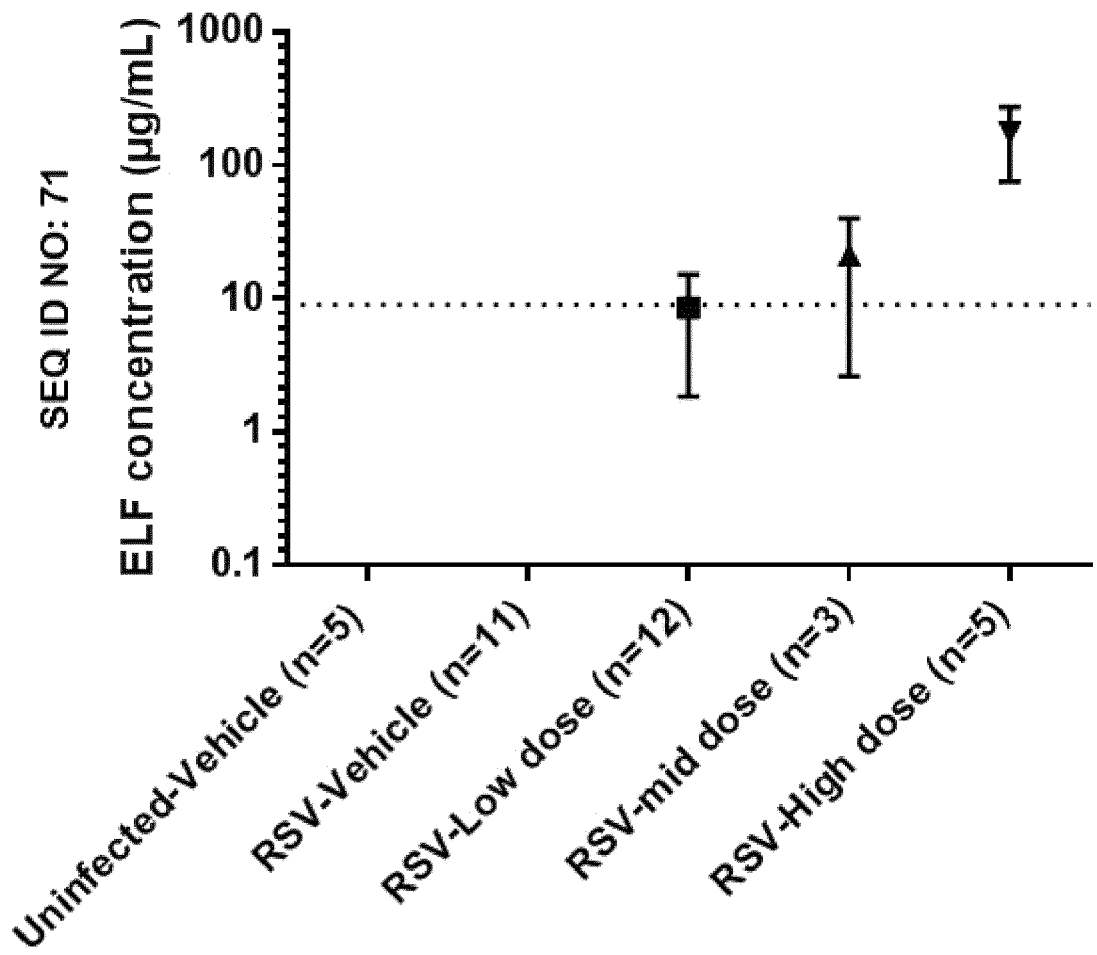
FIG. 32 is a graph depicting SEQ ID NO: 71 concentrations in epithelial lung lining fluid after three or five consecutive daily administrations by inhalation in hRSV-infected neonatal lambs. SEQ ID NO: 71 concentrations in ELF were derived from concentrations measured in BALF, which was sampled post-mortem, after normalization for dilution based on the Urea correction method (values were RBC corrected). BALE was sampled 24 hours after the last dose. Results are shown for all three studies combined as mean±SD. The hatched line represents the target concentration.

The plasma and ALF concentration time profiles for the single dose administration scheme are given in the FIG. 27 and FIG. 28, respectively. For single dosing, the $5^{th}$ percentile of the alveolar concentration for the total population drops below 9 µg/ml after 31 h. It is below the target concentration of 9 µg/ml for 57% of the time during 72 h after the first administration. The median alveolar concentration of the total population drops below 9 µg/ml after 59 h. It is below the target concentration of 9 µg/ml for 18% of the time during 72 h after the first administration.

Example 11: Treatment of RSV Infection in Infants and Toddlers

As described above, in children, an amount of SEQ ID NO: 71 in the alveolar absorption space (0.024 mg/kg body weight) was predicted to reach a pre-defined SEQ ID NO: 71 concentration in the alveolar target space (9 µg/ml). These predictions were made using a PBPK modelling approach with validated models incorporating observed data from several studies and from several species.

A study is conducted to assess the safety and tolerability of this dose regimen of SEQ ID NO: 71 administered pulmonary to infants and toddlers hospitalized for and diagnosed with RSV lower respiratory tract infection. Additionally, the effects of this dose regimen of SEQ ID NO: 71 on clinical effect, pharmacokinetics (PK), pharmacodynamics (PD), and immunogenicity of SEQ ID NO: 71 is assessed.

11.1 Study Design

A multicentre study in otherwise healthy infants and toddlers (aged 5 months to less than 24 months or age 3 months to less than 24 months) hospitalised for and diagnosed with Respiratory Syncytial Virus lower respiratory tract infection is conducted to evaluate the safety, tolerability and clinical activity of SEQ ID NO: 71, administered via inhalation, in addition to standard of care.

The study consists of 2 parts: an open-label lead-in part, followed by a double-blind placebo-controlled part. In line with the applicable Committee for Medicinal Products for Human Use (CHMP) guideline, an independent data monitoring committee (DMC) is assigned.

Open-label lead-in part of the study (Group I, N=5):

The initial 5 subjects are included in an open-label lead-in part, and receive only active study drug (SEQ ID NO: 71). The available data from this part of the study are reviewed by the DMC before initiating the double-blind placebo-controlled part of the study.

Double-blind placebo-controlled part of the study (Group II, N=30):

After a positive recommendation from the DMC, 30 subjects are enrolled in the subsequent double-blind placebo-controlled part of the study. Subjects are randomly assigned to receive either SEQ ID NO: 71 or placebo in a 2:1 ratio (N=20 to SEQ ID NO: 71, N=10 to placebo).

Approximately 15 minutes prior to administration of study drug, an inhaled dose of the short-acting $\beta_2$-agonist salbutamol is administered. Two puffs (2×100 μg) are given via metered-dose inhaler (with spacer).

SEQ ID NO: 71 is administered via inhalation, once daily for 3 consecutive days, in addition to standard of care. SEQ ID NO: 71 or matching placebo are administered using a dedicated vibrating mesh nebuliser (FOX device adapted for paediatric use). An overview of the appropriate volume to be filled in the nebulizer (per body weight category) and the appropriate nebulisation time is shown in Table B-2. SEQ ID NO: 71 is present at a concentration of 50 mg/mL SEQ ID NO: 71 in formulation buffer ($NaH_2PO_4$/$Na_2HPO_4$ 10 mM, NaCl 130 mM, pH 7.0).

The nebuliser is used with a fixed 2-L/min flow of air, or if needed, $O_2$ (to be decided by the Investigator based on $O_2$ need of the subject).

The planned study duration for each subject is approximately 15 days (including screening), focusing on the acute infection phase (and taking into account study drug exposure and half-life of SEQ ID NO: 71). The maximum study drug treatment duration for each subject is 3 days.

Subjects are screened for eligibility within 24 hours before administration of the study drug. Subjects receive once-daily doses of study drug on 3 consecutive days. Additional post-dose visits are foreseen for subjects who are not yet discharged from the hospital after the study drug treatment period. A discharge visit is scheduled before leaving the hospital (if applicable). One ambulatory follow-up visit is scheduled (Day 14).

11.2 Main Safety Evaluations

Safety is assessed among others by treatment emergent adverse events (TEAEs), clinical laboratory test results (clinical chemistry and haematology), physical examination results (including lung auscultation) and heart rate and peripheral capillary $O_2$ saturation ($SpO_2$).

11.3 Main Clinical Activity Evaluations

Clinical activity is assessed among other by feeding, respiratory rate (over a 1-minute interval), wheezing (during expiration/inspiration), crackles/crepitations (during lung auscultation), daytime coughing, (sleep disturbance from) night-time coughing, respiratory muscle retractions (supraclavicular, intercostal, and subcostal), and general appearance (activity, irritation, interest in environment, and responsiveness). Based on the clinical activity parameters measured during the study additional scores such as Clinical response, Respiratory Distress Assessment Instrument (RDAI) score and Respiratory Assessment Change Score (RACS) are calculated.

11.3 Exploratory Pharmacokinetics

The systemic concentration of SEQ ID NO: 71 is evaluated in serum, as a surrogate for evaluating local (lung) concentrations.

11.4 Exploratory Pharmacodynamics

Viral load are assessed in samples obtained via nasal swabs, as an exploratory PD parameter. Other exploratory biomarkers (serum) include Interleukin-8 (IL-8) and Krebs von den Lungen (KL-6).

11.5 Exploratory Immunogenicity

Potential immunogenicity (ADA) are also assessed systemically (serum).

Example 12: In Vivo Efficacy of SEQ ID NO: 71 Nanobody in a Neonatal Lamb RSV-Infection Model A neonatal lamb RSV-infection model was used to assess the in vivo efficacy of SEQ ID NO: 71, following delivery by inhalation. In total, three independent efficacy studies were performed. In brief, 2-5 day old colostrum-deprived lambs were infected on day 0 with RSV by nebulization using PARI LC SPRINT™ nebulizers (PARI Respiratory Equipment, Inc., Lancaster, Pa., USA). Three 2-mL aliquots of virus-containing media or control media were administered to each animal over the course of 23 minutes at 4 L/min at 16 PSI (Philips Respironics Air Compressor, Andover, Mass., USA) resulting in the total inhalation of about 6 mL by each lamb. Identical viral inoculum doses were used for each lamb (hRSV Memphis 37 strain at $1.27 \times 10^7$ FFU/mL in media with 20% w/v sucrose). SEQ ID NO: 71 treatment started either on day 1 (in 1 study) or day 3 (in 2 studies) post-infection and was repeated daily until day 5 post-infection. Administration was performed by nebulization, using the vibrating mesh based AERONEB® Solo System (Aerogen Ltd, Galway, Ireland). In total, 3 dose levels were tested and corresponded to 11 mg (low dose), 36 mg (mid-dose) and 110 mg (high dose) delivered SEQ ID NO: 71 dose.

Lambs were monitored daily for general well-being and respiratory rates, heart rates, body temperature, blood oxygen saturation, body weight, wheeze and expiratory efforts were recorded. Respiratory tissues and bronchoalveolar lavage (BAL) fluid were collected at day 6 post-inoculation for the quantification of viral lesions, lung viral titres, viral antigen and lung histopathology. All assessments were performed as described in Tables B-3 and B-4.

In the RSV-infected vehicle-treated lambs both viral RNA and cultivatable virus were consistently present in all lung lobes on day 6 for all studies performed (Table B-5). In addition, gross lung examination revealed extensive viral lesions involving ~12-40% of all lung lobes which were paralleled with viral antigen expression in the bronchioli/alveoli and histologic consolidation (FIGS. 29 and 30). On day 3 to 4 post-infection, first clinical signs of infection were detected, which included increased respiratory rates and expiratory efforts, wheeze and malaise although these symptoms were variable from one study to the next.

In the groups treated with SEQ ID NO: 71, three different doses were administered to the lambs. Each dose level, regardless of day of treatment start, strongly reduced viral titers (Table B-5), viral antigen expression (FIG. 29), gross viral lesions and histopathological scores (FIG. 30). Moreover, although clinical signs manifested in different ways a positive effect on composite clinical score was observed for all tested doses (FIG. 31).

Mean SEQ ID NO: 71 concentrations in lung epithelial lining fluid from all animals combined were close to or above 9 μg/mL for all doses (FIG. 32). This 9 μg/mL was defined as the $IC_{90}$×100 from in vitro neutralization assays using the RSV-B prototypic strain (18537). Data with the Memphis 37 strain showed that it was ~6-fold more sensitive than the RSV-B 18537.

As a conclusion, SEQ ID NO: 71 treatment exerted beneficial effects on RSV infection-induced changes when delivered daily for 3 or 5 days in neonatal lambs. Dose dependency was not apparent, which was to be expected, given that achieved concentrations in the target tissue (ELF) were at all doses at or above the target concentration that was expected to convey full efficacy.

TABLE A-1

Amino acid sequences of anti-hRSV immunoglobulin single variable domains (with FR and CDR sequences indicated)

| Nanobody® | SEQ ID | FR1 | SEQ ID | CDR 1 | SEQ ID | FR2 | SEQ ID | CDR 2 | SEQ ID | FR3 | SEQ ID | CDR 3 | SEQ ID | FR4 | SEQ ID |
|---|---|---|---|---|---|---|---|---|---|---|---|---|---|---|---|
| NC41 | 1 | EVQLVESGGGLVQAGG SLSLSISCAASGGSLS | 35 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGRGTQVTVSS | 62 |
| NC41 E1D | 2 | DVQLVESGGGLVQAGG SLSLSISCAASGGSLS | 36 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGRGTQVTVSS | 62 |
| NC41v01 | 3 | EVQLLESGGGLVQPGG SLRLSCAASGGSLS | 37 | NYVLG | 46 | WFRQAPG KGREFVA | 48 | AINWRGDITI GPPNVEG | 49 | RFTISRDNAKNTLYLQ MNSLAPEDTAVYYCGA | 52 | GTPLNPGAYI YDWSYDY | 61 | WGQGTLVTVSS | 63 |
| NC41v02 | 4 | EVQLLESGGGLVQPGG SLRLSCAASGGSLS | 38 | NYVLG | 46 | WFRQAPG KGREFVA | 48 | AINWRGDITI GPPNVEG | 49 | RFTISRENSKNTLYLQ MNSLAPEDTAVYYCGA | 53 | GTPLNPGAYI YDWSYDY | 61 | WGQGTLVTVSS | 63 |
| NC41v03 | 5 | EVQLLESGGGLVQPGG SLRLSCAASGGSLS | 38 | NYVLG | 46 | WFRQAPG KGREFVA | 48 | AINWRGDITI GPPNVEG | 49 | RFTISRENSKNTLYLQ MNSLRPEDTAVYYCGA | 54 | GTPLNPGAYI YDWSYDY | 61 | WGQGTLVTVSS | 63 |
| NC41v03 E1D | 6 | DVQLLESGGGLVQPGG SLRLSCAASGGSLS | 39 | NYVLG | 46 | WFRQAPG KGREFVA | 48 | AINWRGDITI GPPNVEG | 49 | RFTISRENSKNTLYLQ MNSLRPEDTAVYYCGA | 54 | GTPLNPGAYI YDWSYDY | 61 | WGQGTLVTVSS | 63 |
| NC41v04 | 7 | EVQLLESGGGLVQPGG SLSLSCAASGGSLS | 40 | NYVLG | 46 | WFRQAPG KGREFVA | 48 | AINWRGDITI GPPNVEG | 49 | RFTISRENSKNTLYLQ MNSLRPEDTAVYYCGA | 55 | GTPLNPGAYI YDWSYDY | 61 | WGQGTLVTVSS | 63 |
| NC41v05 | 8 | EVQLLESGGGLVQPGG SLSLSCAASGGSLS | 40 | NYVLG | 46 | WFRQAPG KGREFVA | 48 | AINWRGDITI GPPNVEG | 49 | RFTISRENSKNTLYLQ MNSLRPEDTAVYYCGA | 53 | GTPLNPGAYI YDWSYDY | 61 | WGQGTLVTVSS | 63 |
| NC41v06 | 9 | EVQLLESGGGLVQPGG SLRLSCAASGGSLS | 37 | NYVLG | 46 | WFRQAPG KGREFVA | 48 | AINWRDDITI GPPNVEG | 50 | RFTISRDNAKNTLYLQ MNSLRPEDTAVYYCGA | 56 | GTPLNPGAYI YDWSYDY | 61 | WGQGTLVTVSS | 63 |
| NC41v06 E1D | 10 | DVQLLESGGGLVQPGG SLRLSCAASGGSLS | 41 | NYVLG | 46 | WFRQAPG KGREFVA | 48 | AINWRDDITI GPPNVEG | 50 | RFTISRDNAKNTLYLQ MNSLRPEDTAVYYCGA | 56 | GTPLNPGAYI YDWSYDY | 61 | WGQGTLVTVSS | 63 |
| NC41v07 | 11 | EVQLLESGGGLVQPGG SLSLSCAASGGSLS | 40 | NYVLG | 46 | WFRQAPG KGREFVA | 48 | AINWRGDITI GPPNVEG | 49 | RFTISRDNAKNTLYLQ MNSLRPEDTAVYYCGA | 57 | GTPLNPGAYI YDWSYDY | 61 | WGQGTLVTVSS | 63 |
| NC41v08 | 12 | EVQLLESGGGLVQPGG SLSLSCAASGGSLS | 40 | NYVLG | 46 | WFRQAPG KGREFVA | 48 | AINWRGDITI GPPNVEG | 49 | RFTISRDNAKNTLYLQ MNSLRPEDTAVYYCGA | 56 | GTPLNPGAYI YDWSYDY | 61 | WGQGTLVTVSS | 63 |
| NC41v09 | 13 | EVQLLESGGGLVQPGG SLSLSCAASGGSLS | 40 | NYVLG | 46 | WFRQAPG KGREFVA | 48 | AINWRGDITI GPPNVEG | 49 | RFTISRENSKNTLYLQ MNSLRPDDTAVYYCGA | 55 | GTPLNPGAYI YDWSYDY | 61 | WGQGTLVTVSS | 63 |
| NC41v10 | 14 | EVQLLESGGGLVQPGG SLSLSCAASGGSLS | 40 | NYVLG | 46 | WFRQAPG KGREFVA | 48 | AINWRGDITI GPPNVEG | 49 | RFTISRDNAKNTLYLQ MNSLAPDDTAVYYCGA | 51 | GTPLNPGAYI YDWSYDY | 61 | WGQGTLVTVSS | 63 |
| NC41v11 | 15 | EVQLLESGGGLVQAGG SLSLSISCAASGGSLS | 42 | NYVLG | 46 | WFRQAPG KGREFVA | 48 | AINWRGDITI GPPNVEG | 49 | RFTISRDNAKNTGYLQ MNSLAPDDTAVYYCGA | 51 | GTPLNPGAYI YDWSYDY | 61 | WGQGTLVTVSS | 63 |

TABLE A-1-continued

Amino acid sequences of anti-hRSV immunoglobulin single variable domains (with FR and CDR sequences indicated)

| Nanobody® | SEQ ID | FR1 | SEQ ID | CDR 1 | SEQ ID | FR2 | SEQ ID | CDR 2 | SEQ ID | FR3 | SEQ ID | CDR 3 | SEQ ID | FR4 | SEQ ID |
|---|---|---|---|---|---|---|---|---|---|---|---|---|---|---|---|
| NC41v12 | 16 | EVQLLESGGGLVQPGG SLSISCAASGGSLS | 40 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGQGTLVTVSS | 63 |
| NC41v13 | 17 | EVQLLESGGGLVQPGG SLRLSCAASGGSLS | 37 | NYVLG | 46 | WFRQAPG KGREFVA | 48 | AINWRGDITI GPPNVEG | 49 | RFTISRDNAKNTGYLQ MNSLAPEDTAVYYCGA | 58 | GTPLNPGAYI YDWSYDY | 61 | WGQGTLVTVSS | 63 |
| NC41v14 | 18 | EVQLLESGGGLVQPGG SLRLSCAASGGSLS | 37 | NYVLG | 46 | WFRQAPG KGREFVA | 48 | AINWRGDITI GPPNVEG | 49 | RFTISRENSKNTLYLQ MNSLAPEDTAVYYCGA | 53 | GTPLNPGAYI YDWSYDY | 61 | WGQGTLVTVSS | 63 |
| NC41v15 | 19 | EVQLLESGGGLVQAGG SLRLSCAASGGSLS | 43 | NYVLG | 46 | WFRQAPG KGREFVA | 48 | AINWRGDITI GPPNVEG | 49 | RFTISRDNAKNTLYLQ MNSLAPEDTAVYYCGA | 52 | GTPLNPGAYI YDWSYDY | 61 | WGQGTLVTVSS | 63 |
| NC41v17 | 20 | EVQLLESGGGLVQPGG SLRLSCAASGGSLS | 37 | NYVLG | 46 | WFRQAPG KGREFVA | 48 | AINWRGDITI GPPNVEG | 49 | RFTISRENSKNTLYLQ MNSLRPEDTAVYYCGA | 54 | GTPLNPGAYI YDWSYDY | 61 | WGQGTLVTVSS | 63 |
| NC41v17 E1D | 21 | DVQLLESGGGLVQPGG SLRLSCAASGGSLS | 41 | NYVLG | 46 | WFRQAPG KGREFVA | 48 | AINWRGDITI GPPNVEG | 49 | RFTISRENSKNTLYLQ MNSLRPEDTAVYYCGA | 54 | GTPLNPGAYI YDWSYDY | 61 | WGQGTLVTVSS | 63 |
| NC41v18 | 22 | EVQLLESGGGLVQPGG SLRLSCAASGGSLS | 37 | NYVLG | 46 | WFRQAPG KGREFVA | 48 | AINWRDDITI GPPNVEG | 50 | RFTISRENSKNTLYLQ MNSLRPEDTAVYYCGA | 54 | GTPLNPGAYI YDWSYDY | 61 | WGQGTLVTVSS | 63 |
| NC41v18 E1D | 23 | DVQLLESGGGLVQPGG SLRLSCAASGGSLS | 41 | NYVLG | 46 | WFRQAPG KGREFVA | 48 | AINWRDDITI GPPNVEG | 50 | RFTISRDNAKNTGYLQ MNSLRPEDTAVYYCGA | 54 | GTPLNPGAYI YDWSYDY | 61 | WGQGTLVTVSS | 63 |
| NC41v19 | 24 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGQGTLVTVSS | 63 |
| NC41v20 | 25 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLRPEDTAVYYCGA | 59 | GTPLNPGAYI YDWSYDY | 61 | WGQGTLVTVSS | 63 |
| NC41v21 | 26 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPEDTAVYYCGA | 58 | GTPLNPGAYI YDWSYDY | 61 | WGQGTLVTVSS | 63 |
| NC41v21 E1D | 27 | DVQLVESGGGLVQPGG SLRLSCAASGGSLS | 45 | NYVLG | 46 | WFRQAPG KEREFVA | 47 | AINWRGDITI GPPNVEG | 49 | RFTISRDNAKNTGYLQ MNSLAPEDTAVYYCGA | 58 | GTPLNPGAYI YDWSYDY | 61 | WGQGTLVTVSS | 63 |
| NC41v22 | 28 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPEDTAVYYCGA | 60 | GTPLNPGAYI YDWSYDY | 61 | WGQGTLVTVSS | 63 |
| NC41v22 E1D | 29 | DVQLVESGGGLVQPGG SLRLSCAASGGSLS | 45 | NYVLG | 46 | WFRQAPG KEREFVA | 47 | AINWRGDITI GPPNVEG | 49 | RFTISRDNAKNTGYLQ MNSLAPEDTAVYYCGA | 60 | GTPLNPGAYI YDWSYDY | 61 | WGQGTLVTVSS | 63 |
| NC41v23 | 30 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGRGTLVTVSS | 64 |
| NC41v24 | 31 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLRPDDTAVYYCGA | 59 | GTPLNPGAYI YDWSYDY | 61 | WGRGTLVTVSS | 64 |

TABLE A-1-continued

Amino acid sequences of anti-hRSV immunoglobulin single variable domains (with FR and CDR sequences indicated)

| Nanobody® | SEQ ID | FR1 | SEQ ID | CDR 1 | SEQ ID | FR2 | SEQ ID | CDR 2 | SEQ ID | FR3 | SEQ ID | CDR 3 | SEQ ID | FR4 | SEQ ID |
|---|---|---|---|---|---|---|---|---|---|---|---|---|---|---|---|
| NC41v25 | 32 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPEDTAVYYCGA | 58 | GTPLNPGAYI YDWSYDY | 61 | WGRGTLVTVSS | 64 |
| NC41v26 | 33 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLRPEDTAVYYCGA | 60 | GTPLNPGAYI YDWSYDY | 61 | WGRGTLVTVSS | 64 |
| NC41v26 E1D | 34 | DVQLVESGGGLVQPGG SLRLSCAASGGSLS | 45 | NYVLG | 46 | WFRQAPG KEREFVA | 47 | AINWRGDITI GPPNVEG | 49 | RFTISRDNAKNTGYLQ MNSLRPEDTAVYYCGA | 60 | GTPLNPGAYI YDWSYDY | 61 | WGRGTLVTVSS | 64 |

TABLE A-2

Amino acid sequences of anti-hRSV immunoglobulin single variable domains

| Nanobody® | SEQ ID NO: | Sequence |
|---|---|---|
| NC41 | 1 | EVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRGTQVTVSS |
| NC41 E1D | 2 | DVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRGTQVTVSS |
| NC41v01 | 3 | EVQLLESGGGLVQPGGSLRLSCAASGGSLSNYVLGWFRQAPGKGREFVAAINWRGDITIGPPNVEGRFTISRDNAKNTLYLQMNSLAPEDTAVYYCGAGTPLNPGAYIYDWSYDYWGQGTLVTVSS |
| NC41v02 | 4 | EVQLLESGGGLVQPGGSLRISCAASGGSLSNYVLGWFRQAPGKGREFVAAINWRGDITIGPPNVEGRFTISRDNSKNTLYLQMNSLAPEDTAVYYCGAGTPLNPGAYIYDWSYDYWGQGTLVTVSS |
| NC41v03 | 5 | EVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSS |
| NC41v03 E1D | 6 | DVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSS |
| NC41v04 | 7 | EVQLLESGGGLVQPGGSLSISCAASGGSLSNYVLGWFRQAPGKGREFVAAINWRGDITIGPPNVEGRFTISRDNSKNTLYLQMNSLRPDDTAVYYCGAGTPLNPGAYIYDWSYDYWGQGTLVTVSS |
| NC41v05 | 8 | EVQLLESGGGLVQPGGSLSISCAASGGSLSNYVLGWFRQAPGKGREFVAAINWRGDITIGPPNVEGRFTISRDNSKNTLYLQMNSLAPEDTAVYYCGAGTPLNPGAYIYDWSYDYWGQGTLVTVSS |
| NC41v06 | 9 | EVQLLESGGGLVQPGGSLRLSCAASGGSLSNYVLGWFRQAPGKGREFVAAINWRDDITIGPPNVEGRFTISRDNAKNTLYLQMNSLRPEDTAVYYCGAGTPLNPGAYIYDWSYDYWGQGTLVTVSS |
| NC41v06 E1D | 10 | DVQLLESGGGLVQPGGSLRLSCAASGGSLSNYVLGWFRQAPGKGREFVAAINWRDDITIGPPNVEGRFTISRDNAKNTLYLQMNSLRPEDTAVYYCGAGTPLNPGAYIYDWSYDYWGQGTLVTVSS |
| NC41v07 | 11 | EVQLLESGGGLVQPGGSLSISCAASGGSLSNYVLGWFRQAPGKGREFVAAINWRGDITIGPPNVEGRFTISRDNAKNTLYLQMNSLAPDDTAVYYCGAGTPLNPGAYIYDWSYDYWGQGTLVTVSS |
| NC41v08 | 12 | EVQLLESGGGLVQPGGSLSISCAASGGSLSNYVLGWFRQAPGKGREFVAAINWRGDITIGPPNVEGRFTISRDNAKNTLYLQMNSLRPEDTAVYYCGAGTPLNPGAYIYDWSYDYWGQGTLVTVSS |
| NC41v09 | 13 | EVQLLESGGGLVQPGGSLSISCAASGGSLSNYVLGWFRQAPGKGREFVAAINWRGDITIGPPNVEGRFTISRDNSKNTLYLQMNSLRPDDTAVYYCGAGTPLNPGAYIYDWSYDYWGQGTLVTVSS |
| NC41v10 | 14 | EVQLLESGGGLVQPGGSLSISCAASGGSLSNYVLGWFRQAPGKGREFVAAINWRGDITIGPPNVEGRFTISRDNAKNTGYLQMNSLAPDDTAVYYCGAGTPLNPGAYIYDWSYDYWGQGTLVTVSS |
| NC41v11 | 15 | EVQLLESGGGLVQAGGSLSISCAASGGSLSNYVLGWFRQAPGKGREFVAAINWRGDITIGPPNVEGRFTISRDNAKNTGYLQMNSLAPDDTAVYYCGAGTPLNPGAYIYDWSYDYWGQGTLVTVSS |
| NC41v12 | 16 | EVQLLESGGGLVQPGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGQGTLVTVSS |
| NC41v13 | 17 | EVQLLESGGGLVQPGGSLRLSCAASGGSLSNYVLGWFRQAPGKGREFVAAINWRGDITIGPPNVEGRFTISRDNAKNTGYLQMNSLAPEDTAVYYCGAGTPLNPGAYIYDWSYDYWGQGTLVTVSS |
| NC41v14 | 18 | EVQLLESGGGLVQPGGSLRLSCAASGGSLSNYVLGWFRQAPGKGREFVAAINWRGDITIGPPNVEGRFTISRDNSKNTLYLQMNSLAPEDTAVYYCGAGTPLNPGAYIYDWSYDYWGQGTLVTVSS |
| NC41v15 | 19 | EVQLLESGGGLVQAGGSLRLSCAASGGSLSNYVLGWFRQAPGKGREFVAAINWRGDITIGPPNVEGRFTISRDNAKNTLYLQMNSLAPEDTAVYYCGAGTPLNPGAYIYDWSYDYWGQGTLVTVSS |

TABLE A-2-continued

Amino acid sequences of anti-hRSV immunoglobulin single variable domains

| Nanobody® | SEQ ID NO: | Sequence |
|---|---|---|
| NC41v17 | 20 | EVQLLESGGGLVQPGGSLRLSCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSS |
| NC41v17 E1D | 21 | DVQLLESGGGLVQPGGSLRLSCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSS |
| NC41v18 | 22 | EVQLLESGGGLVQPGGSLRLSCAASGGSLSNYVLGWFRQAPGKGREFVAAINWRDDITIGPPNVEGRFTISRDNSKNTLYLQMNSLRPEDTAVYYCGAGTPLNPGAYIYDWSYDYWGQGTLVTVSS |
| NC41v18 E1D | 23 | DVQLLESGGGLVQPGGSLRLSCAASGGSLSNYVLGWFRQAPGKGREFVAAINWRDDITIGPPNVEGRFTISRDNSKNTLYLQMNSLRPEDTAVYYCGAGTPLNPGAYIYDWSYDYWGQGTLVTVSS |
| NC41v19 | 24 | EVQLVESGGGLVQPGGSLRLSCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGQGTLVTVSS |
| NC41v20 | 25 | EVQLVESGGGLVQPGGSLRLSCAASGGSLSNYVLGWFRQAPGKEREFVAAINWRGDITIGPPNVEGRFTISRDNAKNTGYLQMNSLRPDDTAVYYCGAGTPLNPGAYIYDWSYDYWGQGTLVTVSS |
| NC41v21 | 26 | EVQLVESGGGLVQPGGSLRLSCAASGGSLSNYVLGWFRQAPGKEREFVAAINWRGDITIGPPNVEGRFTISRDNAKNTGYLQMNSLAPEDTAVYYCGAGTPLNPGAYIYDWSYDYWGQGTLVTVSS |
| NC41v21 E1D | 27 | DVQLVESGGGLVQPGGSLRLSCAASGGSLSNYVLGWFRQAPGKEREFVAAINWRGDITIGPPNVEGRFTISRDNAKNTGYLQMNSLAPEDTAVYYCGAGTPLNPGAYIYDWSYDYWGQGTLVTVSS |
| NC41v22 | 28 | EVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGQGTLVTVSS |
| NC41v22 E1D | 29 | DVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGQGTLVTVSS |
| NC41v23 | 30 | EVQLVESGGGLVQPGGSLRLSCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRGTLVTVSS |
| NC41v24 | 31 | EVQLVESGGGLVQPGGSLRLSCAASGGSLSNYVLGWFRQAPGKEREFVAAINWRGDITIGPPNVEGRFTISRDNAKNTGYLQMNSLRPDDTAVYYCGAGTPLNPGAYIYDWSYDYWGRGTLVTVSS |
| NC41v25 | 32 | EVQLVESGGGLVQPGGSLRLSCAASGGSLSNYVLGWFRQAPGKEREFVAAINWRGDITIGPPNVEGRFTISRDNAKNTGYLQMNSLAPEDTAVYYCGAGTPLNPGAYIYDWSYDYWGRGTLVTVSS |
| NC41v26 | 33 | EVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGRGTLVTVSS |
| NC41v26 E1D | 34 | DVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGRGTLVTVSS |

TABLE A-3

Amino acid sequences of preferred polypeptides of the invention

| Nanobody® | SEQ ID NO: | Sequence |
|---|---|---|
| RSV407 | 65 | EVQLVESGGGLVQAGGSLSISCAASGGSLSNYVLGWFRQAPGK-EREFVAAI NWRGDITIGPPNVEGRFTISRDNAKNTGYLQMNSLAPDDTAVYYC-GAGTPL NPGAYIYDWSYDYWGRGTQVTVSSGGGGSGGGGSGGGGSEVQLVES-GGGLV |

TABLE A-3-continued

Amino acid sequences of preferred polypeptides of the invention

Nanobody® SEQ ID NO: Sequence

|  |  |  |
|---|---|---|
|  |  | QAGGSLSISCAASGGSLSNYVLGWFRQAPGKEREFVAAINWRGDITIG-<br>PPN<br>VEGRFTISRDNAKNTGYLQMNSLAPDDTAVYYCGAGTPLNPGAYIYD-<br>WSYD<br>YWGRGTQVTVSSGGGGSGGGGSGGGGSEVQLVESGGGLVQAGGSLSIS-<br>CAA<br>SGGSLSNYVLGWFRQAPGKEREFVAAINWRGDITIGPPNVEGR-<br>FTISRDNA<br>KNTGYLQMNSLAPDDTAVYYCGAGTPLNPGAYIYDWSYDYWGRGTQVT-<br>VSS |
| RSV408 | 66 | EVQLVESGGGLVQAGGSLSISCAASGGSLSNYVLGWFRQAPGK-<br>EREFVAAI<br>NWRGDITIGPPNVEGRFTISRDNAKNTGYLQMNSLAPDDTAVYYC-<br>GAGTPL<br>NPGAYIYDWSYDYWGRGTQVTVSSAAAEVQLVESGGGLVQAGGSLSIS-<br>CAA<br>SGGSLSNYVLGWFRQAPGKEREFVAAINWRGDITIGPPNVEGR-<br>FTISRDNA<br>KNTGYLQMNSLAPDDTAVYYCGAGTPLNPGAYIYDWSYDYWGRGTQVT-<br>VSS<br>AAAEVQLVESGGGLVQAGGSLSISCAASGGSLSNYVLGWFRQAPGK-<br>EREFV<br>AAINWRGDITIGPPNVEGRFTISRDNAKNTGYLQMNSLAPDDTAVYYC-<br>GAG<br>TPLNPGAYIYDWSYDYWGRGTQVTVSS |
| RSV409 | 67 | EVQLVESGGGLVQAGGSLSISCAASGGSLSNYVLGWFRQAPGK-<br>EREFVAAI<br>NWRGDITIGPPNVEGRFTISRDNAKNTGYLQMNSLAPDDTAVYYC-<br>GAGTPL<br>NPGAYIYDWSYDYWGRGTQVTVSSGGGGSGGGSEVQLVES-<br>GGGLVQAGGSL<br>SISCAASGGSLSNYVLGWFRQAPGKEREFVAAINWRGDITIGPPNVEG-<br>RFT<br>ISRDNAKNTGYLQMNSLAPDDTAVYYCGAGTPLNPGAYIYDWSYDY-<br>WGRGT<br>QVTVSSGGGGSGGGSEVQLVESGGGLVQAGGSLSISCAASGGSLSNYV-<br>LGW<br>FRQAPGKEREFVAAINWRGDITIGPPNVEGRFTISRDNAKNT-<br>GYLQMNSLA<br>PDDTAVYYCGAGTPLNPGAYIYDWSYDYWGRGTQVTVSS |
| RSV410 | 68 | EVQLVESGGGLVQAGGSLSISCAASGGSLSNYVLGWFRQAPGK-<br>EREFVAAI<br>NWRGDITIGPPNVEGRFTISRDNAKNTGYLQMNSLAPDDTAVYYC-<br>GAGTPL<br>NPGAYIYDWSYDYWGRGTQVTVSSGGGGSGGGGSGGGGSGGGG-<br>SEVQLVES<br>GGGLVQAGGSLSISCAASGGSLSNYVLGWFRQAPGKEREFVAAIN-<br>WRGDIT<br>IGPPNVEGRFTISRDNAKNTGYLQMNSLAPDDTAVYYCGAGTPLN-<br>PGAYIY<br>DWSYDYWGRGTQVTVSSGGGGSGGGGSGGGGSGGGGSEVQLVES-<br>GGGLVQA<br>GGSLSISCAASGGSLSNYVLGWFRQAPGKEREFVAAINWRGDITIGPP-<br>NVE<br>GRFTISRDNAKNTGYLQMNSLAPDDTAVYYCGAGTPLNPGAYIYDWSY-<br>DYW<br>GRGTQVTVSS |
| RSV411 | 69 | EVQLVESGGGLVQAGGSLSISCAASGGSLSNYVLGWFRQAPGK-<br>EREFVAAI<br>NWRGDITIGPPNVEGRFTISRDNAKNTGYLQMNSLAPDDTAVYYC-<br>GAGTPL<br>NPGAYIYDWSYDYWGRGTQVTVSSGGGGSGGGGSGGGGSEVQLVES-<br>GGGLV<br>QAGGSLSISCAASGGSLSNYVLGWFRQAPGKEREFVAAINWRGDITIG-<br>PPN<br>VEGRFTISRDNAKNTGYLQMNSLAPDDTAVYYCGAGTPLNPGAYIYD-<br>WSYD<br>YWGRGTQVTVSSGGGGSGGGGSGGGGSEVQLVESGGGLVQPGGSLRLS-<br>CAA<br>SGLTLDYYALGWFRQAPGKEREGVSCISSSDHSTTYTDSVKGR-<br>FTISWDNA<br>KNTLYLQMNSLKPGDTAVYYCAADPALGCYSGSYYPRYDYWGQGTQVT-<br>VSS |

TABLE A-3-continued

Amino acid sequences of preferred polypeptides of the invention

| Nanobody® | SEQ ID NO: | Sequence |
|---|---|---|
| RSV413 | 70 | EVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRTQVTVSSGGGGSGGGGSGGGGSEVQLVESGGGLVQPGGSLRLSCAASGLTLDYYALGWFRQAPGKEREGVSCISSSDHSTTYTDSVKGRFTISWDNAKNTLYLQMNSLKPGDTAVYYCAADPALGCYSGSYYPRYDYWGQGTQVTVSSGGGGSGGGGSGGGGSEVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRTQVTVSS |
| RSV434 | 71 | DVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRTQVTVSSGGGGSGGGGSGGGGSEVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRTQVTVSSGGGGSGGGGSGGGGSEVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRTQVTVSS |
| RSV414 V03 | 72 | EVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSSGGGGSGGGGSGGGGSEVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSSGGGGSGGGGSGGGGSEVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSS |
| RSV443 V3D | 73 | DVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSSGGGGSGGGGSGGGGSEVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSSGGGGSGGGGSGGGGSEVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSS |
| RSV426 V06 | 74 | EVQLLESGGGLVQPGGSLRLSCAASGGSLSNYVLGWFRQAPGKGREFVAAINWRDDITIGPPNVEGRFTISRDNAKNTLYLQMNSLRPEDTAVYYCGAGTPLNPGAYIYDWSYDYWGQGTLVTVSSGGGGSGGGGSGGGGSEVQLLESGGGLVQPGGSLRLSCAASGGSLSNYVLGWFRQAPGKGREFVAAINWRDDITIGPPNVEGRFTISRDNAKNTLYLQMNSLRPEDTAVYYCGAGTPLNPGAYIYDWSYDYWGQGTLVTVSSGGGGSGGGGSGGGGSEVQLLESGGGLVQPGGSLRLSCAA |

TABLE A-3-continued

Amino acid sequences of preferred polypeptides of the invention

| Nanobody® | SEQ ID NO: | Sequence |
|---|---|---|
| | | SGGSLSNYVLGWFRQAPGKGREFVAAINWRDDITIGPPNVEGR-FTISRDNA KNTLYLQMNSLRPEDTAVYYCGAGTPLNPGAYIYDWSYDYWGQGTLVT-VSS |
| RSV444 V6D | 75 | DVQLLESGGGLVQPGGSLRLSCAASGGSLSNYVLGWFRQAPGK-GREFVAAI NWRDDITIGPPNVEGRFTISRDNAKNTLYLQMNSLRPEDTAVYYC-GAGTPL NPGAYIYDWSYDYWGQGTLVTVSSGGGGSGGGGSGGGG-SEVQLLESGGGLV QPGGSLRLSCAASGGSLSNYVLGWFRQAPGKGREFVAAINWRDDITIG-PPN VEGRFTISRDNAKNTLYLQMNSLRPEDTAVYYCGAGTPLNPGAYIYD-WSYD YWGQGTLVTVSSGGGGSGGGGSGGGGSEVQLLESGGGLVQPGGSLRLS-CAA SGGSLSNYVLGWFRQAPGKGREFVAAINWRDDITIGPPNVEGR-FTISRDNA KNTLYLQMNSLRPEDTAVYYCGAGTPLNPGAYIYDWSYDYWGQGTLVT-VSS |
| RSV442 V17 | 76 | EVQLLESGGGLVQPGGSLRLSCAASGGSLSNYVLGWFRQAPGK-GREFVAAI NWRGDITIGPPNVEGRFTISRDNSKNTLYLQMNSLRPEDTAVYYC-GAGTPL NPGAYIYDWSYDYWGQGTLVTVSSGGGGSGGGGSGGGG-SEVQLLESGGGLV QPGGSLRLSCAASGGSLSNYVLGWFRQAPGKGREFVAAINWRGDITIG-PPN VEGRFTISRDNSKNTLYLQMNSLRPEDTAVYYCGAGTPLNPGAYIYD-WSYD YWGQGTLVTVSSGGGGSGGGGSGGGGSEVQLLESGGGLVQPGGSLRLS-CAA SGGSLSNYVLGWFRQAPGKGREFVAAINWRGDITIGPPNVEGR-FTISRDNS KNTLYLQMNSLRPEDTAVYYCGAGTPLNPGAYIYDWSYDYWGQGTLVT-VSS |
| RSV435 V17D | 77 | DVQLLESGGGLVQPGGSLRLSCAASGGSLSNYVLGWFRQAPGK-GREFVAAI NWRGDITIGPPNVEGRFTISRDNSKNTLYLQMNSLRPEDTAVYYC-GAGTPL NPGAYIYDWSYDYWGQGTLVTVSSGGGGSGGGGSGGGG-SEVQLLESGGGLV QPGGSLRLSCAASGGSLSNYVLGWFRQAPGKGREFVAAINWRGDITIG-PPN VEGRFTISRDNSKNTLYLQMNSLRPEDTAVYYCGAGTPLNPGAYIYD-WSYD YWGQGTLVTVSSGGGGSGGGGSGGGGSEVQLLESGGGLVQPGGSLRLS-CAA SGGSLSNYVLGWFRQAPGKGREFVAAINWRGDITIGPPNVEGR-FTISRDNS KNTLYLQMNSLRPEDTAVYYCGAGTPLNPGAYIYDWSYDYWGQGTLVT-VSS |
| RSV427 V18 | 78 | EVQLLESGGGLVQPGGSLRLSCAASGGSLSNYVLGWFRQAPGK-GREFVAAI NWRDDITIGPPNVEGRFTISRDNSKNTLYLQMNSLRPEDTAVYYC-GAGTPL NPGAYIYDWSYDYWGQGTLVTVSSGGGGSGGGGSGGGG-SEVQLLESGGGLV QPGGSLRLSCAASGGSLSNYVLGWFRQAPGKGREFVAAINWRDDITIG-PPN VEGRFTISRDNSKNTLYLQMNSLRPEDTAVYYCGAGTPLNPGAYIYD-WSYD YWGQGTLVTVSSGGGGSGGGGSGGGGSEVQLLESGGGLVQPGGSLRLS-CAA SGGSLSNYVLGWFRQAPGKGREFVAAINWRDDITIGPPNVEGR-FTISRDNS KNTLYLQMNSLRPEDTAVYYCGAGTPLNPGAYIYDWSYDYWGQGTLVT-VSS |
| RSV445 V18D | 79 | DVQLLESGGGLVQPGGSLRLSCAASGGSLSNYVLGWFRQAPGK-GREFVAAI NWRDDITIGPPNVEGRFTISRDNSKNTLYLQMNSLRPEDTAVYYC-GAGTPL NPGAYIYDWSYDYWGQGTLVTVSSGGGGSGGGGSGGGG-SEVQLLESGGGLV QPGGSLRLSCAASGGSLSNYVLGWFRQAPGKGREFVAAINWRDDITIG-PPN |

TABLE A-3-continued

Amino acid sequences of preferred polypeptides of the invention

| Nanobody® | SEQ ID NO: | Sequence |
|---|---|---|
| | | VEGRFTISRDNSKNTLYLQMNSLRPEDTAVYYCGAGTPLNPGAYIYDWSYDYWGQGTLVTVSSGGGGSGGGGSGGGGSEVQLLESGGGLVQPGGSLRLSCAASGGSLSNYVLGWFRQAPGKGREFVAAINWRDDITIGPPNVEGRFTISRDNSKNTLYLQMNSLRPEDTAVYYCGAGTPLNPGAYIYDWSYDYWGQGTLVTVSS |
| RSV436 V20 | 80 | EVQLVESGGGLVQPGGSLRLSCAASGGSLSNYVLGWFRQAPGKEREFVAAINWRGDITIGPPNVEGRFTISRDNAKNTGYLQMNSLRPDDTAVYYCGAGTPLNPGAYIYDWSYDYWGQGTLVTVSSGGGGSGGGGSGGGGSEVQLVESGGGLVQPGGSLRLSCAASGGSLSNYVLGWFRQAPGKEREFVAAINWRGDITIGPPNVEGRFTISRDNAKNTGYLQMNSLRPDDTAVYYCGAGTPLNPGAYIYDWSYDYWGQGTLVTVSSGGGGSGGGGSGGGGSEVQLVESGGGLVQPGGSLRLSCAASGGSLSNYVLGWFRQAPGKEREFVAAINWRGDITIGPPNVEGRFTISRDNAKNTGYLQMNSLRPDDTAVYYCGAGTPLNPGAYIYDWSYDYWGQGTLVTVSS |
| RSV437 V20D | 81 | DVQLVESGGGLVQPGGSLRLSCAASGGSLSNYVLGWFRQAPGKEREFVAAINWRGDITIGPPNVEGRFTISRDNAKNTGYLQMNSLRPDDTAVYYCGAGTPLNPGAYIYDWSYDYWGQGTLVTVSSGGGGSGGGGSGGGGSEVQLVESGGGLVQPGGSLRLSCAASGGSLSNYVLGWFRQAPGKEREFVAAINWRGDITIGPPNVEGRFTISRDNAKNTGYLQMNSLRPDDTAVYYCGAGTPLNPGAYIYDWSYDYWGQGTLVTVSSGGGGSGGGGSGGGGSEVQLVESGGGLVQPGGSLRLSCAASGGSLSNYVLGWFRQAPGKEREFVAAINWRGDITIGPPNVEGRFTISRDNAKNTGYLQMNSLRPDDTAVYYCGAGTPLNPGAYIYDWSYDYWGQGTLVTVSS |
| RSV438 V22 | 82 | EVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGQGTLVTVSSGGGGSGGGGSGGGGSEVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGQGTLVTVSSGGGGSGGGGSGGGGSEVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGQGTLVTVSS |
| RSV439 V26 | 83 | EVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGRGTLVTVSSGGGGSGGGGSGGGGSEVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGRGTLVTVSSGGGGSGGGGSGGGGSEVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPLNPGAYIYDWSYDYWGRGTLVTVSS |
| RSV440 V26D | 84 | DVQLVESGGGLVQPGGSLRLSCAASGGSLSNYVLGWFRQAPGKEREFVAAINWRGDITIGPPNVEGRFTISRDNAKNTGYLQMNSLRPEDTAVYYCGAGTPL |

TABLE A-3-continued

Amino acid sequences of preferred polypeptides of the invention

| Nanobody® | SEQ ID NO: | Sequence |
|---|---|---|
| | | NPGAYIYDWSYDYWGRGTLVTVSSGGGGSGGGGSGGGGSEVQLVES-GGGLV QPGGSLRLSCAASGGSLSNYVLGWFRQAPGKEREFVAAINWRGDITIG-PPN VEGRFTISRDNAKNTGYLQMNSLRPEDTAVYYCGAGTPLNPGAYIYD-WSYD YWGRGTLVTVSSGGGGSGGGGSGGGGSEVQLVESGGGLVQPGGSLRLS-CAA SGGSLSNYVLGWFRQAPGKEREFVAAINWRGDITIGPPNVEGR-FTISRDNA KNTGYLQMNSLRPEDTAVYYCGAGTPLNPGAYIYDWSYDYWGRGTLVT-VSS |
| RSV441 V22D | 85 | DVQLVESGGGLVQPGGSLRLSCAASGGSLSNYVLGWFRQAPGK-EREFVAAI NWRGDITIGPPNVEGRFTISRDNAKNTGYLQMNSLRPEDTAVYYC-GAGTPL NPGAYIYDWSYDYWGQGTLVTVSSGGGGSGGGGSGGGGSEVQLVES-GGGLV QPGGSLRLSCAASGGSLSNYVLGWFRQAPGKEREFVAAINWRGDITIG-PPN VEGRFTISRDNAKNTGYLQMNSLRPEDTAVYYCGAGTPLNPGAYIYD-WSYD YWGQGTLVTVSSGGGGSGGGGSGGGGSEVQLVESGGGLVQPGGSLRLS-CAA SGGSLSNYVLGWFRQAPGKEREFVAAINWRGDITIGPPNVEGR-FTISRDNA KNTGYLQMNSLRPEDTAVYYCGAGTPLNPGAYIYDWSYDYWGQGTLVT-VSS |

TABLE A-4

Amino acid sequences of linkers

| Linker | SEQ ID NO: | Sequences |
|---|---|---|
| 5GS | 86 | GGGGS |
| 7GS | 87 | SGGSGGS |
| GS8 | 88 | GGGGSGGGS |
| 9GS | 89 | GGGGSGGGS |
| 10GS | 90 | GGGGSGGGGS |
| 15GS | 91 | GGGGSGGGGSGGGGS |
| 18GS | 92 | GGGGSGGGGSGGGGGGS |
| 20GS | 93 | GGGGSGGGGSGGGGSGGGGS |
| 25GS | 94 | GGGGSGGGGSGGGGSGGGGSGGGGS |
| 30GS | 95 | GGGGSGGGGSGGGGSGGGGSGGGGSGGGGS |
| 35GS | 96 | GGGGSGGGGSGGGGSGGGGSGGGGSGGGGSGGGGS |
| G1 hinge | 97 | EPKSCDKTHTCPPCP |
| 9GS-G1 hinge | 98 | GGGGSGGGSEPKSCDKTHTCPPCP |
| Llama upper long hinge region | 99 | EPKTPKPQPAAA |
| G3 hinge | 100 | ELKTPLGDTTHTCPRCPEPKSCDTPPPCPRCPE PKSCDTPPPCPRCPEPKSCDTPPPCPRCP |
| Ala | 101 | AAA |

TABLE B-1

Preclinical and clinical studies used in the PBPK modeling

| Type of study | Species | Administration | Dose |
|---|---|---|---|
| Study 1: Initial PK study | Rats | IV Pulmonary Nasal inhalation Variable inhalation time, fixed aerosol concentration and particle size distribution | 5 mg/kg single dose 10 to 250 mg/kg single dose |

TABLE B-1-continued

Preclinical and clinical studies used in the PBPK modeling

| Type of study | Species | Administration | Dose |
|---|---|---|---|
| Study 2: Toxicity study | Rats | IV | 5 to 50 mg/kg once daily for 14 days |
| Study 3: Cardiovascular safety pharmacology study | Beagle dogs | IV | Ascending dose of 3 mg/kg, 10 mg/kg and 30 mg/kg |
| Study 4: Toxicity study | Rats | Pulmonary Nasal inhalation Fixed inhalation time, variable aerosol concentration and particle size distribution | 15 mg/kg, 50 mg/kg, 150 mg/kg multiple dosing |
| Study 5: Clinical study | Humans | Pulmonary Bolus inhalation (aerosol is not present during whole inhalation) Retro breathing (oral inhalation and exhalation via nose) | 7, 21, 70, 140, 210 mg single dosing and 70 mg and 105 mg B.I.D. |
| Study 6: Clinical study | Humans | IV Oral inhalation | 0.3 mg/kg single dosing, 5 min infusion 200 mg single and multiple dosing |

TABLE B-2

Body weight categories for dose selection for pulmonary administration of the polypeptide of the invention (such as SEQ ID NO: 71)

| | Weight category | Fill Volume | Fill Dose | Nebulisation time[a] | Nominal dose (mg/kg) | Inhaled Dose (mg/kg) | Deposited dose[b] (mg/kg) |
|---|---|---|---|---|---|---|---|
| 1 kg incremental step | 5.0-6.0 kg | 0.150 mL | 7.5 mg | ~45 seconds | 1.50-1.25 | 0.30-0.25 | 0.030-0.025 |
| | 6.1-8.0 kg | 0.200 mL | 10.0 mg | ~60 seconds | 1.64[c]-1.25 | 0.33-0.25 | 0.033-0.025 |
| | 8.1-10.0 kg | 0.250 mL | 12.5 mg | ~75 seconds | 1.54-1.25 | 0.31-0.25 | 0.031-0.025 |
| 2 kg incremental steps | 10.1-12.0 kg | 0.300 mL | 15.0 mg | ~90 seconds | 1.49-1.25 | 0.30-0.25 | 0.030-0.025 |
| | 12.1-14.0 kg | 0.350 mL | 17.5 mg | ~105 seconds | 1.45-1.25 | 0.29-0.25 | 0.029-0.025 |
| | 14.1-16.0 kg | 0.400 mL | 20.0 mg | ~120 seconds | 1.42-1.25 | 0.28-0.25 | 0.028-0.025 |

[a]Based on the device output rate of ~200 μL/min.
[b]The deposited dose required to reach the target concentration (9 μg/mL) is 0.024 mg/kg.
[c]Safety margin calculations were based on the highest nominal dose (1.64 mg/kg)

TABLE B-3

Measured endpoints in the neonatal lamb study

| Endpoint | Methods |
|---|---|
| Body weights | Body weights of each animal was measured daily using an electronic balance (DP-6200, Yamato Corp.) and was recorded in the individual lamb datasheets |
| Heart and respiratory rates | Heart and respiratory rates were measured daily by auscultation with a stethoscope and palpation with the fingers on the rib cage and visual inspection of rib cage movement. |
| Body Temperature | Rectal temperatures were measured daily with an electronic thermometer |
| Wheeze, expiratory efforts and malaise | Respiratory distress or malaise was assessed daily for each lamb by auscultation or by visual inspection |
| Blood oxygenation | Oxygenation levels of arterial blood were assessed daily using a pulse oximeter (PalmSAT 2500A VET, Nonin Medical, Inc Plymouth, MN, USA). The probe of the oximeter was manually secured at the root of the tail (a naturally hairless site), nearest the anus. The femoral artery was then palpated to measure the pulse rate and was compared with the pulse rate displayed on the oximeter. The SpO2 values were recorded only if the two pulse rates were within 20% of each other. |
| Gross viral lesions | Percentage parenchymal involvement (gross lesions) was scored for each individual lung lobe. The percentage of a specific lobe tissue that was affected in relation to the overall lobe tissue being scored was estimated based on the investigator's judgment. |

TABLE B-3-continued

Measured endpoints in the neonatal lamb study

| Endpoint | Methods |
|---|---|
| Consolidation histological score | A histologic score was determined by evaluating percent lung involvement. Alveolar involvement was defined by reduced expansion of alveolar lumen due to alveolar septal infiltration of neutrophils, lymphocytes, plasma cells, and type II cell hypertrophy along with intraluminal accumulation of neutrophils, macrophages, and small amounts of cell debris. The score was defined by converting the observed percentage ranges to a simple integer based on a composite lesion scale: 0% involvement = 0, 1-9% involvement = 1, 10-39% involvement = 2, 40-69% involvement = 3, 70-100% involvement = 4. |
| Immunohistochemistry | Immunohistochemistry for detection, localization, and quantification of hRSV antigen in lung was performed on paraffin-embedded tissues from 4 lung lobes (2 lung pieces/non-BALF washed lobes for immunohistochemistry and histopathology) using a method similar to what has been described previously [1, 2] but with the following variations: instead of Pronase E antigen retrieval, heated buffer antigen retrieval was performed in TRIS-EDTA-0.05% Tween 20, pH 9.0. Sections were then blocked for 15 minutes with 3% BSA in TBS-0.05% Tween 20, pH 7.4 followed by additional blocking with 20% normal swine serum in TBS-tween for 15 minutes. Primary polyclonal goat anti-hRSV antibody (EMD/Millipore/Chennicon, Billerica, MA) was applied 1:500 for 1.5 hours at 22° C. Secondary detection was performed using biotinylated rabbit anti-goat secondary antibody (Kirkegaard-Perry Labs, Gaithersburg, MD) for 45 minutes followed by streptavidin-conjugated HRP for 30 minutes. Development of the colour was performed using Nova Red (Vector, Burlingame, CA) for 90 seconds. Slides (two lung samples) were evaluated and scored as follows: 20 unique 10X fields on each slide were assessed for antigen staining and the number of affected bronchi/bronchioles and alveoli per field were counted. |
| Focus forming unit assay | Serially-diluted BALF samples were applied to HEp-2 cells grown to 70% confluence in 12-well culture plates (Fisher Scientific, Hanover, IL) in DMEM media (Mediatech, Inc., Manassas, VA) supplemented to 10% with heat-inactivated fetal bovine serum (FBS) (Atlanta Biologicals, Atlanta, GA) and 50 μg/mL kanamycin sulfate (Invitrogen). Each sample was analyzed undiluted and at four additional serial-dilutions of 1:10, 1:100, 1:1,000 and 1:10,000 in duplicate. Following a 48 hour incubation at 37° C., 5% CO2, the cells were fixed with cold 60% acetone/40% methanol solution for 1 minute. Overnight primary antibody (Goat polyclonal Ab to hRSV [all antigens], Millipore, Billerica, MA) incubation was then followed by washing and secondary antibody (Rabbit anti-Goat Fab' conjugated to AlexaFluor 488, Invitrogen) incubation for 30 minutes. Plates were rinsed and inspected for the presence of fluorescing foci of infection using the FITC/GFP filter on an inverted fluorescence microscope (Olympus CKX41, Center Valley, PA). Five or more fluorescing cells were counted as single focal events. |
| qPCR | Viral RNA was quantified in both nasal cavity (nasal washes) and lung (BALF from the right caudal lobe and lung homogenate from pooled tissue samples) for all animals using reverse transcription quantitative polymerase chain reaction (RT-qPCR). RNA isolation from BALF, nasal washes and lung slurry was performed as per manufacturer's instructions (Invitrogen), followed by DNase treatment (Ambion, TURBO DNase, Austin, TX). Absorbance readings at 260 and 280 nm were measured to determine RNA concentration and purity. RT-qPCR was carried out using One-Step Fast qRT-PCR Kit master mix (Quanta, BioScience, Gaithersburg, MD) in a GeneAmp 5700 Sequence Detection System (Applied Biosystems, Carlsbad, CA) employing PREXCEL-Q for all set-up calculations. Primers and probes for the hRSV M37 nucleoprotein were designed with ABI Primer Express 2.0 based on hRSV accession number M74568. |
| SEQ ID NO: 71 in epithelial lining fluid | Qualified ELISA methods were used for the quantification of SEQ ID NO: 71 in lamb BALF. The SEQ ID NO: 71 concentration in the epithelial lining fluid at necropsy was calculated based on the SEQ ID NO: 71 concentration measured in BALF and following normalization by the Urea method [3] |

[1] Olivier, A., et al., Human respiratory syncytial virus A2 strain replicates and induces innate immune responses by respiratory epithelia of neonatal lambs. International journal of experimental pathology, 2009. 90(4): p. 431-8

[2] Olivier, A. K., et al., Exogenous administration of vascular endothelial growth factor prior to human respiratory syncytial virus a2 infection reduces pulmonary pathology in neonatal lambs and alters epithelial innate immune responses. Experimental lung research, 2011. 37(3): p. 131-43.

[3] Rennard, S. I., et al., Estimation of volume of epithelial lining fluid recovered by lavage using urea as marker of dilution. Journal of applied physiology, 1986. 60(2): p. 532-8.

TABLE B-4

Clinical composite scoring criteria

| Parameter | Score 0 | Score 1 |
|---|---|---|
| Body weight | % increase on day 6 is >20% of day 0 | % increase on day 6 is ≤20% of day 0 |
| Blood oxygenation | % decrease on all days after first dose is ≤10% of day 0 | % decrease any day after first dose is >10% of day 0 |
| Body temperature | % increase on all days after first dose ≤10% of day 0 | % increase any day after first dose >10% of day 0 |
| Respiratory rates | % increase on all days after first dose ≤10% of day 0 | % increase any day after first dose >10% of day 0 |
| Expiratory efforts | Absent on all days after first dose | Present on any day after first dose |
| Wheeze | Absent on all days after first dose | Present on any day after first dose |
| Malaise | Absent on all days after first dose | Present on any day after first dose |
| Minimum-maximum total score/lamb | 0 | 7 |

TABLE B-5

Viral loads in neonatal lambs treated with SEQ ID NO: 71 or vehicle

| Study | SEQ ID NO: 71 delivered dose$ | Treatment regimen | Cultivatable virus — Viral load reduction versus vehicle ($\log_{10}$ FFU/mL of BALF or nasal wash) — Nasal wash | BALF | Viral transcripts — Reduction in viral RNA versus vehicle ($\log_{10}$ viral RNA copies/mL for nasal wash and BALF or $\log_{10}$ viral RNA copies/mg lung) — Nasal wash | BALF | Lung tissue |
|---|---|---|---|---|---|---|---|
| 1 | Vehicle | day 1, 2, 3, 4, 5 | ND | [4.49 ± 0.43] | ND | [6.39 ± 0.1] | [6.02 ± 0.13] |
|   | 11 mg |   |   | ND |   | 1.82 | 1.21 |
|   | 36 mg |   |   | ND |   | 1.44 | 0.83 |
|   | 110 mg |   |   | ND |   | 1.79 | 1.88 |
| 2 | Vehicle | day 3, 4, 5 | [0.99 ± 0.3] | [4.83 ± 0.04] | [2.89 ± 0.34] | [7.15 ± 0.2] | [7.63 ± 0.07] |
|   | 11 mg |   | 0.29 | 4.13 | 2.59 | 1.25 | 1.84 |
|   | 110 mg |   | 0.29 | 4.13 | −0.92 | 0.14 | 0.54 |
| 3 | Vehicle | day 3, 4, 5 | ND | [4.98 ± 0.41] | ND | [7.26 ± 0.3] | [5.47 ± 0.21] |
|   | 11 mg |   |   | 4.11 |   | 0.55 | 0.47 |

Listings of virology results obtained in hRSV infected neonatal lambs for independently performed studies.
$Delivered dose is defined as the total nebulised drug (ie nebulised volume × concentration of SEQ ID NO: 71)
ND: not done
Note:
For statistical analysis 0 foci were counted as 0.7 $\log_{10}$ FFU/mL of BALF or nasal wash for cultivatable virus and viral RNA copies below detection limit were counted as 0.3 $\log_{10}$ viral RNA copies/mL of nasal wash.
Mean values for cultivatable virus and viral transcript assessments in the vehicle groups are marked in each column as [mean ± standard error].

TABLE B-6

Body weight categories for dose selection for pulmonary administration of the polypeptide of the invention (such as SEQ ID NO: 71)

|   | Weight category | Fill Volume | Fill Dose | Nebulisation time[a] | Nominal dose (mg/kg) | Inhaled Dose (mg/kg) | Deposited dose[b] (mg/kg) |
|---|---|---|---|---|---|---|---|
| 0.5 kg incremental step | 3.5-3.9 kg | 0.100 mL | 5.0 mg | ~30 seconds | 1.43-1.28 | 0.39-0.26 | 0.029-0.026 |
| 1 kg incremental step | 4.0-5.0 kg | 0.130 mL | 6.5 mg | ~40 seconds | 1.63-1.30 | 0.33-0.26 | 0.033-0.026 |
|   | 5.1-6.0 kg | 0.150 mL | 7.5 mg | ~45 seconds | 1.47-1.25 | 0.29-0.25 | 0.029-0.025 |
| 2 kg incremental steps | 6.1-8.0 kg | 0.200 mL | 10.0 mg | ~60 seconds | 1.64[c]-1.25 | 0.33-0.25 | 0.033-0.025 |
|   | 8.1-10.0 kg | 0.250 mL | 12.5 mg | ~75 seconds | 1.54-1.25 | 0.31-0.25 | 0.031-0.025 |
|   | 10.1-12.0 kg | 0.300 mL | 15.0 mg | ~90 seconds | 1.49-1.25 | 0.30-0.25 | 0.030-0.025 |

TABLE B-6-continued

Body weight categories for dose selection for pulmonary administration of the polypeptide of the invention (such as SEQ ID NO: 71)

|  | Weight category | Fill Volume | Fill Dose | Nebulisation time[a] | Nominal dose (mg/kg) | Inhaled Dose (mg/kg) | Deposited dose[b] (mg/kg) |
|---|---|---|---|---|---|---|---

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser
            115                 120                 125

<210> SEQ ID NO 3
<211> LENGTH: 126
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 4
<211> LENGTH: 126
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

```
<210> SEQ ID NO 5
<211> LENGTH: 126
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Leu Glu Ser Gly Gly Gly Leu Val Gln Pro Gly Gly
1               5                   10                  15

Ser Leu Arg Ile Ser Cys Ala Ala Ser Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 6
<211> LENGTH: 126
<212> TYPE: PRT
<213> ORGANISM: Artificial Sequence
<220> FEATURE:
<223> OTHER INFORMATION: Nanobody sequence

<400> SEQUENCE: 6

Asp Val Gln Leu Leu Glu Ser Gly Gly Gly Leu Val Gln Pro Gly Gly
1               5                   10                  15

Ser Leu Arg Ile Ser Cys Ala Ala Ser Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 7
<211> LENGTH: 126
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Leu Glu Ser Gly Gly Gly Leu Val Gln Pro Gly Gly
1               5                   10                  15
```

-continued

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 8
<211> LENGTH: 126
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Leu Glu Ser Gly Gly Gly Leu Val Gln Pro Gly Gly
 1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 9
<211> LENGTH: 126
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
 50                  55                  60

Glu Gly Arg Phe Thr Ile Ser Arg Asp Asn Ala Lys Asn Thr Leu Tyr

```
                65                  70                  75                  80
Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 10
<211> LENGTH: 126
<212> TYPE: PRT
<213> ORGANISM: Artificial Sequence
<220> FEATURE:
<223> OTHER INFORMATION: Nanobody sequence

<400> SEQUENCE: 10

Asp Val Gln Leu Leu Glu Ser Gly Gly Gly Leu Val Gln Pro Gly Gly
1               5                   10                  15

Ser Leu Arg Leu Ser Cys Ala Ala Ser Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Asp Asp Ile Thr Ile Gly Pro Pro Asn Val
        50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Leu Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125
```

<210> SEQ ID NO 12
<211> LENGTH: 126
<212> TYPE: PRT
<213> ORGANISM: Artificial Sequence
<220> FEATURE:
<223> OTHER INFORMATION: Nanobody sequence

<400> SEQUENCE: 12

```
Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 13
<211> LENGTH: 126
<212> TYPE: PRT
<213> ORGANISM: Artificial Sequence
<220> FEATURE:
<223> OTHER INFORMATION: Nanobody sequence

<400> SEQUENCE: 13

```
Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 14
<211> LENGTH: 126
<212> TYPE: PRT
<213> ORGANISM: Artificial Sequence
<220> FEATURE:
<223> OTHER INFORMATION: Nanobody sequence

<400> SEQUENCE: 14

Glu Val Gln Leu Leu Glu Ser Gly Gly Gly Leu Val Gln Pro Gly Gly

-continued

```
                 1               5                  10                 15
            Ser Leu Ser Ile Ser Cys Ala Ala Ser Gly Gly Ser Leu Ser Asn Tyr
                             20                  25                  30

Val Leu Gly Trp Phe Arg Gln Ala Pro Gly Lys Gly Arg Glu Phe Val
                             35                  40                  45

Ala Ala Ile Asn Trp Arg Gly Asp Ile Thr Ile Gly Pro Pro Asn Val
                             50                  55                  60

Glu Gly Arg Phe Thr Ile Ser Arg Asp Asn Ala Lys Asn Thr Gly Tyr
            65                  70                  75                  80

Leu Gln Met Asn Ser Leu Ala Pro Asp Asp Thr Ala Val Tyr Tyr Cys
                             85                  90                  95

Gly Ala Gly Thr Pro Leu Asn Pro Gly Ala Tyr Ile Tyr Asp Trp Ser
                             100                 105                 110

Tyr Asp Tyr Trp Gly Gln Gly Thr Leu Val Thr Val Ser Ser
                             115                 120                 125
```

<210> SEQ ID NO 15
<211> LENGTH: 126
<212> TYPE: PRT
<213> ORGANISM: Artificial Sequence
<220> FEATURE:
<223> OTHER INFORMATION: Nanobody sequence

<400> SEQUENCE: 15

```
            Glu Val Gln Leu Leu Glu Ser Gly Gly Gly Leu Val Gln Ala Gly Gly
            1               5                  10                 15

Ser Leu Ser Ile Ser Cys Ala Ala Ser Gly Gly Ser Leu Ser Asn Tyr
                             20                  25                  30

Val Leu Gly Trp Phe Arg Gln Ala Pro Gly Lys Gly Arg Glu Phe Val
                             35                  40                  45

Ala Ala Ile Asn Trp Arg Gly Asp Ile Thr Ile Gly Pro Pro Asn Val
                             50                  55                  60

Glu Gly Arg Phe Thr Ile Ser Arg Asp Asn Ala Lys Asn Thr Gly Tyr
            65                  70                  75                  80

Leu Gln Met Asn Ser Leu Ala Pro Asp Asp Thr Ala Val Tyr Tyr Cys
                             85                  90                  95

Gly Ala Gly Thr Pro Leu Asn Pro Gly Ala Tyr Ile Tyr Asp Trp Ser
                             100                 105                 110

Tyr Asp Tyr Trp Gly Gln Gly Thr Leu Val Thr Val Ser Ser
                             115                 120                 125
```

<210> SEQ ID NO 16
<211> LENGTH: 126
<212> TYPE: PRT
<213> ORGANISM: Artificial Sequence
<220> FEATURE:
<223> OTHER INFORMATION: Nanobody sequence

<400> SEQUENCE: 16

```
            Glu Val Gln Leu Leu Glu Ser Gly Gly Gly Leu Val Gln Pro Gly Gly
            1               5                  10                 15

Ser Leu Ser Ile Ser Cys Ala Ala Ser Gly Gly Ser Leu Ser Asn Tyr
                             20                  25                  30

Val Leu Gly Trp Phe Arg Gln Ala Pro Gly Lys Glu Arg Glu Phe Val
                             35                  40                  45

Ala Ala Ile Asn Trp Arg Gly Asp Ile Thr Ile Gly Pro Pro Asn Val
                             50                  55                  60
```

```
Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 17
<211> LENGTH: 126
<212> TYPE: PRT
<213> ORGANISM: Artificial Sequence
<220> FEATURE:
<223> OTHER INFORMATION: Nanobody sequence

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 18
<211> LENGTH: 126
<212> TYPE: PRT
<213> ORGANISM: Artificial Sequence
<220> FEATURE:
<223> OTHER INFORMATION: Nanobody sequence

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

```
<210> SEQ ID NO 19
<211> LENGTH: 126
<212> TYPE: PRT
<213> ORGANISM: Artificial Sequence
<220> FEATURE:
<223> OTHER INFORMATION: Nanobody sequence

<400> SEQUENCE: 19

Glu Val Gln Leu Leu Glu Ser Gly Gly Gly Leu Val Gln Ala Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 20
<211> LENGTH: 126
<212> TYPE: PRT
<213> ORGANISM: Artificial Sequence
<220> FEATURE:
<223> OTHER INFORMATION: Nanobody sequence

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 21
<211> LENGTH: 126
<212> TYPE: PRT
<213> ORGANISM: Artificial Sequence
<220> FEATURE:
<223> OTHER INFORMATION: Nanobody sequence

<400> SEQUENCE: 21
```

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 22
<211> LENGTH: 126
<212> TYPE: PRT
<213> ORGANISM: Artificial Sequence
<220> FEATURE:
<223> OTHER INFORMATION: Nanobody sequence

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 23
<211> LENGTH: 126
<212> TYPE: PRT
<213> ORGANISM: Artificial Sequence
<220> FEATURE:
<223> OTHER INFORMATION: Nanobody sequence

<400> SEQUENCE: 23

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 24
<211> LENGTH: 126
<212> TYPE: PRT
<213> ORGANISM: Artificial Sequence
<220> FEATURE:
<223> OTHER INFORMATION: Nanobody sequence

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 25
<211> LENGTH: 126
<212> TYPE: PRT
<213> ORGANISM: Artificial Sequence
<220> FEATURE:
<223> OTHER INFORMATION: Nanobody sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser

-continued

```
            115                 120                 125

<210> SEQ ID NO 26
<211> LENGTH: 126
<212> TYPE: PRT
<213> ORGANISM: Artificial Sequence
<220> FEATURE:
<223> OTHER INFORMATION: Nanobody sequence

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Nanobody sequence

<400> SEQUENCE: 27

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Nanobody sequence

<400> SEQUENCE: 28
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
50                      55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Nanobody sequence

<400> SEQUENCE: 29

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
50                      55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 30
<211> LENGTH: 126
<212> TYPE: PRT
<213> ORGANISM: Artificial Sequence
<220> FEATURE:
<223> OTHER INFORMATION: Nanobody sequence

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val

```
                    50                  55                  60
Glu Gly Arg Phe Thr Ile Ser Arg Asp Asn Ala Lys Asn Thr Gly Tyr
 65                  70                  75                  80

Leu Gln Met Asn Ser Leu Ala Pro Asp Asp Thr Ala Val Tyr Tyr Cys
                     85                  90                  95

Gly Ala Gly Thr Pro Leu Asn Pro Gly Ala Tyr Ile Tyr Asp Trp Ser
                100                 105                 110

Tyr Asp Tyr Trp Gly Arg Gly Thr Leu Val Thr Val Ser Ser
                115                 120                 125

<210> SEQ ID NO 31
<211> LENGTH: 126
<212> TYPE: PRT
<213> ORGANISM: Artificial Sequence
<220> FEATURE:
<223> OTHER INFORMATION: Nanobody sequence

<400> SEQUENCE: 31

Glu Val Gln Leu Val Glu Ser Gly Gly Gly Leu Val Gln Pro Gly Gly
 1               5                  10                  15

Ser Leu Arg Leu Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
 65                  70                  75                  80

Leu Gln Met Asn Ser Leu Arg Pro Asp Asp Thr Ala Val Tyr Tyr Cys
                     85                  90                  95

Gly Ala Gly Thr Pro Leu Asn Pro Gly Ala Tyr Ile Tyr Asp Trp Ser
                100                 105                 110

Tyr Asp Tyr Trp Gly Arg Gly Thr Leu Val Thr Val Ser Ser
                115                 120                 125

<210> SEQ ID NO 32
<211> LENGTH: 126
<212> TYPE: PRT
<213> ORGANISM: Artificial Sequence
<220> FEATURE:
<223> OTHER INFORMATION: Nanobody sequence

<400> SEQUENCE: 32

Glu Val Gln Leu Val Glu Ser Gly Gly Gly Leu Val Gln Pro Gly Gly
 1               5                  10                  15

Ser Leu Arg Leu Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
 65                  70                  75                  80

Leu Gln Met Asn Ser Leu Ala Pro Glu Asp Thr Ala Val Tyr Tyr Cys
                     85                  90                  95

Gly Ala Gly Thr Pro Leu Asn Pro Gly Ala Tyr Ile Tyr Asp Trp Ser
                100                 105                 110
```

```
Tyr Asp Tyr Trp Gly Arg Gly Thr Leu Val Thr Val Ser Ser
        115                 120                 125

<210> SEQ ID NO 33
<211> LENGTH: 126
<212> TYPE: PRT
<213> ORGANISM: Artificial Sequence
<220> FEATURE:
<223> OTHER INFORMATION: Nanobody sequence

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
        115                 120                 125

<210> SEQ ID NO 34
<211> LENGTH: 126
<212> TYPE: PRT
<213> ORGANISM: Artificial Sequence
<220> FEATURE:
<223> OTHER INFORMATION: Nanobody sequence

<400> SEQUENCE: 34

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
        115                 120                 125

<210> SEQ ID NO 35
<211> LENGTH: 30
<212> TYPE: PRT
<213> ORGANISM: Artificial Sequence
<220> FEATURE:
<223> OTHER INFORMATION: Framework sequence
```

-continued

```
<400> SEQUENCE: 35

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Framework sequence

<400> SEQUENCE: 36

Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Framework sequence

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Framework sequence

<400> SEQUENCE: 38

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Framework sequence

<400> SEQUENCE: 39

Asp Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Framework sequence
```

```
<400> SEQUENCE: 40

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Framework sequence

<400> SEQUENCE: 41

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Framework sequence

<400> SEQUENCE: 42

Glu Val Gln Leu Leu Glu Ser Gly Gly Gly Leu Val Gln Ala Gly Gly
1               5                   10                  15

Ser Leu Ser Ile Ser Cys Ala Ala Ser Gly Gly Ser Leu Ser
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Framework sequence

<400> SEQUENCE: 43

Glu Val Gln Leu Leu Glu Ser Gly Gly Gly Leu Val Gln Ala Gly Gly
1               5                   10                  15

Ser Leu Arg Leu Ser Cys Ala Ala Ser Gly Gly Ser Leu Ser
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Framework sequence

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 45
<211> LENGTH: 30
<212> TYPE: PRT
<213> ORGANISM: Artificial Sequence
<220> FEATURE:
```

<223> OTHER INFORMATION: Framework sequence

<400> SEQUENCE: 45

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 46
<211> LENGTH: 5
<212> TYPE: PRT
<213> ORGANISM: Artificial Sequence
<220> FEATURE:
<223> OTHER INFORMATION: CDR sequence

<400> SEQUENCE: 46

Asn Tyr Val Leu Gly
1               5

<210> SEQ ID NO 47
<211> LENGTH: 14
<212> TYPE: PRT
<213> ORGANISM: Artificial Sequence
<220> FEATURE:
<223> OTHER INFORMATION: Framework sequence

<400> SEQUENCE: 47

Trp Phe Arg Gln Ala Pro Gly Lys Glu Arg Glu Phe Val Ala
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Framework sequence

<400> SEQUENCE: 48

Trp Phe Arg Gln Ala Pro Gly Lys Gly Arg Glu Phe Val Ala
1               5                   10

<210> SEQ ID NO 49
<211> LENGTH: 17
<212> TYPE: PRT
<213> ORGANISM: Artificial Sequence
<220> FEATURE:
<223> OTHER INFORMATION: CDR sequence

<400> SEQUENCE: 49

Ala Ile Asn Trp Arg Gly Asp Ile Thr Ile Gly Pro Pro Asn Val Glu
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: CDR sequence

<400> SEQUENCE: 50

Ala Ile Asn Trp Arg Asp Asp Ile Thr Ile Gly Pro Pro Asn Val Glu
1               5                   10                  15

Gly

<210> SEQ ID NO 51
<211> LENGTH: 32
<212> TYPE: PRT
<213> ORGANISM: Artificial Sequence
<220> FEATURE:
<223> OTHER INFORMATION: Framework sequence

<400> SEQUENCE: 51

Arg Phe Thr Ile Ser Arg Asp Asn Ala Lys Asn Thr Gly Tyr Leu Gln
1               5                   10                  15

Met Asn Ser Leu Ala Pro Asp Asp Thr Ala Val Tyr Tyr Cys Gly Ala
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Framework sequence

<400> SEQUENCE: 52

Arg Phe Thr Ile Ser Arg Asp Asn Ala Lys Asn Thr Leu Tyr Leu Gln
1               5                   10                  15

Met Asn Ser Leu Ala Pro Glu Asp Thr Ala Val Tyr Tyr Cys Gly Ala
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Framework sequence

<400> SEQUENCE: 53

Arg Phe Thr Ile Ser Arg Asp Asn Ser Lys Asn Thr Leu Tyr Leu Gln
1               5                   10                  15

Met Asn Ser Leu Ala Pro Glu Asp Thr Ala Val Tyr Tyr Cys Gly Ala
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Framework sequence

<400> SEQUENCE: 54

Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Val Tyr Tyr Cys Gly Ala
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Framework sequence

<400> SEQUENCE: 55

Arg Phe Thr Ile Ser Arg Asp Asn Ser Lys Asn Thr Leu Tyr Leu Gln
1               5                   10                  15

Met Asn Ser Leu Arg Pro Asp Asp Thr Ala Val Tyr Tyr Cys Gly Ala
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Framework sequence

<400> SEQUENCE: 56

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Gly Ala
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Framework sequence

<400> SEQUENCE: 57

Arg Phe Thr Ile Ser Arg Asp Asn Ala Lys Asn Thr Leu Tyr Leu Gln
1               5                   10                  15

Met Asn Ser Leu Ala Pro Asp Asp Thr Ala Val Tyr Tyr Cys Gly Ala
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Framework sequence

<400> SEQUENCE: 58

Arg Phe Thr Ile Ser Arg Asp Asn Ala Lys Asn Thr Gly Tyr Leu Gln
1               5                   10                  15

Met Asn Ser Leu Ala Pro Glu Asp Thr Ala Val Tyr Tyr Cys Gly Ala
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Framework sequence

<400> SEQUENCE: 59

Arg Phe Thr Ile Ser Arg Asp Asn Ala Lys Asn Thr Gly Tyr Leu Gln
1               5                   10                  15

Met Asn Ser Leu Arg Pro Asp Asp Thr Ala Val Tyr Tyr Cys Gly Ala
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Framework sequence

<400> SEQUENCE: 60

Arg Phe Thr Ile Ser Arg Asp Asn Ala Lys Asn Thr Gly Tyr Leu Gln
1               5                   10                  15

Met Asn Ser Leu Arg Pro Glu Asp Thr Ala Val Tyr Tyr Cys Gly Ala

```
                     20                  25                  30

<210> SEQ ID NO 61
<211> LENGTH: 17
<212> TYPE: PRT
<213> ORGANISM: Artificial Sequence
<220> FEATURE:
<223> OTHER INFORMATION: CDR sequence

<400> SEQUENCE: 61

Gly Thr Pro Leu Asn Pro Gly Ala Tyr Ile Tyr Asp Trp Ser Tyr Asp
1               5                   10                  15

Tyr

<210> SEQ ID NO 62
<211> LENGTH: 11
<212> TYPE: PRT
<213> ORGANISM: Artificial Sequence
<220> FEATURE:
<223> OTHER INFORMATION: Framework sequence

<400> SEQUENCE: 62

Trp Gly Arg Gly Thr Gln Val Thr Val Ser Ser
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Framework sequence

<400> SEQUENCE: 63

Trp Gly Gln Gly Thr Leu Val Thr Val Ser Ser
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Framework sequence

<400> SEQUENCE: 64

Trp Gly Arg Gly Thr Leu Val Thr Val Ser Ser
1               5                   10

<210> SEQ ID NO 65
<211> LENGTH: 408
<212> TYPE: PRT
<213> ORGANISM: Artificial Sequence
<220> FEATURE:
<223> OTHER INFORMATION: Nanobody sequence

<400> SEQUENCE: 65

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
```

```
            65                  70                  75                  80
Leu Gln Met Asn Ser Leu Ala Pro Asp Asp Thr Ala Val Tyr Tyr Cys
                    85                  90                  95

Gly Ala Gly Thr Pro Leu Asn Pro Gly Ala Tyr Ile Tyr Asp Trp Ser
                100                 105                 110

Tyr Asp Tyr Trp Gly Arg Gly Thr Gln Val Thr Val Ser Ser Gly Gly
            115                 120                 125

Gly Gly Ser Gly Gly Gly Ser Gly Gly Gly Ser Glu Val Gln
130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
                180                 185                 190

Asn Trp Arg Gly Asp Ile Thr Ile Gly Pro Pro Asn Val Glu Gly Arg
            195                 200                 205

Phe Thr Ile Ser Arg Asp Asn Ala Lys Asn Thr Gly Tyr Leu Gln Met
210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Ala Gly Gly Ser Leu Ser Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Ala Pro Asp Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405

<210> SEQ ID NO 66
<211> LENGTH: 384
<212> TYPE: PRT
<213> ORGANISM: Artificial Sequence
<220> FEATURE:
<223> OTHER INFORMATION: Nanobody sequence

<400> SEQUENCE: 66

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
```

```
            20                  25                  30
Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
            50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Ala Ala
            115                 120                 125

Ala Glu Val Gln Leu Val Glu Ser Gly Gly Gly Leu Val Gln Ala Gly
            130                 135                 140

Gly Ser Leu Ser Ile Ser Cys Ala Ala Ser Gly Gly Ser Leu Ser Asn
145                 150                 155                 160

Tyr Val Leu Gly Trp Phe Arg Gln Ala Pro Gly Lys Glu Arg Glu Phe
                165                 170                 175

Val Ala Ala Ile Asn Trp Arg Gly Asp Ile Thr Ile Gly Pro Pro Asn
                180                 185                 190

Val Glu Gly Arg Phe Thr Ile Ser Arg Asp Asn Ala Lys Asn Thr Gly
            195                 200                 205

Tyr Leu Gln Met Asn Ser Leu Ala Pro Asp Asp Thr Ala Val Tyr Tyr
            210                 215                 220

Cys Gly Ala Gly Thr Pro Leu Asn Pro Gly Ala Tyr Ile Tyr Asp Trp
225                 230                 235                 240

Ser Tyr Asp Tyr Trp Gly Arg Gly Thr Gln Val Thr Val Ser Ser Ala
                245                 250                 255

Ala Ala Glu Val Gln Leu Val Glu Ser Gly Gly Gly Leu Val Gln Ala
            260                 265                 270

Gly Gly Ser Leu Ser Ile Ser Cys Ala Ala Ser Gly Gly Ser Leu Ser
            275                 280                 285

Asn Tyr Val Leu Gly Trp Phe Arg Gln Ala Pro Gly Lys Glu Arg Glu
            290                 295                 300

Phe Val Ala Ala Ile Asn Trp Arg Gly Asp Ile Thr Ile Gly Pro Pro
305                 310                 315                 320

Asn Val Glu Gly Arg Phe Thr Ile Ser Arg Asp Asn Ala Lys Asn Thr
                325                 330                 335

Gly Tyr Leu Gln Met Asn Ser Leu Ala Pro Asp Asp Thr Ala Val Tyr
            340                 345                 350

Tyr Cys Gly Ala Gly Thr Pro Leu Asn Pro Gly Ala Tyr Ile Tyr Asp
            355                 360                 365

Trp Ser Tyr Asp Tyr Trp Gly Arg Gly Thr Gln Val Thr Val Ser Ser
            370                 375                 380

<210> SEQ ID NO 67
<211> LENGTH: 396
<212> TYPE: PRT
<213> ORGANISM: Artificial Sequence
<220> FEATURE:
<223> OTHER INFORMATION: Nanobody sequence

<400> SEQUENCE: 67

Glu Val Gln Leu Val Glu Ser Gly Gly Gly Leu Val Gln Ala Gly Gly
```

```
  1               5                  10                 15
Ser Leu Ser Ile Ser Cys Ala Ala Ser Gly Gly Ser Leu Ser Asn Tyr
             20                  25                  30
Val Leu Gly Trp Phe Arg Gln Ala Pro Gly Lys Glu Arg Glu Phe Val
             35                  40                  45
Ala Ala Ile Asn Trp Arg Gly Asp Ile Thr Ile Gly Pro Pro Asn Val
 50                  55                  60
Glu Gly Arg Phe Thr Ile Ser Arg Asp Asn Ala Lys Asn Thr Gly Tyr
 65                  70                  75                  80
Leu Gln Met Asn Ser Leu Ala Pro Asp Asp Thr Ala Val Tyr Tyr Cys
                 85                  90                  95
Gly Ala Gly Thr Pro Leu Asn Pro Gly Ala Tyr Ile Tyr Asp Trp Ser
                100                 105                 110
Tyr Asp Tyr Trp Gly Arg Gly Thr Gln Val Thr Val Ser Ser Gly Gly
                115                 120                 125
Gly Gly Ser Gly Gly Gly Ser Glu Val Gln Leu Val Glu Ser Gly Gly
            130                 135                 140
Gly Leu Val Gln Ala Gly Gly Ser Leu Ser Ile Ser Cys Ala Ala Ser
145                 150                 155                 160
Gly Gly Ser Leu Ser Asn Tyr Val Leu Gly Trp Phe Arg Gln Ala Pro
                165                 170                 175
Gly Lys Glu Arg Glu Phe Val Ala Ala Ile Asn Trp Arg Gly Asp Ile
            180                 185                 190
Thr Ile Gly Pro Pro Asn Val Glu Gly Arg Phe Thr Ile Ser Arg Asp
        195                 200                 205
Asn Ala Lys Asn Thr Gly Tyr Leu Gln Met Asn Ser Leu Ala Pro Asp
210                 215                 220
Asp Thr Ala Val Tyr Tyr Cys Gly Ala Gly Thr Pro Leu Asn Pro Gly
225                 230                 235                 240
Ala Tyr Ile Tyr Asp Trp Ser Tyr Asp Tyr Trp Gly Arg Gly Thr Gln
                245                 250                 255
Val Thr Val Ser Ser Gly Gly Gly Gly Ser Gly Gly Gly Ser Glu Val
            260                 265                 270
Gln Leu Val Glu Ser Gly Gly Gly Leu Val Gln Ala Gly Gly Ser Leu
        275                 280                 285
Ser Ile Ser Cys Ala Ala Ser Gly Gly Ser Leu Ser Asn Tyr Val Leu
    290                 295                 300
Gly Trp Phe Arg Gln Ala Pro Gly Lys Glu Arg Glu Phe Val Ala Ala
305                 310                 315                 320
Ile Asn Trp Arg Gly Asp Ile Thr Ile Gly Pro Pro Asn Val Glu Gly
                325                 330                 335
Arg Phe Thr Ile Ser Arg Asp Asn Ala Lys Asn Thr Gly Tyr Leu Gln
            340                 345                 350
Met Asn Ser Leu Ala Pro Asp Asp Thr Ala Val Tyr Tyr Cys Gly Ala
        355                 360                 365
Gly Thr Pro Leu Asn Pro Gly Ala Tyr Ile Tyr Asp Trp Ser Tyr Asp
    370                 375                 380
Tyr Trp Gly Arg Gly Thr Gln Val Thr Val Ser Ser
385                 390                 395

<210> SEQ ID NO 68
<211> LENGTH: 418
<212> TYPE: PRT
<213> ORGANISM: Artificial Sequence
```

<220> FEATURE:
<223> OTHER INFORMATION: Nanobody sequence

<400> SEQUENCE: 68

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Gly Gly Gly
130                 135                 140

Gly Ser Glu Val Gln Leu Val Glu Ser Gly Gly Gly Leu Val Gln Ala
145                 150                 155                 160

Gly Gly Ser Leu Ser Ile Ser Cys Ala Ala Ser Gly Gly Ser Leu Ser
                165                 170                 175

Asn Tyr Val Leu Gly Trp Phe Arg Gln Ala Pro Gly Lys Glu Arg Glu
            180                 185                 190

Phe Val Ala Ala Ile Asn Trp Arg Gly Asp Ile Thr Ile Gly Pro Pro
        195                 200                 205

Asn Val Glu Gly Arg Phe Thr Ile Ser Arg Asp Asn Ala Lys Asn Thr
    210                 215                 220

Gly Tyr Leu Gln Met Asn Ser Leu Ala Pro Asp Asp Thr Ala Val Tyr
225                 230                 235                 240

Tyr Cys Gly Ala Gly Thr Pro Leu Asn Pro Gly Ala Tyr Ile Tyr Asp
                245                 250                 255

Trp Ser Tyr Asp Tyr Trp Gly Arg Gly Thr Gln Val Thr Val Ser Ser
            260                 265                 270

Gly Gly Gly Gly Ser Gly Gly Gly Ser Gly Gly Gly Gly Ser Gly
        275                 280                 285

Gly Gly Gly Ser Glu Val Gln Leu Val Glu Ser Gly Gly Gly Leu Val
    290                 295                 300

Gln Ala Gly Gly Ser Leu Ser Ile Ser Cys Ala Ala Ser Gly Gly Ser
305                 310                 315                 320

Leu Ser Asn Tyr Val Leu Gly Trp Phe Arg Gln Ala Pro Gly Lys Glu
                325                 330                 335

Arg Glu Phe Val Ala Ala Ile Asn Trp Arg Gly Asp Ile Thr Ile Gly
            340                 345                 350

Pro Pro Asn Val Glu Gly Arg Phe Thr Ile Ser Arg Asp Asn Ala Lys
        355                 360                 365

Asn Thr Gly Tyr Leu Gln Met Asn Ser Leu Ala Pro Asp Asp Thr Ala
    370                 375                 380

Val Tyr Tyr Cys Gly Ala Gly Thr Pro Leu Asn Pro Gly Ala Tyr Ile
385                 390                 395                 400

```
Tyr Asp Trp Ser Tyr Asp Tyr Trp Gly Arg Gly Thr Gln Val Thr Val
                405                 410                 415

Ser Ser

<210> SEQ ID NO 69
<211> LENGTH: 408
<212> TYPE: PRT
<213> ORGANISM: Artificial Sequence
<220> FEATURE:
<223> OTHER INFORMATION: Nanobody sequence

<400> SEQUENCE: 69

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Leu Thr Leu Asp Tyr Tyr Ala Leu Gly Trp Phe Arg
305                 310                 315                 320

Gln Ala Pro Gly Lys Glu Arg Glu Gly Val Ser Cys Ile Ser Ser Ser
                325                 330                 335
```

```
Asp His Ser Thr Thr Tyr Thr Asp Ser Val Lys Gly Arg Phe Thr Ile
                340                 345                 350

Ser Trp Asp Asn Ala Lys Asn Thr Leu Tyr Leu Gln Met Asn Ser Leu
            355                 360                 365

Lys Pro Gly Asp Thr Ala Val Tyr Tyr Cys Ala Ala Asp Pro Ala Leu
        370                 375                 380

Gly Cys Tyr Ser Gly Ser Tyr Tyr Pro Arg Tyr Asp Tyr Trp Gly Gln
385                 390                 395                 400

Gly Thr Gln Val Thr Val Ser Ser
                405

<210> SEQ ID NO 70
<211> LENGTH: 408
<212> TYPE: PRT
<213> ORGANISM: Artificial Sequence
<220> FEATURE:
<223> OTHER INFORMATION: Nanobody sequence

<400> SEQUENCE: 70

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Leu Thr Leu Asp Tyr Tyr Ala Leu Gly
                165                 170                 175

Trp Phe Arg Gln Ala Pro Gly Lys Glu Arg Glu Gly Val Ser Cys Ile
            180                 185                 190

Ser Ser Ser Asp His Ser Thr Thr Tyr Thr Asp Ser Val Lys Gly Arg
        195                 200                 205

Phe Thr Ile Ser Trp Asp Asn Ala Lys Asn Thr Leu Tyr Leu Gln Met
    210                 215                 220

Asn Ser Leu Lys Pro Gly Asp Thr Ala Val Tyr Tyr Cys Ala Ala Asp
225                 230                 235                 240

Pro Ala Leu Gly Cys Tyr Ser Gly Ser Tyr Tyr Pro Arg Tyr Asp Tyr
                245                 250                 255

Trp Gly Gln Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285
```

-continued

Ser Gly Gly Leu Val Gln Ala Gly Gly Ser Leu Ser Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
                355                 360                 365

Ala Pro Asp Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405

<210> SEQ ID NO 71
<211> LENGTH: 408
<212> TYPE: PRT
<213> ORGANISM: Artificial Sequence
<220> FEATURE:
<223> OTHER INFORMATION: Nanobody sequence

<400> SEQUENCE: 71

Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Glu Val Gln
            130                 135                 140

Leu Val Glu Ser Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

```
Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Ala Gly Gly Ser Leu Ser Ile Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Ala Pro Asp Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405

<210> SEQ ID NO 72
<211> LENGTH: 408
<212> TYPE: PRT
<213> ORGANISM: Artificial Sequence
<220> FEATURE:
<223> OTHER INFORMATION: Nanobody sequence

<400> SEQUENCE: 72

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190
```

```
Asn Trp Arg Gly Asp Ile Thr Ile Gly Pro Pro Asn Val Glu Gly Arg
            195                 200                 205

Phe Thr Ile Ser Arg Asp Asn Ser Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
            275                 280                 285

Ser Gly Gly Gly Leu Val Gln Pro Gly Gly Ser Leu Arg Ile Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
            325                 330                 335

Gly Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
            355                 360                 365

Arg Pro Glu Asp Thr Ala Val Tyr Tyr Cys Gly Ala Gly Thr Pro Leu
            370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 73
<211> LENGTH: 408
<212> TYPE: PRT
<213> ORGANISM: Artificial Sequence
<220> FEATURE:
<223> OTHER INFORMATION: Nanobody sequence

<400> SEQUENCE: 73

Asp Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
            115                 120                 125

Gly Gly Ser Gly Gly Gly Gly Ser Gly Gly Gly Gly Ser Glu Val Gln
            130                 135                 140
```

```
Leu Leu Glu Ser Gly Gly Gly Leu Val Gln Pro Gly Gly Ser Leu Arg
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Gly Asp Ile Thr Ile Gly Pro Pro Asn Val Glu Gly Arg
                195                 200                 205

Phe Thr Ile Ser Arg Asp Asn Ser Lys Asn Thr Leu Tyr Leu Gln Met
            210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Glu Val Gln Leu Leu Glu
                275                 280                 285

Ser Gly Gly Gly Leu Val Gln Pro Gly Gly Ser Leu Arg Ile Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ser Lys Asn Thr Leu Tyr Leu Gln Met Asn Ser Leu
                355                 360                 365

Arg Pro Glu Asp Thr Ala Val Tyr Tyr Cys Gly Ala Gly Thr Pro Leu
            370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 74
<211> LENGTH: 408
<212> TYPE: PRT
<213> ORGANISM: Artificial Sequence
<220> FEATURE:
<223> OTHER INFORMATION: Nanobody sequence

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95
```

Gly Ala Gly Thr Pro Leu Asn Pro Gly Ala Tyr Ile Tyr Asp Trp Ser
                100                 105                 110

Tyr Asp Tyr Trp Gly Gln Gly Thr Leu Val Thr Val Ser Ser Gly Gly
            115                 120                 125

Gly Gly Ser Gly Gly Gly Ser Gly Gly Gly Ser Glu Val Gln
        130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Asp Asp Ile Thr Ile Gly Pro Pro Asn Val Glu Gly Arg
            195                 200                 205

Phe Thr Ile Ser Arg Asp Asn Ala Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
            275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
            325                 330                 335

Asp Asp Ile Thr Ile Gly Pro Pro Asn Val Glu Gly Arg Phe Thr Ile
            340                 345                 350

Ser Arg Asp Asn Ala Lys Asn Thr Leu Tyr Leu Gln Met Asn Ser Leu
            355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 75
<211> LENGTH: 408
<212> TYPE: PRT
<213> ORGANISM: Artificial Sequence
<220> FEATURE:
<223> OTHER INFORMATION: Nanobody sequence

<400> SEQUENCE: 75

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

-continued

Ala Ala Ile Asn Trp Arg Asp Asp Ile Thr Ile Gly Pro Pro Asn Val
 50                  55                  60

Glu Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
                180                 185                 190

Asn Trp Arg Asp Asp Ile Thr Ile Gly Pro Pro Asn Val Glu Gly Arg
            195                 200                 205

Phe Thr Ile Ser Arg Asp Asn Ala Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Asp Asp Ile Thr Ile Gly Pro Pro Asn Val Glu Gly Arg Phe Thr Ile
            340                 345                 350

Ser Arg Asp Asn Ala Lys Asn Thr Leu Tyr Leu Gln Met Asn Ser Leu
        355                 360                 365

Arg Pro Glu Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 76
<211> LENGTH: 408
<212> TYPE: PRT
<213> ORGANISM: Artificial Sequence
<220> FEATURE:
<223> OTHER INFORMATION: Nanobody sequence

<400> SEQUENCE: 76

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
            165                 170                 175

Trp Phe Arg Gln Ala Pro Gly Lys Gly Arg Glu Phe Val Ala Ala Ile
        180                 185                 190

Asn Trp Arg Gly Asp Ile Thr Ile Gly Pro Pro Asn Val Glu Gly Arg
    195                 200                 205

Phe Thr Ile Ser Arg Asp Asn Ser Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Gln Gly Thr Leu Val Thr Val Ser Ser Gly Gly Gly Gly Ser
        260                 265                 270

Gly Gly Gly Gly Ser Gly Gly Gly Ser Glu Val Gln Leu Leu Glu
    275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
            325                 330                 335

Gly Asp Ile Thr Ile Gly Pro Pro Asn Val Glu Gly Arg Phe Thr Ile
        340                 345                 350

Ser Arg Asp Asn Ser Lys Asn Thr Leu Tyr Leu Gln Met Asn Ser Leu
    355                 360                 365

Arg Pro Glu Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
            405
```

```
<210> SEQ ID NO 77
<211> LENGTH: 408
<212> TYPE: PRT
<213> ORGANISM: Artificial Sequence
<220> FEATURE:
<223> OTHER INFORMATION: Nanobody sequence

<400> SEQUENCE: 77

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
        355                 360                 365

Arg Pro Glu Asp Thr Ala Val Tyr Tyr Cys Gly Ala Gly Thr Pro Leu
```

```
            370                 375                 380
Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 78
<211> LENGTH: 408
<212> TYPE: PRT
<213> ORGANISM: Artificial Sequence
<220> FEATURE:
<223> OTHER INFORMATION: Nanobody sequence

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Asp Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
```

```
                    325                 330                 335
Asp Asp Ile Thr Ile Gly Pro Pro Asn Val Glu Gly Arg Phe Thr Ile
                340                 345                 350

Ser Arg Asp Asn Ser Lys Asn Thr Leu Tyr Leu Gln Met Asn Ser Leu
                355                 360                 365

Arg Pro Glu Asp Thr Ala Val Tyr Tyr Cys Gly Ala Gly Thr Pro Leu
            370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405
```

<210> SEQ ID NO 79
<211> LENGTH: 408
<212> TYPE: PRT
<213> ORGANISM: Artificial Sequence
<220> FEATURE:
<223> OTHER INFORMATION: Nanobody sequence

<400> SEQUENCE: 79

```
Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Asp Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Glu Val Gln Leu Leu Glu
```

```
            275                 280                 285
Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Asp Asp Ile Thr Ile Gly Pro Pro Asn Val Glu Gly Arg Phe Thr Ile
                340                 345                 350

Ser Arg Asp Asn Ser Lys Asn Thr Leu Tyr Leu Gln Met Asn Ser Leu
                355                 360                 365

Arg Pro Glu Asp Thr Ala Val Tyr Tyr Cys Gly Ala Gly Thr Pro Leu
                370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405
```

<210> SEQ ID NO 80
<211> LENGTH: 408
<212> TYPE: PRT
<213> ORGANISM: Artificial Sequence
<220> FEATURE:
<223> OTHER INFORMATION: Nanobody sequence

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
                35                  40                  45

Ala Ala Ile Asn Trp Arg Gly Asp Ile Thr Ile Gly Pro Pro Asn Val
                50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Gln Gly Thr Leu Val Thr Val Ser Ser Gly Gly
                115                 120                 125

Gly Gly Ser Gly Gly Gly Gly Ser Gly Gly Gly Gly Ser Glu Val Gln
                130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
                180                 185                 190

Asn Trp Arg Gly Asp Ile Thr Ile Gly Pro Pro Asn Val Glu Gly Arg
                195                 200                 205

Phe Thr Ile Ser Arg Asp Asn Ala Lys Asn Thr Gly Tyr Leu Gln Met
                210                 215                 220

Asn Ser Leu Arg Pro Asp Asp Thr Ala Val Tyr Tyr Cys Gly Ala Gly
```

```
                225                 230                 235                 240
Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
                260                 265                 270

Gly Gly Gly Gly Ser Gly Gly Gly Ser Glu Val Gln Leu Val Glu
                275                 280                 285

Ser Gly Gly Gly Leu Val Gln Pro Gly Gly Ser Leu Arg Leu Ser Cys
                290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
                355                 360                 365

Arg Pro Asp Asp Thr Ala Val Tyr Tyr Cys Gly Ala Gly Thr Pro Leu
                370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 81
<211> LENGTH: 408
<212> TYPE: PRT
<213> ORGANISM: Artificial Sequence
<220> FEATURE:
<223> OTHER INFORMATION: Nanobody sequence

<400> SEQUENCE: 81

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
                35                  40                  45

Ala Ala Ile Asn Trp Arg Gly Asp Ile Thr Ile Gly Pro Pro Asn Val
                50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Gln Gly Thr Leu Val Thr Val Ser Ser Gly Gly
                115                 120                 125

Gly Gly Ser Gly Gly Gly Gly Ser Gly Gly Gly Ser Glu Val Gln
                130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
```

```
                180             185             190
Asn Trp Arg Gly Asp Ile Thr Ile Gly Pro Pro Asn Val Glu Gly Arg
            195                 200                 205

Phe Thr Ile Ser Arg Asp Asn Ala Lys Asn Thr Gly Tyr Leu Gln Met
        210                 215                 220

Asn Ser Leu Arg Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
                260                 265                 270

Gly Gly Gly Gly Ser Gly Gly Gly Ser Glu Val Gln Leu Val Glu
            275                 280                 285

Ser Gly Gly Gly Leu Val Gln Pro Gly Gly Ser Leu Arg Leu Ser Cys
            290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
            355                 360                 365

Arg Pro Asp Asp Thr Ala Val Tyr Tyr Cys Gly Ala Gly Thr Pro Leu
        370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 82
<211> LENGTH: 408
<212> TYPE: PRT
<213> ORGANISM: Artificial Sequence
<220> FEATURE:
<223> OTHER INFORMATION: Nanobody sequence

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
```

```
           130                 135                 140
Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
                180                 185                 190

Asn Trp Arg Gly Asp Ile Thr Ile Gly Pro Pro Asn Val Glu Gly Arg
            195                 200                 205

Phe Thr Ile Ser Arg Asp Asn Ala Lys Asn Thr Gly Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
                260                 265                 270

Gly Gly Gly Gly Ser Gly Gly Gly Ser Glu Val Gln Leu Val Glu
            275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
            355                 360                 365

Arg Pro Glu Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405
```

<210> SEQ ID NO 83
<211> LENGTH: 408
<212> TYPE: PRT
<213> ORGANISM: Artificial Sequence
<220> FEATURE:
<223> OTHER INFORMATION: Nanobody sequence

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
```

```
                85                  90                  95
Gly Ala Gly Thr Pro Leu Asn Pro Gly Ala Tyr Ile Tyr Asp Trp Ser
                100                 105                 110

Tyr Asp Tyr Trp Gly Arg Gly Thr Leu Val Thr Val Ser Ser Gly Gly
            115                 120                 125

Gly Gly Ser Gly Gly Gly Ser Gly Gly Gly Ser Glu Val Gln
        130                 135                 140

Leu Val Glu Ser Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
                180                 185                 190

Asn Trp Arg Gly Asp Ile Thr Ile Gly Pro Pro Asn Val Glu Gly Arg
                195                 200                 205

Phe Thr Ile Ser Arg Asp Asn Ala Lys Asn Thr Gly Tyr Leu Gln Met
                210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Leu Val Thr Val Ser Ser Gly Gly Gly Gly Ser
                260                 265                 270

Gly Gly Gly Gly Ser Gly Gly Gly Ser Glu Val Gln Leu Val Glu
        275                 280                 285

Ser Gly Gly Leu Val Gln Pro Gly Gly Ser Leu Arg Leu Ser Cys
        290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
                355                 360                 365

Arg Pro Glu Asp Thr Ala Val Tyr Tyr Cys Gly Ala Gly Thr Pro Leu
                370                 375                 380

Asn Pro Gly Ala Tyr Ile Tyr Asp Trp Ser Tyr Asp Tyr Trp Gly Arg
385                 390                 395                 400

Gly Thr Leu Val Thr Val Ser Ser
                405

<210> SEQ ID NO 84
<211> LENGTH: 408
<212> TYPE: PRT
<213> ORGANISM: Artificial Sequence
<220> FEATURE:
<223> OTHER INFORMATION: Nanobody sequence

<400> SEQUENCE: 84

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
```

```
            35                  40                  45
Ala Ala Ile Asn Trp Arg Gly Asp Ile Thr Ile Gly Pro Pro Asn Val
50                  55                  60
Glu Gly Arg Phe Thr Ile Ser Arg Asp Asn Ala Lys Asn Thr Gly Tyr
65                  70                  75                  80
Leu Gln Met Asn Ser Leu Arg Pro Glu Asp Thr Ala Val Tyr Tyr Cys
                85                  90                  95
Gly Ala Gly Thr Pro Leu Asn Pro Gly Ala Tyr Ile Tyr Asp Trp Ser
            100                 105                 110
Tyr Asp Tyr Trp Gly Arg Gly Thr Leu Val Thr Val Ser Ser Gly Gly
        115                 120                 125
Gly Gly Ser Gly Gly Gly Ser Gly Gly Gly Ser Glu Val Gln
130                 135                 140
Leu Val Glu Ser Gly Gly Gly Leu Val Gln Pro Gly Gly Ser Leu Arg
145                 150                 155                 160
Leu Ser Cys Ala Ala Ser Gly Gly Ser Leu Ser Asn Tyr Val Leu Gly
                165                 170                 175
Trp Phe Arg Gln Ala Pro Gly Lys Glu Arg Glu Phe Val Ala Ala Ile
            180                 185                 190
Asn Trp Arg Gly Asp Ile Thr Ile Gly Pro Pro Asn Val Glu Gly Arg
        195                 200                 205
Phe Thr Ile Ser Arg Asp Asn Ala Lys Asn Thr Gly Tyr Leu Gln Met
210                 215                 220
Asn Ser Leu Arg Pro Glu Asp Thr Ala Val Tyr Tyr Cys Gly Ala Gly
225                 230                 235                 240
Thr Pro Leu Asn Pro Gly Ala Tyr Ile Tyr Asp Trp Ser Tyr Asp Tyr
                245                 250                 255
Trp Gly Arg Gly Thr Leu Val Thr Val Ser Ser Gly Gly Gly Gly Ser
            260                 265                 270
Gly Gly Gly Gly Ser Gly Gly Gly Ser Glu Val Gln Leu Val Glu
        275                 280                 285
Ser Gly Gly Gly Leu Val Gln Pro Gly Gly Ser Leu Arg Leu Ser Cys
290                 295                 300
Ala Ala Ser Gly Gly Ser Leu Ser Asn Tyr Val Leu Gly Trp Phe Arg
305                 310                 315                 320
Gln Ala Pro Gly Lys Glu Arg Glu Phe Val Ala Ala Ile Asn Trp Arg
                325                 330                 335
Gly Asp Ile Thr Ile Gly Pro Pro Asn Val Glu Gly Arg Phe Thr Ile
            340                 345                 350
Ser Arg Asp Asn Ala Lys Asn Thr Gly Tyr Leu Gln Met Asn Ser Leu
        355                 360                 365
Arg Pro Glu Asp Thr Ala Val Tyr Tyr Cys Gly Ala Gly Thr Pro Leu
370                 375                 380
Asn Pro Gly Ala Tyr Ile Tyr Asp Trp Ser Tyr Asp Tyr Trp Gly Arg
385                 390                 395                 400
Gly Thr Leu Val Thr Val Ser Ser
                405

<210> SEQ ID NO 85
<211> LENGTH: 408
<212> TYPE: PRT
<213> ORGANISM: Artificial Sequence
<220> FEATURE:
<223> OTHER INFORMATION: Nanobody sequence
```

```
<400> SEQUENCE: 85

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405
```

```
<210> SEQ ID NO 86
<211> LENGTH: 5
<212> TYPE: PRT
<213> ORGANISM: Artificial Sequence
<220> FEATURE:
<223> OTHER INFORMATION: Linker sequence

<400> SEQUENCE: 86

Gly Gly Gly Gly Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Linker sequence

<400> SEQUENCE: 87

Ser Gly Gly Ser Gly Gly Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Linker sequence

<400> SEQUENCE: 88

Gly Gly Gly Gly Ser Gly Gly Gly Ser
1               5

<210> SEQ ID NO 89
<211> LENGTH: 9
<212> TYPE: PRT
<213> ORGANISM: Artificial Sequence
<220> FEATURE:
<223> OTHER INFORMATION: Linker sequence

<400> SEQUENCE: 89

Gly Gly Gly Gly Ser Gly Gly Gly Ser
1               5

<210> SEQ ID NO 90
<211> LENGTH: 10
<212> TYPE: PRT
<213> ORGANISM: Artificial Sequence
<220> FEATURE:
<223> OTHER INFORMATION: Linker sequence

<400> SEQUENCE: 90

Gly Gly Gly Gly Ser Gly Gly Gly Gly Ser
1               5                   10

<210> SEQ ID NO 91
<211> LENGTH: 15
<212> TYPE: PRT
<213> ORGANISM: Artificial Sequence
<220> FEATURE:
<223> OTHER INFORMATION: Linker sequence

<400> SEQUENCE: 91

Gly Gly Gly Gly Ser Gly Gly Gly Gly Ser Gly Gly Gly Gly Ser
1               5                   10                  15
```

<210> SEQ ID NO 92
<211> LENGTH: 18
<212> TYPE: PRT
<213> ORGANISM: Artificial Sequence
<220> FEATURE:
<223> OTHER INFORMATION: Linker sequence

<400> SEQUENCE: 92

Gly Gly Gly Gly Ser Gly Gly Gly Gly Ser Gly Gly Gly Gly Gly Gly
1               5                   10                  15

Gly Ser

<210> SEQ ID NO 93
<211> LENGTH: 20
<212> TYPE: PRT
<213> ORGANISM: Artificial Sequence
<220> FEATURE:
<223> OTHER INFORMATION: Linker sequence

<400> SEQUENCE: 93

Gly Gly Gly Gly Ser Gly Gly Gly Gly Ser Gly Gly Gly Gly Ser Gly
1               5                   10                  15

Gly Gly Gly Ser
            20

<210> SEQ ID NO 94
<211> LENGTH: 25
<212> TYPE: PRT
<213> ORGANISM: Artificial Sequence
<220> FEATURE:
<223> OTHER INFORMATION: Linker sequence

<400> SEQUENCE: 94

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 95
<211> LENGTH: 30
<212> TYPE: PRT
<213> ORGANISM: Artificial Sequence
<220> FEATURE:
<223> OTHER INFORMATION: Linker sequence

<400> SEQUENCE: 95

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 96
<211> LENGTH: 35
<212> TYPE: PRT
<213> ORGANISM: Artificial Sequence
<220> FEATURE:
<223> OTHER INFORMATION: Linker sequence

<400> SEQUENCE: 96

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 97
<211> LENGTH: 15
<212> TYPE: PRT
<213> ORGANISM: Artificial Sequence
<220> FEATURE:
<223> OTHER INFORMATION: Linker sequence

<400> SEQUENCE: 97

Glu Pro Lys Ser Cys Asp Lys Thr His Thr Cys Pro Pro Cys Pro
1               5                   10                  15

<210> SEQ ID NO 98
<211> LENGTH: 24
<212> TYPE: PRT
<213> ORGANISM: Artificial Sequence
<220> FEATURE:
<223> OTHER INFORMATION: Linker sequence

<400> SEQUENCE: 98

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 99
<211> LENGTH: 12
<212> TYPE: PRT
<213> ORGANISM: Artificial Sequence
<220> FEATURE:
<223> OTHER INFORMATION: Linker sequence

<400> SEQUENCE: 99

Glu Pro Lys Thr Pro Lys Pro Gln Pro Ala Ala Ala
1               5                   10

<210> SEQ ID NO 100
<211> LENGTH: 62
<212> TYPE: PRT
<213> ORGANISM: Artificial Sequence
<220> FEATURE:
<223> OTHER INFORMATION: Linker sequence

<400> SEQUENCE: 100

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 101
<211> LENGTH: 3
<212> TYPE: PRT

```
<213> ORGANISM: Artificial Sequence
<220> FEATURE:
<223> OTHER INFORMATION: Linker sequence

<400> SEQUENCE: 101

Ala Ala Ala
1
```

The invention claimed is:

1. A method for treating a respiratory syncytial virus (RSV) infection in a young child, the method comprising the following step:
   administering to a subject a polypeptide that binds a protein of human RSV (hRSV), wherein the protein is glycoprotein F (F-protein), wherein the polypeptide has the amino acid sequence of SEQ ID NO: 71, wherein the polypeptide is administered by inhalation with a vibrating mesh nebulizer at a deposited dose of 0.020-0.040 mg/kg daily and wherein the subject is a young child.

2. The method of claim 1, wherein the polypeptide is administered at an inhaled dose of 0.20-0.40 mg/kg daily.

3. The method of claim 1, wherein the polypeptide is administered at a nominal dose of 1.00-2.00 mg/kg daily.

4. The method of claim 1, wherein the step of administering is performed daily for 2 to 5 consecutive days.

5. The method of claim 1, wherein the step of administering is performed daily for 3 consecutive days.

6. The method of claim 1, wherein the young child is less than 2 years old.

7. The method of claim 1, wherein the step of administering is performed by use of a nebulizer.

8. The method of claim 1, wherein the polypeptide is the only therapeutic agent administered to the young child.

9. The method of claim 1, further comprising the step of administering to the young child an additional therapeutic agent.

10. The method of claim 9, wherein the additional therapeutic agent is a bronchodilator.

* * * * *